United States Patent
Zaccarin et al.

(10) Patent No.: US 8,993,307 B2
(45) Date of Patent: *Mar. 31, 2015

(54) HIGH MULTIPLEX ARRAYS AND SYSTEMS

(75) Inventors: Denis Zaccarin, San Jose, CA (US);
Paul Lundquist, San Jose, CA (US);
Peiqian Zhao, Mountain View, CA (US);
Cheng Frank Zhong, Fremont, CA (US); Stephen Turner, Menlo Park, CA (US); Yanqiao Huang, San Mateo, CA (US); Pezhman Monadgemi, Fremont, CA (US); Ravi Saxena, San Jose, CA (US); Annette Grot, Cupertino, CA (US); Aaron Rulison, Los Altos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,497

(22) Filed: Jul. 18, 2012

(65) Prior Publication Data

US 2013/0023039 A1 Jan. 24, 2013

Related U.S. Application Data

(63) Continuation of application No. 12/567,526, filed on Sep. 25, 2009, now Pat. No. 8,247,216.

(60) Provisional application No. 61/101,555, filed on Sep. 30, 2008, provisional application No. 61/223,628, filed on Jul. 7, 2009.

(51) Int. Cl.
*C12M 1/34* (2006.01)
*G01N 21/64* (2006.01)
(Continued)

(52) U.S. Cl.
CPC .......... *G01N 21/6452* (2013.01); *G01N 21/253* (2013.01); *G02B 6/131* (2013.01); *G02B 6/136* (2013.01)
USPC ..................................... 435/283.1; 359/221.2

(58) Field of Classification Search
None
See application file for complete search history.

(56) References Cited

U.S. PATENT DOCUMENTS

| 4,649,280 A | 3/1987 | Holland et al. |
| 5,228,109 A | 7/1993 | Fujii et al. |

(Continued)

FOREIGN PATENT DOCUMENTS

| EP | 1425570 B1 | 3/2009 |
| JP | 4091212 B2 | 3/2008 |

(Continued)

OTHER PUBLICATIONS

EP Search Report dated Sep. 21, 2012 for related case EP 09818087.

(Continued)

*Primary Examiner* — Betty Forman
(74) *Attorney, Agent, or Firm* — Robert H. Reamey

(57) ABSTRACT

Apparatus, systems and methods for use in analyzing discrete reactions at ultra high multiplex with reduced optical noise, and increased system flexibility. Apparatus include substrates having integrated optical components that increase multiplex capability by one or more of increasing density of reaction regions, improving transmission of light to or collection of light from discrete reactions regions. Integrated optical components include reflective optical elements which re-direct illumination light and light emitted from the discrete regions to more efficiently collect emitted light. Particularly preferred applications include single molecule reaction analysis, such as polymerase mediated template dependent nucleic acid synthesis and sequence determination.

14 Claims, 42 Drawing Sheets

(51) Int. Cl.
  *G01N 21/25* (2006.01)
  *G02B 6/13* (2006.01)
  *G02B 6/136* (2006.01)

(56) References Cited

U.S. PATENT DOCUMENTS

| | | | |
|---|---|---|---|
| 6,437,345 | B1 | 8/2002 | Bruno-Raimondi et al. |
| 6,649,403 | B1 | 11/2003 | McDevitt et al. |
| 6,917,726 | B2 | 7/2005 | Levene et al. |
| 7,170,050 | B2 | 1/2007 | Turner et al. |
| 7,315,503 | B2 | 1/2008 | Cho et al. |
| 7,714,303 | B2 | 5/2010 | Lundquist et al. |
| 8,247,216 | B2 * | 8/2012 | Zaccarin et al. ........... 435/283.1 |
| 8,335,029 | B2 * | 12/2012 | Monadgemi ............... 359/221.2 |
| 2003/0059820 | A1 | 3/2003 | Vo-Dinh |
| 2004/0124336 | A1 | 7/2004 | MacCraith et al. |
| 2005/0053974 | A1 | 3/2005 | Lakowicz et al. |
| 2006/0060766 | A1 | 3/2006 | Turner et al. |
| 2007/0134128 | A1 | 6/2007 | Korlach |
| 2007/0188750 | A1 | 8/2007 | Lundquist et al. |
| 2007/0206187 | A1 | 9/2007 | Lundquist et al. |
| 2007/0236628 | A1 | 10/2007 | Epstein |
| 2009/0024331 | A1 | 1/2009 | Tomaney et al. |
| 2009/0056790 | A1 | 3/2009 | Tian et al. |
| 2010/0065726 | A1 | 3/2010 | Zhong et al. |

FOREIGN PATENT DOCUMENTS

| | | |
|---|---|---|
| WO | 0245845 A2 | 6/2002 |
| WO | 02059583 A1 | 8/2002 |
| WO | 03023377 A1 | 3/2003 |
| WO | 2006044078 A2 | 4/2006 |
| WO | 2007095119 A2 | 8/2007 |
| WO | 2007095235 A2 | 8/2007 |
| WO | 2008012767 A2 | 1/2008 |

OTHER PUBLICATIONS

First Office Action dated Nov. 27, 2012 for related case CN 200980148101.0.
EID, et al., "Real-time DNA sequencing from single polymerase molecules" Science (2009) 323(5910):133-138.
Gryczynski, I. et al., "Radiative decay engineering 4. Experimental studies of surface plasmon-coupled directional emission" Anal. Biochem (2004) 324:170-182.
Hellen, E.H. et al., "Fluorescence emission at dielectric and metal-film interfaces" J Opt. Soc. Am. B (1987) 4 (3):337-350.
Korlach, J. et al., "Selective aluminum passivation for targeted immobilization of single DNA polymerase molecules in zero-mode waveguide nanostructures" PNAS 2008 105(4)1176-1181.
Lakowicz, J.R. "Radiative decay engineering 3. Surface plasmon-coupled directional emission" Anal. Biochem (2004) 324:153-169.
Levene et al., "Zero-mode waveguides for single-molecule analysis at high concentrations" Science (2003) 299 (5607):682-686.
Lundquist et al. "Parallel confocal detection of single molecules in real time" Opt Lett (2008) 33(9):1026-1028.
Mattheyses, A.L. et al., "Fluorescence emission patterns near glass and metal-coated surfaces investigated with back focal plane imaging" J Biomed Opt (2005) 10(5):054007-1 to 054007-6.
MacCraith, B. evaluation Angular emission profiles from fluorsneare a metallic or non-metallic interface, In my opinion, when it comes to TIRF, Axelrod has lead the way, both theoretically (Hellen and Axelrod 1987) and experimentally (Mattheyses and Axelrod 2005).
Smith, D.S. et al., "Signal enhancement of surface plasmon-coupled directional emission by a conical minor" Appl Opt (2008) 47(28):5229-5234.
Sullivan, K.G. et al., "Directional, enhanced fluorescence from molecules near a periodic surface" Appl Opt (1994) 33(13):2447-2454.
Weber, W.H. et al. "Energy transfer from an excited dye molecule to the surface plasmons of an adjacent metal" Opt Lett (1979) 4(8)236-238.
International Search Report and Written Opinion dated Jul. 16, 2010 for corresponding application PCT/US2009/005319.
International Preliminary Report on Patentability dated Apr. 14, 2011 for corresponding application PCT/US2009/005319.
First Office Action dated Jun. 19, 2013 for related case AU 2009300369.
Second Office Action dated Sep. 22, 2013 for related case CN 200980148101.0.
First Exam Report dated Sep. 12, 2013 for related case EP 09818087.
Second Office Action dated Apr. 15, 2014 for related case AU 2009300369.
Decision on Rejection dated Mar. 31, 2014 for related case CN 200980146101.0.

* cited by examiner

Micromirror Illumination

HIGH MULTIPLEX ARRAYS AND SYSTEMS

CROSS-REFERENCE TO RELATED APPLICATIONS

The present application is a continuation of U.S. patent application Ser. No. 12/567,526 filed Sep. 25, 2009, which claims priority from Provisional U.S. Patent Application No. 61/101,555, filed Sep. 30, 2008, and Provisional U.S. Patent Application No. 61/223,628 filed Jul. 7, 2009, the full disclosures of which are hereby incorporated by reference in their entirety for all purposes.

STATEMENT REGARDING FEDERALLY SPONSORED RESEARCH

Not Applicable.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex. The present invention meets these and a variety of other needs.

BRIEF SUMMARY OF THE INVENTION

The invention provides methods, substrates and systems for very high multiplex analysis of reaction regions on analytical substrates, and particularly for multiplexed systems for carrying out highly sensitive, low signal producing reactions, such as single molecule fluorescence analyses, e.g., as used in single molecule real time nucleic acid sequencing technologies.

An aspect of the invention is a method for producing a substrate comprising an array of micromirrors wherein each micromirror is associated with a zero-mode waveguide comprising: a) providing a transparent substrate having a top surface; b) patterning and etching the transparent substrate to form an array of protrusions having tops and sides; c) depositing a cladding material such that the tops of the protrusions comprise a cladding; d) forming an array of apertures through the cladding such that the top of each protrusion comprises an aperture; and e) depositing a reflective deposition material such that the sides of the each protrusions comprise a reflective layer; whereby the array of protrusions comprises an array of micromirrors, and the aperture at the top of each protrusion comprises a zero-mode waveguide.

In some embodiments step b) of patterning and etching the transparent substrate is carried out after steps c) and d) of depositing the cladding material and forming the array of apertures. In some embodiments steps c) and d) of depositing the cladding material and forming the array of apertures are carried out after step b) of patterning and etching the transparent substrate.

In some embodiments the transparent substrate comprises a silica-based material. In some embodiments the transparent substrate comprises fused silica. In some embodiments the cladding material comprises aluminum. In some embodiments the reflective deposition material comprises aluminum.

In some embodiments the etching of the transparent substrate comprises a reactive ion etching process. In some embodiments the protrusions comprise conical, pyramidal, or parabolic shapes. In some embodiments the protrusions comprise truncated cones. In some embodiments the tops of the truncated cones are between 1 micron and 10 microns in diameter. In some embodiments the number of protrusions on the substrate is between 1,000 and 1,000,000. In some embodiments the number of protrusions on the substrate is between 10,000 and 500,000.

An aspect of the invention is a method comprising the steps of: a) providing a transparent substrate having a top surface onto which a metal cladding layer having an array of apertures is disposed; b) depositing a first resist onto the cladding layer; c) patterning the first resist to produce an array of regions of remaining resist, each region of remaining resist comprising a region of the metal cladding layer comprising an aperture; d) etching to remove regions of the cladding layer, and transparent substrate whereby an array of protrusions is formed, whereby the regions of remaining resist comprising regions of metal cladding layer are on the tops of the protrusions; e) depositing a metal deposition layer whereby the metal deposition layer contacts the regions of metal cladding layer on the tops of the protrusions; f) depositing a second resist; g) patterning the second resist to expose regions of metal deposition layer on top of the protrusions; and h) treating the structure from step (g) to remove exposed regions of metal deposition layer.

An aspect of the invention is a method comprising the steps of: a) providing a transparent substrate having a top surface onto which a metal cladding layer having an array of apertures is disposed; b) depositing a protective coating over the metal cladding layer; c) depositing a first resist onto the protective layer; d) patterning the first resist to produce an array of regions of remaining resist, each region of remaining resist comprising a region of the metal cladding layer comprising an aperture; e) etching to remove regions of the protective layer, cladding layer, and transparent substrate whereby an array of protrusions is formed, whereby the regions of remaining resist comprising regions of metal cladding layer are on the tops of the protrusions; f) removing the first resist; g) depositing a metal deposition layer whereby the metal deposition layer contacts the regions of metal cladding layer on the tops of the protrusions; h) depositing a second resist; i) patterning the second resist to expose regions of metal deposition layer on top of the protrusions; and j) treating the structure from step (i) to remove exposed regions of the metal deposition layer and to remove the protective coat.

An aspect of the invention is a method comprising the steps of: a) providing a transparent substrate having a top surface onto which a metal cladding layer having an array of apertures is disposed; b) depositing a sacrificial layer over the metal cladding layer; c) depositing a first resist onto the sacrificial layer; d) patterning the first resist to produce an array of regions of remaining resist, each region of remaining resist comprising a region of the metal cladding layer comprising an aperture; e) etching to remove regions of the sacrificial layer, cladding layer, and transparent substrate whereby an array of protrusions is formed, whereby the regions of remaining resist comprising regions of metal cladding layer are on the tops of the protrusions; f) removing the first resist; g) treating the substrate to pull back the sacrificial layer; h) depositing a metal deposition layer whereby the metal deposition layer contacts the regions of metal cladding layer on the tops of the protrusions; i) treating the structure from step (h) to release the sacrificial layer, thereby removing portions of the metal deposition layer on the sacrificial layer and exposing the apertures. In some embodiments the sacrificial layer comprises germanium or silicon.

An aspect of the invention is a method comprising the steps of: a) providing a transparent substrate having a top surface onto which a metal cladding layer having an array of apertures is disposed; b) depositing a protective layer onto the metal cladding layer. c) depositing a first resist onto the protective layer; d) patterning the first resist to produce an array of regions of remaining resist, each region of remaining resist comprising a region of the metal cladding layer comprising an aperture; e) etching to remove regions of the protective layer, cladding layer, and transparent substrate whereby an array of protrusions is formed, whereby the regions of remaining resist comprising regions of metal cladding layer are on the tops of the protrusions; f) removing the first resist and protective layer; g) producing an array of pillars on the tops of the protrusions at least partially covering the regions of metal cladding layer; h) depositing a metal deposition layer whereby the metal deposition layer contacts the regions of metal cladding layer on the tops of the protrusions; and i) treating the structure from step (h) to remove the array of pillars thereby removing a portion of the metal deposition layer.

An aspect of the invention is a method comprising the steps of: a) Providing a transparent substrate having a top surface; b) depositing a first resist onto the transparent substrate; c) patterning the first resist to produce an array of regions of remaining resist; d) etching to remove regions of the transparent substrate whereby an array of protrusions is formed, whereby the regions of remaining resist are on the tops of the protrusions; e) removing the first resist; f) depositing a metal deposition layer onto the transparent substrate; g) depositing a hard coating layer onto the metal deposition layer; h) polishing the surface of the hard coating layer to expose portions of the transparent substrate corresponding to the tops of the protrusions; i) depositing a metal cladding layer; j) depositing a resist onto the metal cladding layer; and k) patterning the resist and etching the cladding layer to produce an array of apertures on the tops of the protrusions.

An aspect of the invention is a method comprising: a) depositing a sacrificial layer onto the transparent substrate; b) producing an array of nanopillars by selectively etching the sacrificial layer; c) patterning and etching the transparent substrate to form an array of protrusions having tops and sides wherein the nanopillars are disposed upon the tops of the protrusions; d) depositing a metal layer over the structure produces in step c); e) depositing a planarization layer over the metal layer; f) planarizing the planarization layer to expose the metal layer on the tops of the protrusions and to expose the nanopillars; and g) treating the substrate to remove the nanopillars thereby forming an array of apertures on the tops of the protrusions.

In some embodiments the sacrificial layer comprises germanium or silicon. In some embodiments the planarization layer comprises a PECVD oxide or spin-on glass. In some embodiments the planarizing comprises CMP. In some embodiments the metal layer comprises aluminum.

An aspect of the invention is a substrate comprising an array of micromirrors wherein each micromirror comprises a zero-mode-waveguide.

An aspect of the invention is an array of zero-mode-waveguides disposed on a top surface of a transparent substrate having a top surface and a bottom surface, wherein the transparent substrate comprises an array of micromirrors, wherein each micromirror redirects light emanating from the zero-mode-waveguide out of the bottom surface of the transparent substrate.

An aspect of the invention is a micromirror array comprising: a) a transparent substrate having an upper surface comprising an array of features wherein the tops and sides of the features comprise a reflective coating, and b) an array of apertures extending through the reflective coating, wherein the top of each feature comprises at least one aperture, wherein light emitted from the array of apertures is re-directed by the reflective coatings on the walls of the array of.

In some embodiments, the features comprise parabolas, cones, pyramids, truncated cones. In some embodiments, the features comprise truncated cones. In some embodiments, the features comprise truncated cones having tops with diameters between about 0.5 microns and about 5 microns. In some embodiments, the features comprise truncated cones having tops with diameters between about 1.5 microns and about 4 microns. In some embodiments, the features comprise truncated cones having tops with diameters between about 2 microns and about 3 microns. In some embodiments, the features comprise truncated cones having sidewall angles of between 5° and 40° from vertical. In some embodiments, the features comprise truncated cones having sidewall angles of between 10° and 30° from vertical.

An aspect of the invention is a system for measuring molecular events in an array of zero-mode-waveguides comprising: a) an array of zero-mode-waveguides disposed on a top surface of a transparent substrate having a top surface and a bottom surface, wherein the transparent substrate comprises an array of micromirrors that redirect light to the zero-mode-waveguides; b) an illumination system that provides illumination beams to the zero-mode-waveguides through the bottom surface of the transparent substrate; wherein the system is configured such that the micromirrors interact with the illumination beams such that the illumination beams undergo constructive interference, whereby the intensity of light at the zero-mode-waveguide is increased relative to other illuminated regions.

An aspect of the invention is a method for measuring molecular events in an array of zero-mode-waveguides comprising; a) providing an array of zero-mode-waveguides disposed on a top surface of a transparent substrate having a top surface and a bottom surface, wherein the transparent substrate comprises an array of micromirrors that redirect light to the zero-mode-waveguides; and b) illuminating the zero-mode-waveguides through the bottom surface of the transparent substrate with an array of illumination beams; wherein the illumination beams interact with the micromirrors such that the illumination beams undergo constructive interference, whereby the intensity of light at the zero-mode-waveguide is increased relative to its intensity without the constructive interference.

An aspect of the invention is a method for analyzing a property of a single molecule comprising: a) disposing a single molecule having optical characteristics within the aperture of a zero-mode-waveguide wherein the zero-mode waveguide is optically coupled to a micromirror; b) illuminating the zero-mode-waveguide with illumination light; c) collecting emitted light from the zero-mode waveguide with a detector, wherein at least some of the emitted light is redirected by the micromirror to the detector; and d) using the collected emitted light to determine a property of the single molecule.

In some embodiments the zero-mode waveguide and the micromirror are each incorporated into a single substrate. In some embodiments the substrate comprises an array of zero-mode waveguides, each optically coupled to a micromirror.

An aspect of the invention is a method for determining sequence information about a template nucleic acid molecule comprising: a) disposing a polymerase enzyme, a template nucleic acid molecule, and a primer within a zero-mode-waveguide wherein the zero-mode waveguide is incorporated into a substrate also comprising a micromirror, b) providing nucleotides, reagents and cofactors for polymerization, wherein the nucleotides, reagents and cofactors for polymerization are accessible to the polymerase enzyme, wherein at least one of the polymerase enzyme, template nucleic acid molecule, primer, or nucleotides comprise an optical label; c) providing conditions whereby the polymerase enzyme synthesizes a growing nucleic acid strand by incorporating nucleotides; d) illuminating the zero-mode-waveguide with illumination light to interact with the optical label; e) collecting emitted light from the zero-mode waveguide with a detector, wherein at least some of the emitted light is redirected by the micromirror to the detector; and f) using the collected emitted light to determine sequence information about the template nucleotide.

An aspect of the invention is an optical system for observing emitted from a substrate comprising: a) a shaped optical block having a dichroic element embedded therein and at least a first face, a second face, and a third face; b) illumination optics disposed to send illumination light into the optical block through the first face, wherein such illumination light reflects off of the embedded dichroic element, through the second face, and onto a substrate comprising a light emitting element; and c) collection optics disposed to collect light emitted from the light emitting element, wherein the light emitted from the light emitting element passes through the second face, through the dichroic element, out of the third face, and into the collection optics.

In some embodiments the illumination light is internally reflected off of a face of the shaped optical block onto the dichroic element. In some embodiments the light is reflected off of the second face. In some embodiments the first, second, and third faces are substantially planar.

In some embodiments the light emitting element comprises a fluorescent element. In some embodiments the substrate comprises an array of reaction regions, at least some of which comprise a light emitting element. In some embodiments the substrate comprises a ZMW array.

In some embodiments the illumination optics comprise at least one laser and an illumination optical train. In some embodiments the collection optics optical system comprises a collection optics train which passes the emitted light to a detector. In some embodiments the optical block comprises a material having a refractive index of between 1.3 and 2.5. In some embodiments the optical block comprises silicon dioxide or calcium fluoride.

An aspect of the invention is an optical detection system, comprising: a substrate having a plurality of spatially distinct reaction regions disposed thereon; focusing optics positioned between the reaction region and the optical system, for at least partially collimating optical signals from each of the distinct reaction regions; and an optical system positioned for directing excitation illumination to and receiving emitted optical signals from the plurality of distinct reaction regions disposed on the substrate.

In some embodiments the focusing optics are integrated into or attached to the substrate. In some embodiments the focusing optics comprise a plurality of reflective optic elements integrated into the substrate, each of the reflective optic elements positioned to at least partially collimate light from a separate distinct reaction region on the substrate. In some embodiments the reflective optics are selected from parabolic mirrors, conical mirrors, staged conical mirrors, truncated conical mirrors, partial parabolic mirrors, trapezoidal mirrors, and pyramidal mirrors. In some embodiments the focusing optics comprise a plurality of lens elements integrated into or attached to the substrate, each of the plurality of lens elements positioned to at least partially collimate light from a separate distinct reaction region on the substrate.

In some embodiments the plurality of spatially distinct reaction regions is disposed on the surface of the substrate at a density of at least 100,000 distinct reaction regions per cm2. In some embodiments the optical system is configured to direct excitation illumination to and separately receive optical signals from at least 10,000 distinct reaction regions on the substrate. In some embodiments the optical system is configured to direct excitation illumination to and separately receive optical signals from at least 50,000 distinct reaction regions on the substrate. In some embodiments the optical system is configured to direct excitation illumination to and separately receive optical signals from at least 100,000 distinct reaction regions on the substrate.

In some embodiments the optical system comprises an objective lens positioned to collect optical signals from the distinct reaction regions on the substrate, and a dichroic mirror positioned between the substrate and the objective lens, the dichroic mirror being transmissive to optical signals from the substrate and reflective of excitation illumination, such that excitation illumination is not substantially transmitted through the objective lens.

An aspect of the invention is a method of analyzing a plurality of discrete reaction regions on a substrate, comprising: providing a substrate having a plurality of distinct reaction regions thereon; providing focusing optics integrated into or attached to the substrate, the focusing optics separately at least partially collimating optical signals from each of the distinct reaction regions; illuminating the plurality of distinct reaction regions to generate optical signals associated with a reaction in said reaction regions; and transmitting the optical signals collimated by the focusing optics to a detector to detect the signals.

An aspect of the invention is an analytical system, comprising: a substrate having a plurality of spatially discrete reaction regions disposed thereon; a source of excitation illumination; an optical detector array; an optical train, comprising: a multiplexed illumination path that comprises multiplex optics that convert a beam of light from the source of excitation illumination into a plurality of illumination spots, and switching optics for alternately directing the illumination spots at a first portion of the plurality of signal sources and at least a second portion of the plurality of reaction regions; and a signal collection path for collecting signals emitted from the plurality of reaction regions, and directing the signals to spatially discrete locations on the optical detector array.

An aspect of the invention is an analytical system, comprising: a substrate having a plurality of spatially discrete reaction regions disposed thereon; a source of excitation illumination; an optical detector array; and an optical train, comprising: a multiplexed illumination path that comprises multiplex optics that convert a beam of light from the source of excitation illumination into a plurality of illumination spots, and direct the illumination spots at the plurality of reaction regions; and a signal collection path for collecting signals emitted from the plurality of reaction regions, wherein the signal collection path comprises switching optics for directing signals from a first portion of the reaction regions to a first portion of spatially discrete locations on the optical detector array, and directing signals from a second portion of reaction regions to a second portion of spatially discrete regions on the detector array.

An aspect of the invention is a system for the analysis of highly multiplexed reaction regions on a substrate, comprising: a substrate having a plurality of discrete reaction regions thereon; a detection system for detecting optical signals associated with the discrete reaction regions, comprising: at least first and second detectors; and an optical train configured to direct optical signals associated with a first set of discrete reaction regions on the substrate to a first detector, and optical signals associated with a second set of discrete reaction regions on the substrate to the second detector.

An aspect of the invention is a method of analyzing a reaction of interest from a plurality of discrete reaction regions on a substrate, comprising: providing a substrate having a first set of reaction regions disposed thereon; identifying a subset of reaction regions that is fewer than all the first set of reaction regions, that demonstrate the reaction of interest; monitoring the reaction of interest only in the subset of reaction regions.

BRIEF DESCRIPTION OF THE DRAWINGS

FIG. 2 schematically illustrates alternate illumination strategies for monitoring discrete illuminated reaction regions on a substrate.

FIG. 5C, schematically illustrates a structure having a reaction region extending into the micromirror, and illustrates the incorporation of an optical component such as a filter into the micromirror structure.

DETAILED DESCRIPTION OF THE INVENTION

I. Multiplexed Analytical Systems

Figure 1A:
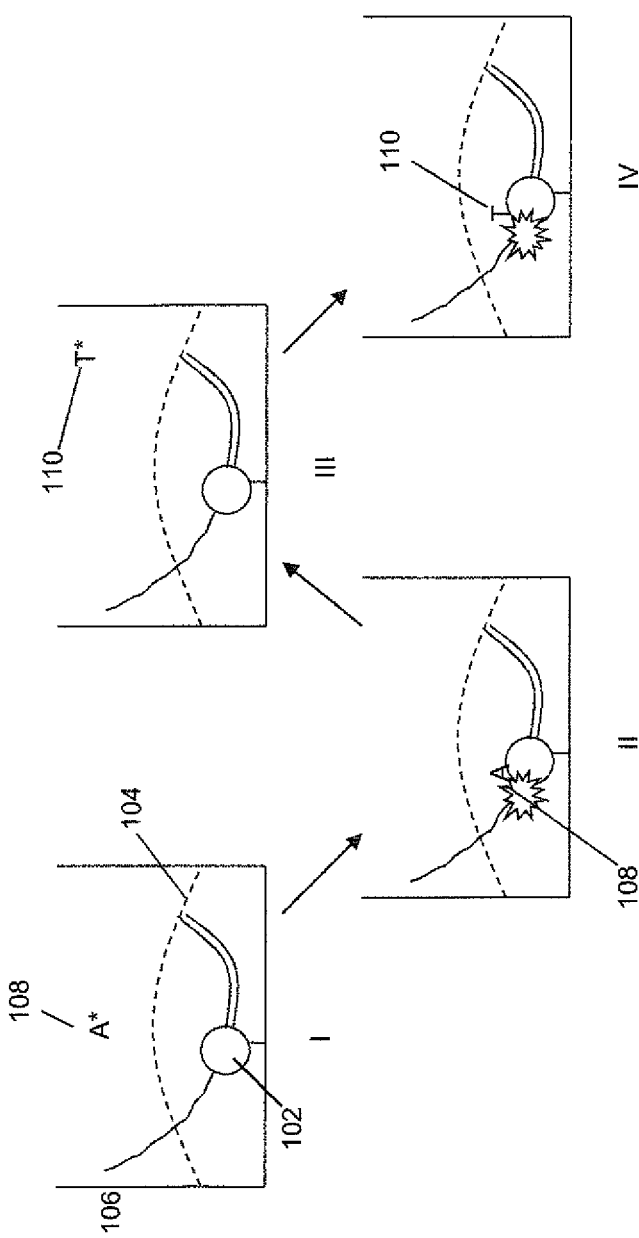
FIG. 1A-B schematically illustrates an exemplary nucleic acid sequencing process that can be carried out using aspects of the invention.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the systems of the invention are of broader application.

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

Figure 1B:
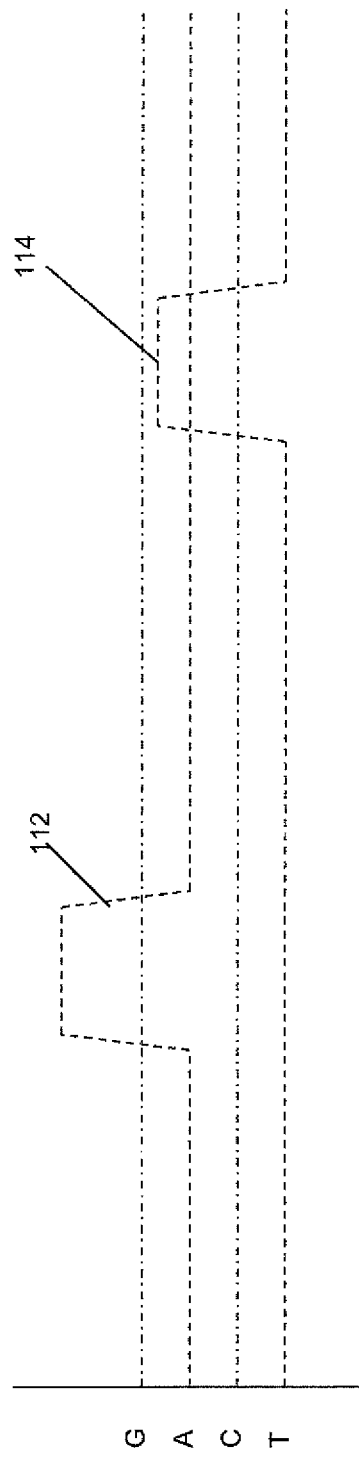

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase mediated template dependent primer extension reaction is monitored as it occurs. In preferred aspects, the template/polymerase primer complex is provided, typically immobilized, within an optically confined region, such as a zero mode waveguide, or proximal to the surface of a transparent substrate, optical waveguide, or the like (see e.g., U.S. Pat. Nos. 6,917,726, and 7,170,050 and Published U.S. Patent Application No. 2007-0134128, the full disclosures of which are hereby incorporated herein by reference in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. A schematic illustration of this sequencing process is shown in FIG. 1. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation which produces a signal associated with that retention, e.g., signal pulse 112 as shown by the A trace in FIG. 1B. Once incorporated, the label that attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, one can obtain long stretches of sequence information of the template. Further, in order to obtain the volumes of sequence information that may be desired for the widespread application of genetic sequencing, e.g., in research and diagnostics, higher throughput systems are desired.

By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments. In preferred aspects, the various different complexes are provided arrayed upon a substrate. Such arrayed complexes may be provided within optically or structurally confined structures, e.g., zero mode waveguides, or they may be patterned on a surface. Alternatively, they may be randomly disposed over a surface but subjected to targeted arrayed illumination, or detection, such that only complexes within an array pattern on the surface are monitored. For purposes of discussion herein, both configurations are referred to herein as the monitoring of arrayed complexes, or the like.

Generally

Figure 2A:
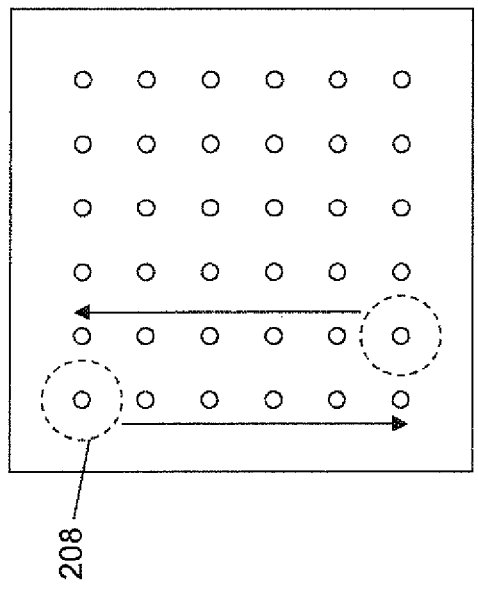
FIG. 2A schematically illustrates a flood illumination pattern.

Multiplexed analysis of discrete reaction regions, and even simultaneous multiplexed analysis, has been accomplished previously using a number of different mechanisms. A number of such methods are illustrated in FIG. 2. For example, in a simple implementation, an array of discrete reaction regions is simultaneously illuminated with a wide illumination beam that covers a large number of such discrete regions, in what is termed "flood" illumination. This is illustrated in FIG. 2A, where the solid circles 204 indicate reaction zones or other regions disposed on a substrate 202, which are desired to be monitored, and the dashed line 206 illustrates the boundary of the illumination region. As shown, a single illumination region is applied over a large number or potentially all of the discrete reaction regions without discrimination.

Depending upon the density of reaction regions on a given substrate, such flood illumination may comprise the use of a conventional laser beam or in some cases may employ beam expansion optics, in order to provide for the desired multiplex, by illuminating larger numbers of reaction regions with a single unified beam or spot. While effective at providing illumination over wide areas of a substrate upon which numbers of reaction regions are disposed, flood illumination can suffer from problems of inconsistent illumination intensity across the illuminated area. In particular, illumination intensity will tend to be greater at the center of a given beam, and drop off at the edges. Accordingly, different reaction regions will typically be subjected to differing illumination depending upon where in the illumination spot they fall. In addition, because the entire substrate area corresponding to the spot is illuminated, it can result in an inefficient use of applied radiation, e.g., wasted light that illuminates non-reaction regions thus requiring greater applied radiation than is necessary. Further, such flood illumination can present adverse effects of excess illumination, such as excess power consumption, reflected excitation light, autofluorescence of substrates as well as other optical components of the system, heating, and the like.

Figure 2B:
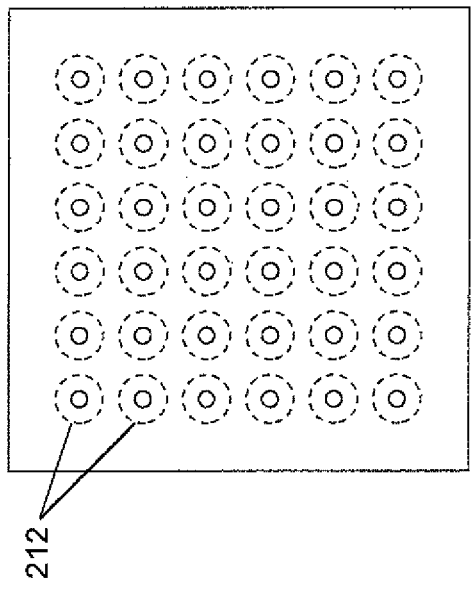
FIG. 2B schematically illustrates a scanning approach to illumination.

In other methods, an illumination beam is scanned across a substrate in order to illuminate multiple reaction sites or regions on the substrate, as shown in FIG. 2B. In particular, a relatively small illumination spot 208, is iteratively moved across the surface of the substrate 202, as shown by the arrows, to separately illuminate each of the reaction regions, e.g., regions 204. Typically, such scanning systems employ conventional scanning systems, such as galvanometers, rotating mirrors or rotating prisms to direct the beam across the surface of a substrate over time. While such scanning systems are particularly effective for static systems, e.g., where one is seeking analysis of an endpoint of a reaction, except in the case of extremely slow reactions, they are not particularly useful in monitoring reaction progress over time. In particular, because the illumination beam only visits each location occasionally and for a relatively short period of time, it is not capable of illuminating and monitoring a reaction region in which reasonably fast reactions occur, in real time.

Figure 2C:
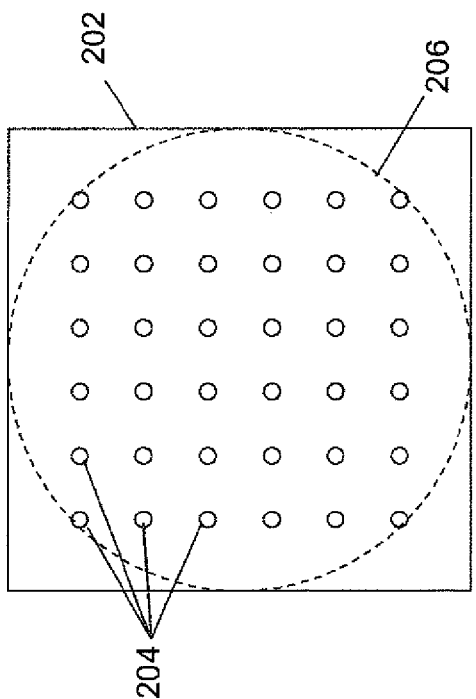
FIG. 2C schematically illustrates a linear illumination pattern.

In other methods, a targeted illumination profile is used to preferentially illuminate multiple reaction sites simultaneously. For example, in one targeted illumination approach, an illumination beam is linearized to provide an illumination line that is capable of illuminating a number of discrete, co-linear regions on a substrate, simultaneously (See, e.g., International Patent Application Nos. US2007/003570 and US2007/003804, which are incorporated herein by reference in their entirety for all purposes), the full disclosures of which are incorporated herein by reference in their entirety for all purposes), as shown in FIG. 2C. By using multiple beams, or splitting a single beam before or after linearization, e.g., by passing the beam through a diffraction grating, one can create a number of parallel illumination lines, e.g., illumination line 210, in order to illuminate multiple rows of collinear reaction regions on a substrate. Such targeted illumination reduces the wasted illumination by not illuminating the space on the substrate between the illumination lines, and consequently reduces many of the issues associated with such excess illumination, as discussed previously. However, space between co-linear reaction regions, e.g., within a given row, is still illuminated, with the accompanying issues of wasted illumination and increased noise that results.

Figure 2D:
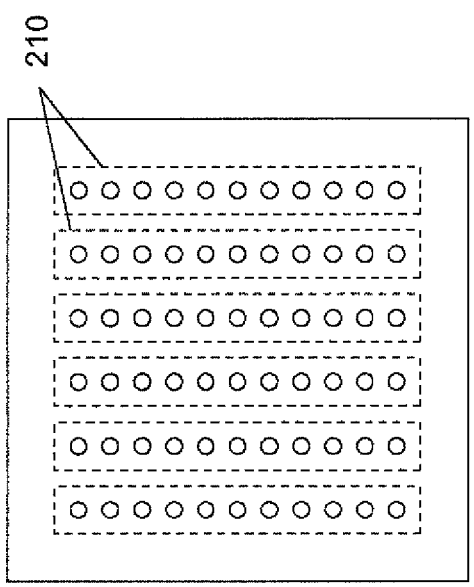
FIG. 2D schematically illustrates a targeted spot array illumination pattern.

In further refinements, targeted illumination profiles use arrayed illumination spots, e.g., illumination spots 212 that each illuminate a subset or a single discrete reaction region, as shown in FIG. 2D. This further enhances the signal to noise ratio, and increases illumination efficiency over linear illumination profiles, by only illuminating the spaces where illumination is desired, e.g., at and/or around the reaction regions. A number of optical configurations may be used to create these types of targeted illumination profiles, including, e.g., the use of lens arrays that focus individual illumination beams into multiple arrayed illumination spots, orthogonally oriented diffraction gratings that first split a single beam into a row of multiple beams, then split each of these beams into an orthogonally oriented row of additional beams, diffractive optical elements that convert a single beam into any of a variety of different targeted illumination profiles, including e.g., gridded arrays of illumination spots on a substrate (See, e.g., U.S. patent application Ser. No. 12/151,979, filed May $9^{th}$, 2008, and PCT/US2008/05953, each of which are hereby incorporated herein by reference in its entirety for all purposes).

Such systems optionally additionally include confocal or spatial filters within the optical train to further limit the impact of reflected or fluoresced light that is out of the focal plane of the system, e.g., that is not associated with the reaction regions.

Figure 3:
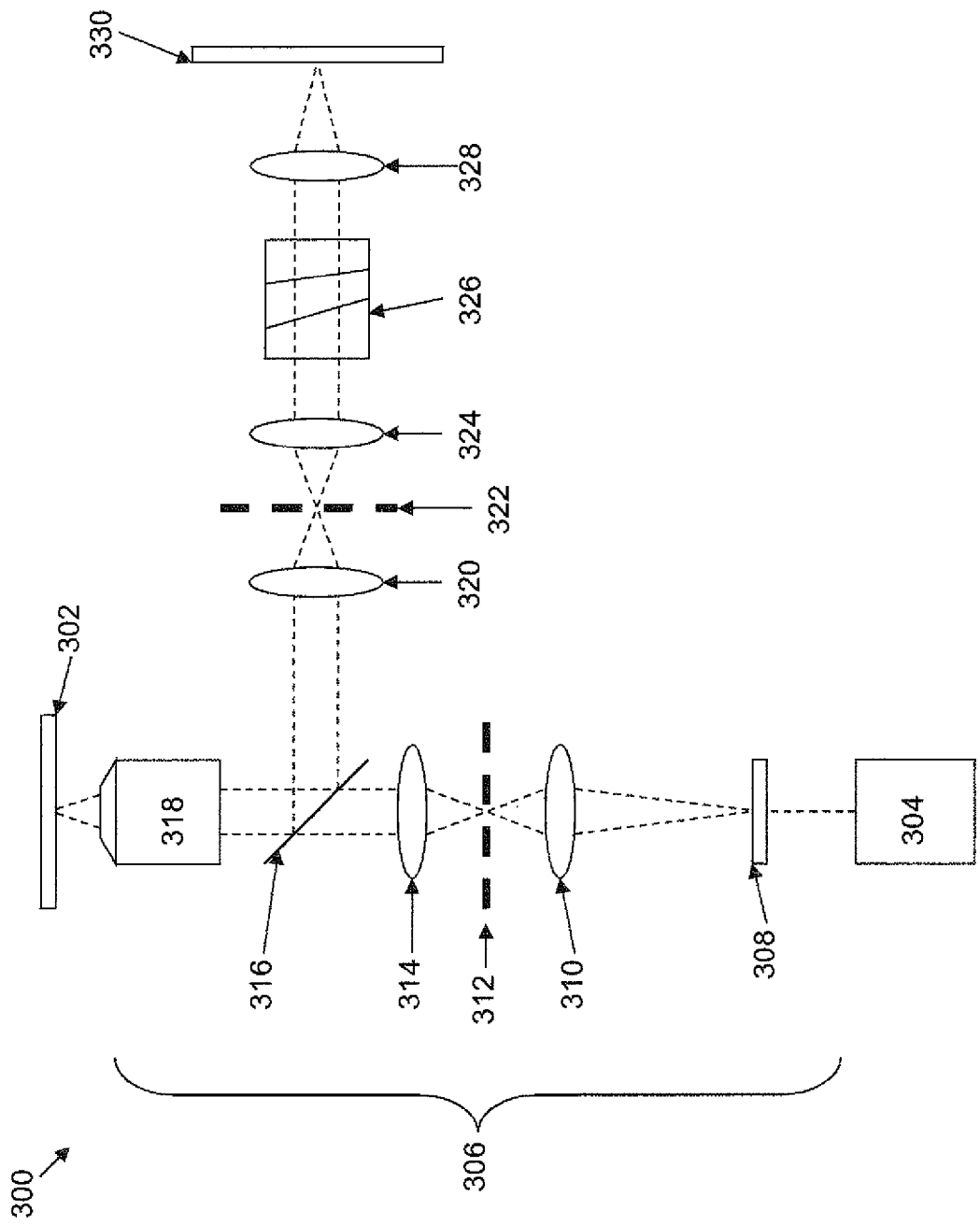
FIG. 3 schematically illustrates a system for carrying out confocal multiplex illumination and monitoring of discrete reaction regions on a substrate.

One example of such system is illustrated in FIG. 3. As shown, the system 300, includes a reaction array, such as a zero-mode waveguide array 302 upon which a number of discrete reaction regions are arrayed. In the case of a zero mode waveguide array, large numbers of zero mode waveguides are typically provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotides or nucleotide analogs required for primer extension are provided with the ZMW (See, e.g., FIG. 1). ZMW arrays can be fabricated at ultra high density, providing anywhere from 1000 ZMWs per $cm^2$, to 1,000,000 ZMWs per $cm^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

As shown, the system includes a source of excitation radiation for exciting fluorescent reactants in the reaction regions, such as laser 304. An optical train 306 delivers excitation radiation from laser 304 to the ZMW array or substrate 302. The optical train also collects fluorescent signals from the various ZMWs on the array, and conveys those signals to a detector, such as EMCCD 330. The optical train 306 includes a multiplex component, such as diffractive optical element (DOE) 308 (also referred to as a holographic optical element or HOE), that converts a single excitation beam to large number of discrete excitation beams that will be targeted in an array of illumination spots that correspond to the location of the ZMWs on the array 302. The multiple beams are dichroic 316 that is selected to pass excitation light and reflect the fluorescence from the array 302. Prior to passing through the dichroic 316, the illumination beams may be passed through a confocal filter 312 which may have associated with it a pair of focusing lenses, e.g., lenses 310 and 314, in order to focus these beams through the confocal pinhole(s). The excitation light that is passed through dichroic 316 is then focused in a targeted pattern onto the plane of the array 302 via objective lens 318.

Fluorescent signals from array 302 are then collected by the objective lens 318, and passed to dichroic 316, which reflects the fluorescent signals toward detector 330. The signals from the discrete ZMWs on the array are then passed through a spatial filter, such as confocal mask 322, to reduce background noise, such as photoluminescence, out of focal plane autofluorescence or scattered light, which again typically has associated with it a pair of focusing lenses, e.g., lenses 320 and 324. The signals are then passed through a dispersive optical element, such as wedge prism 326, that differentially directs light of differing spectral characteristics, allowing for distinction of different fluorescent signals based upon the location upon the detector, upon which they impinge. The differentially directed signal components are then directed through additional focusing optics, e.g., focusing lens 328, and ultimately impact the EMCCD detector 330. As noted, the position on the detector upon which a given signal is incident is indicative of (1) the originating ZMW in the array, and (2) the spectral characteristics of the signal component, which is used, for example, to identify the type of fluorescently labeled nucleotide analog incorporated in an extension reaction.

Using the foregoing systems, simultaneous targeted illumination of thousands or tens of thousands of ZMWs in an array has been described. However, as the desire for multiplex increases, the density of ZMWs on an array, and the ability to provide targeted illumination of such arrays, increases in difficulty, as issues of ZMW cross-talk (signals from neighboring ZMWs contaminating each other as they exit the array), decreased signal:noise ratios arising from higher levels of denser illumination, and the like, increase.

II. Multiplex Approaches

While the foregoing systems are useful in providing efficient multiplexed optical systems, it would nonetheless be desirable to be able to further increase the multiplex capability of these systems by incorporating certain improvements to the systems.

The present invention provides methods, systems and components for monitoring increased numbers of arrayed complexes on substrates. By way of example, U.S. patent application Ser. No. 12/151,979, filed May 9$^{th}$, 2008, and PCT/US2008/05953 (previously incorporated herein) describes methods of analyzing large numbers of arrayed reaction regions, e.g., nucleic acid sequencing complexes, using multiplex optics that direct targeted illumination spots to and collect optical signals from discrete reaction regions. As noted, these systems optionally also include confocal masks, for the enhancement of the signal to noise ratio from such detection The systems of the invention serve to further enhance multiplex of the overall systems through a variety of avenues.

Thus, while the systems of the invention may be used to provide a multiplex analysis of 10, 100, 1000, 5000 or the like discrete reaction regions on a substrate, in particularly preferred aspects, the invention will be employed to provide multiplex analysis of greater than 5000 discrete reaction regions, greater than 10,000 discrete reaction regions, greater than 20,000 discrete reaction regions, greater than 50,000 discrete reaction regions, and even greater than 100,000 discrete reaction regions, and up to 1,000,000 or more discrete reaction regions. In addition to the shear number of reaction regions analyzable by the systems of the invention, it will be appreciated that in some cases, such reaction regions can be disposed at higher densities than previously employed, through the various advantages provided by the invention. For example, discrete reaction regions can be provided and observed at high densities without excessive interference or other problematic issues. Such densities can be, e.g., 1000, 10,000, 100,000, 1,000,000, 10,000,000, or more reaction regions per $cm^2$. Density of observation volumes can be increased up to the diffraction limit of the observation light used, which can be as low as 250 nm for some of the wavelengths contemplated in these applications. At this spacing up to 16e9 observations volumes per square centimeter could be visualized in a square array, slightly more for a hexagonal close-packed array. The diffraction limit could be exceeded through the use of near-field optics, leading to a limitation governed only by the physical size of the confinements, which can be as small as 50 nm in size. Separated by 100 nm in a square array, this leads to a density of 1e10 per square centimeter.

Further, such multiplex analysis will be substantially simultaneous with respect to the number of regions being monitored.

By "substantially simultaneous", is meant that within the timeframe of 1 to 5 (preferably 1 to 2) camera frames, the requisite number of regions has been analyzed. For purposes of the systems of the invention, a camera frame is typically captured from about every 1 ms to about every 10 ms (or frame rates of from about 100 Hz to about 1000 Hz), so that to be within the range of a substantially simultaneous analysis, analysis of such multiplex regions shall occur within a time span of from about 1 ms to about 10 ms. As a result, a system that provides the desired multiplex analysis, e.g., observing multiple locations at least once each within a window of from 1 ms to about 10 ms, will be said to be substantially simultaneous, even if the analyses are carried out at two distinct time points within that window.

Ins some cases, slower frame rates may be employed, which would increase the time period in which two events may occur while still appearing to be substantially simultaneous from the perspective of the camera. For example frame rates of 10 Hz to 100 Hz, 10 Hz to 50 Hz, 10 Hz to 20 Hz, e.g., approximately 15 Hz, may be employed. As will be appreciated, sampling rates that occur on the millisecond range may be viewed as being substantially simultaneous, e.g., from 1 ms to about 500 ms, 10 ms to about 100 ms, or the like.

A. Enhanced Efficiency Optics

The ability to substantially increase the multiplex in analysis of discrete reaction regions on substrates faces a number of constraints. By way of example, in systems that monitor fluorescent signals from single molecule reactions, collection optics typically employ high numerical aperture objective lenses that have a relatively small field of view. As such, increased multiplex typically requires closer packing of reaction regions in order to collect signals from larger numbers of those regions using a single objective. However, closer packing of reaction regions on a substrate gives rise to a series of additional resolution issues, including, e.g., cross talk among regions, etc.

Figure 4:
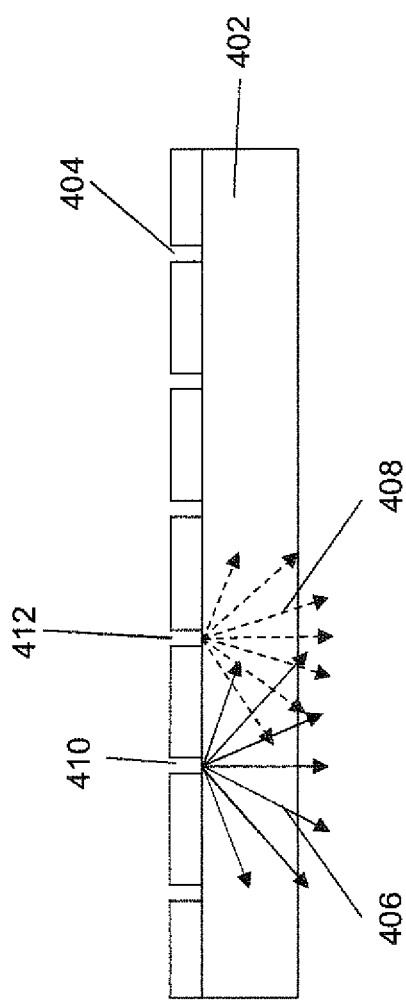
FIG. 4 schematically illustrates potential "cross-talk" issues associated with high multiplex systems.

Optical cross talk is illustrated in FIG. 4. As shown, an array of reaction regions (e.g. 404, 410, and 412) on a substrate 402, such as zero-mode waveguides 404, is provided upon a substrate. A fluorescently monitored reaction occurring in those regions is illuminated and emits a fluorescent signal associated with the reaction. As shown by the solid arrows 406 and dashed arrows 408 from adjacent reaction regions 410 and 412, respectively, the omni-directional emission profile of the signal yields the possibility of signals from adjacent regions interfering with each other, particularly as these regions become more closely packed on the substrate. This "cross-talk" limits the ability to closely pack reaction regions for analysis.

In accordance with certain aspects of the invention, enhanced optical approaches are employed to enhance the efficiency of signal collection.

One such optical approach provides for the addition of focusing optics that serve to minimize optical cross-talk among reaction regions, and also allow for the use, in many applications, of objective lenses that have a larger field of view. By decreasing cross-talk potential one improves the ability to close pack reaction regions. Simultaneously, by moving to a higher field of view objective, one can expand the area in which such regions are disposed. In addition to lowering cross-talk, the focusing optics of the invention can also increase the amount of light that is detected by redirecting light into a detector that would otherwise not be detected by the detector without redirection. By redirecting the light, a detection system can be used which, for example collects the same amount of light as without redirection, but has a lower numerical aperture, allowing, for example, a larger field of view. In the context of methods contemplated in this invention, having a large field of view can be important, for example, for allowing the simultaneous observation of tens of thousands of luminescing or fluorescing regions at once. Alternatively, by directing the light, the same numerical aperture can be used, while collecting more light. As described in more detail below, the focusing optics of the invention can also provide for increased levels of illumination by directing illumination light into a reaction region on an array, such as an array of zero-mode waveguides.

Micromirror Arrays

In one aspect the invention provides an array of shaped micromirrors wherein each micromirror is associated with an optical confinement, and in particular an array of shaped micromirrors that is incorporated into the same substrate that comprises the optical confinements.

Figure 5A:
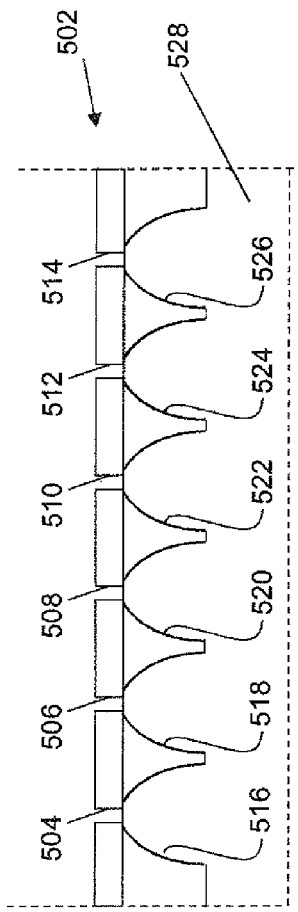
FIGS. 5A, 5B and 5C schematically illustrates a substrate employing shaped mirrors as focusing optics for efficient light collection from reaction regions on the substrate and for efficient illumination of the reaction regions.

An example of an array of shaped micromirrors in accordance with the invention is illustrated in FIG. 5A. As shown, the overall substrate 502 includes an array of reaction regions, such as zero-mode waveguides 504-514, disposed upon its surface. Conical or parabolic mirrors 516-526 are integrated into the underlying transparent substrate 528, and are configured to redirect or to focus both the incoming and outgoing light to and from the ZMWs in the array. In particular, the conical or parabolic mirrors are typically comprised of a reflective material, such as a metal layer, e.g., aluminum, silver, gold, chrome, or the like, manufactured into the underlying substrate to provide the mirror surfaces.

Figure 5B:
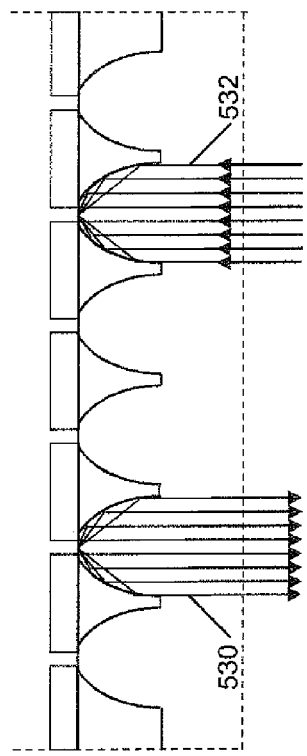

As shown in FIG. 5B, fluorescent signals 530 emitted from the reactions within the ZMWs are redirected or focused by a mirror such as a parabolic or conical mirror increasing the efficiency with which such signals are collected. As shown here, for example omni-directional emitted light coming into the reaction regions on the substrate is redirected such that it is more readily detected. In some cases, as illustrated here, the light can be at least partially collimated. In addition, for each reaction region or ZMW, the mirror structure reduces or eliminates inter-ZMW cross-talk within the substrate itself. In addition to the reduction in cross-talk, it will be appreciated that the enhanced collection efficiency resulting from redirection or focusing of the emitted light also increases the sensitivity of the system. Likewise, the shaped optic elements will also serve to focus incoming illumination, e.g., light 532, onto the reaction regions such as ZMWs 504-514.

Figure 5C:
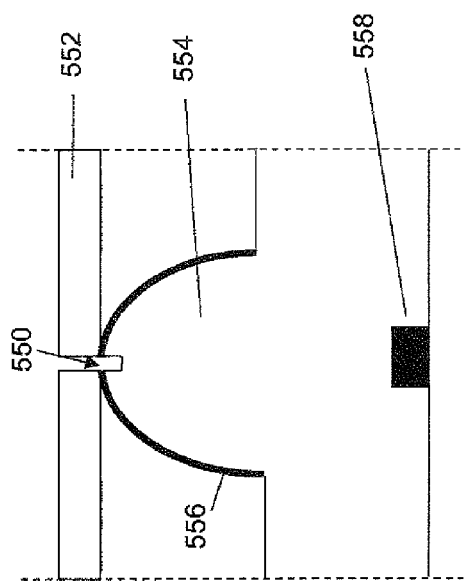

Alternative configurations may also be adopted for the devices incorporating these conical mirrors. For example, a zero mode waveguide core region may be extended into the underlying substrate. This example is illustrated in FIG. 5C, in which the reaction region 550 extends beyond cladding layer 552, and into the underlying substrate 554, allowing in some cases for more efficient signal transfer to and from the reaction region 550, that is reflected off of mirror 556. Optional components such as light blocking regions or filter components may be additionally included within the overall structure, including, for example, mask 558, to further enhance the optical properties of the mirror system.

Although the mirrors described herein are referred to as "conical" or as "parabolic" mirrors, it will be understood that such integrated reflective focusing optics components will be characterized by their ability to provide a reflective component within the substrate that enhances the detection of light by redirecting the light emitted from the reaction region through the substrate, irrespective of its precise shape. In some cases, the light emitted from the reaction region is at least partially collimated. The shaped mirrors of the invention will thus redirect light from an optical confinement on the substrate to a detector, or to an optical element that is part of an optical train bringing light from the substrate to a detector. The focusing mirrors may comprise shapes other than parabolic structures, such as conical mirror configurations, staged conical mirror configurations, truncated conical mirror configurations, partial parabolic mirror configurations, trapezoidal mirror configurations, pyramidal mirror configurations, and the like, provided such structures redirect the light, for example to enhance the detection of light emanating from or through the reaction region into the substrate, for example by partial collimation. In many cases, the mirrors will have a cylindrical symmetry. The shape of the mirror can be a prismatoid, for example, a pyramid, wedge, prism, antiprism, cupola, or frusta thereof. Where the mirror has multiple sides, such as where it comprises a pyramid or a frusta of a pyramid, the mirror can have any suitable number of sides. For example, where the mirror comprises a pyramid, the pyramid can have 3, 4, 5, 6, 7, 8, 9, 10, 11, 12, or more sides.

The shaped mirrors of the invention are generally micromirrors, meaning that the mirrors are small, generally having dimensions on the order of microns or tens of microns. In some cases the term microreflector is also used to refer to a micromirror. The mirrors can have a cross-sectional dimension from about 0.1 micron to about 100 microns, about 1 micron to about 50 microns, or about 2 microns to about 20 microns. While the mirrors of the invention have dimensions on the order of microns to tens of microns, in some cases, the shaped mirrors of the invention can be larger, for example from about 100 microns to about 1 mm or greater.

Further, although described in terms of providing a reflective material such as a metal layer within the substrate itself, it will be appreciated that other reflective configurations may be likewise employed without the use of a metal layer. For example, structures may be comprised of materials of differing refractive indices to provide for a reflective interface that performs the same function as the metal layers described elsewhere herein. For example, light that is traveling from a region of one refractive index across an interface into a region of a lower refractive index will generally be completely internally reflected if the angle of incidence of the light is greater than a give value (the critical angle). In this manner, reflective structures of the invention may be created without the use of a reflective layer by appropriately adjusting the refractive indices of the materials on either side of the shape.

Figure 6:
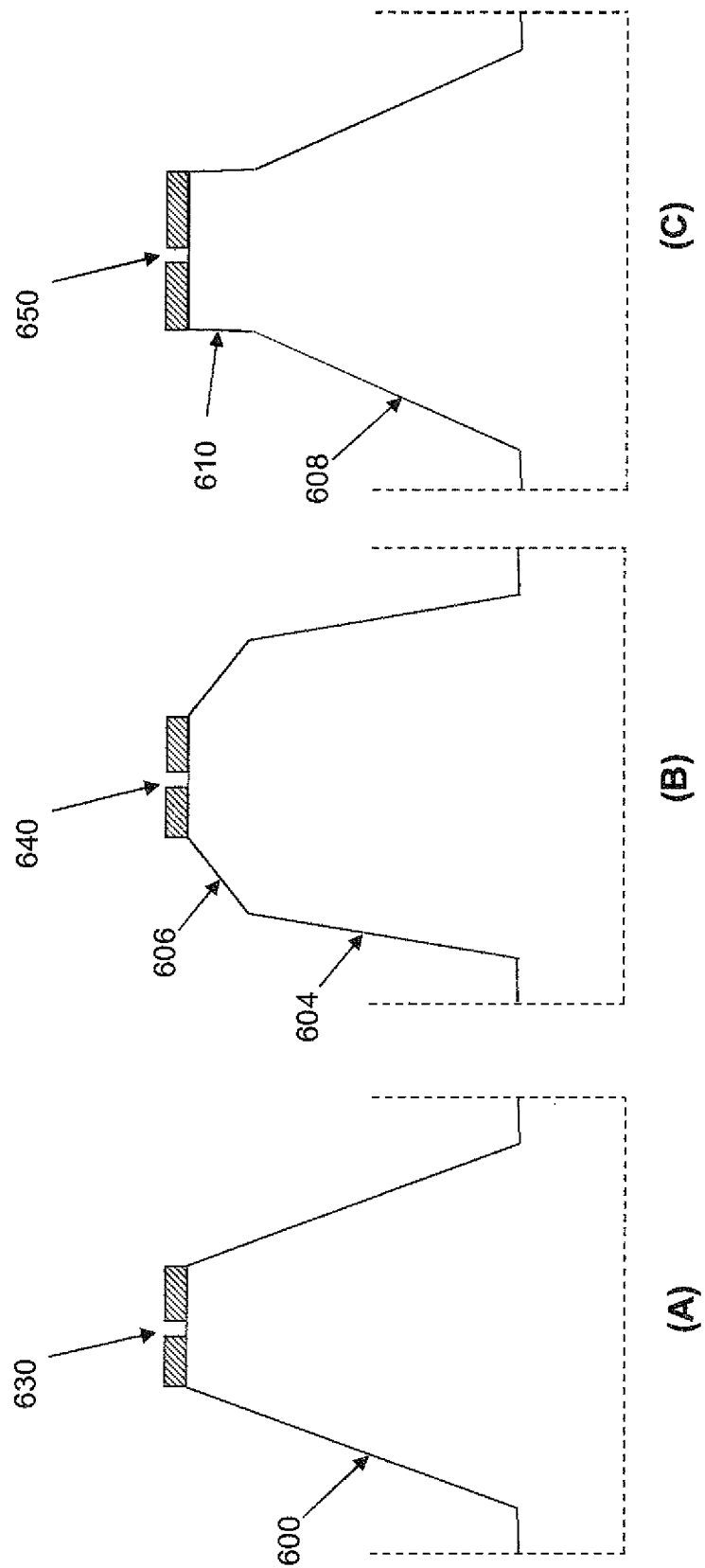
FIGS. 6A, 6B, and 6C schematically illustrate three alternate conical microreflector (micromirror) structures.

In some cases, the shaped reflective structures of the invention comprise conical reflectors. The efficiencies in a conical reflector scheme show substantial improvements over non-reflector substrates both in theoretical models and experimentally. In some cases, conical structures are useful as they can be readily formed by a variety of processes. For example, the tapering of the walls can be controlled by controlling the geometry of the resist, and by the lithography conditions. The resist geometry can be controlled, for example, by controlling the focus/exposure conditions of the resist to control the topology of the resist, or by gray-scale lithography. The shape can also be controlled by controlling the etching conditions, for example, controlling the amount of surface passivation or by gray-scale etching. The conical mirror substrates of the invention generally comprise a truncated cone structure. The walls in the truncated cone section of the conical mirror substrates can be straight, or can include some curvature. Examples of three conical structures are illustrated in FIG. 6. FIG. 6A shows a conical mirror structure where the structure of the mirror is a truncated cone comprised of a straight sided conical structure 600, which is disposed in the substrate layer below a reaction region or reaction zone, such as zero-mode waveguide 630 in order to provide redirection of light into or out of the reaction region. FIG. 6B shows a staged conical structure having a lower conical section 604, and an upper conical section 606. Upon this structure is disposed a reaction region 640. In this embodiment the lower conical section 604 has side walls having a first angle with respect to the normal to the substrate, and the an upper conical section 606 having side walls with a second angle with respect to the normal to the substrate where the second angle is greater than the first angle. In some cases, the walls of the upper section will have an angle to the normal which is lower than that for the lower section. As shown in FIG. 6C, the conical structure can have a lower truncated cone section 608, and an upper cylindrical section 610 with walls normal to the substrate. Upon this structure is disposed a reaction region 650. Structures having the profile of FIG. 6C can be useful for producing arrays having high density. For example, a structure having a cylindrical top portion and a conical lower portion will generally have smaller base dimensions than a simple truncated conical structure having the same side wall angles. In some cases, more structures can be packed into a given area if the structures have smaller base dimensions. The reflective structures shown in FIG. 6 are shown as protruding from a base transparent layer. This base transparent layer can be a planar substrate such as a fused silica wafer having protrusions disposed on its upper surface. The structures of FIG. 6 will generally have a reflective coating or a reflective region adjacent to the walls of the structures to enhance the internal reflection of light. The reflective surface of the shaped substrate can be provided, for example, by coating the protrusion with a reflective layer, by filling the region between protrusions with reflective material, or by using a lower refractive index medium outside of the protrusion to encourage internal reflection.

While the illustrations of FIG. 6 indicate that the reactive region is in the center of the top of the conical structure, in some cases, the reactive region may not be directly in the center. Manufacturing tolerances may result in the reactive region being off of the central position. In addition, in some cases, the reactive region can be manufactured to be off-center in order, for example to experience higher levels of illumination, or, for example, where the illumination or detection optics are disposed at an angle off of the normal from the particular reaction region.

The micromirror arrays can be fabricated at a high density as described above for ZMW arrays. The density of micromirrors associated with reactive regions can be, for example, anywhere from 1000 ZMWs per $cm^2$, to 1,000,000 ZMWs per $cm^2$, or more. At any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate using the micromirror arrays described herein.

Figure 7:
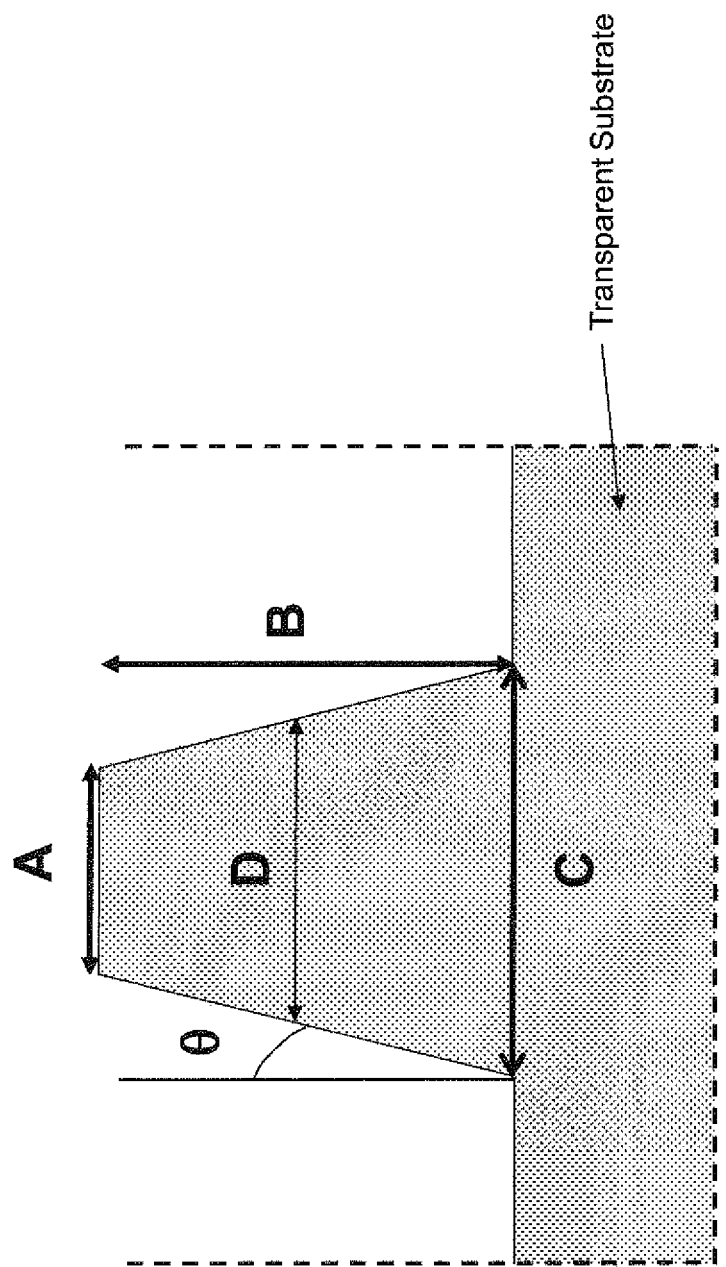
FIG. 7 schematically illustrates a truncated conical micromirror structure having specific dimensions.

FIG. 7 shows a conical structure for a micromirror of the invention. The truncated cone structure as shown in FIG. 7 constitutes a protrusion extending above a transparent substrate. The truncated cone can be a cylindrically symmetrical, having a substantially circular top surface with a diameter A, a substantially circular base having a diameter C, and a diameter at half height of D. The truncated cone has a height, B. The walls of the truncated cone are substantially straight having an angle with respect to the normal of the surface of theta ($\theta$). The side walls of the truncated cone structure shown here are substantially straight, but the walls can deviate from being straight and still function to redirect the light intensity as described herein. In some cases, the methods of producing the conical structure will result in walls that vary from being straight, for example, having curved profiles. In other cases, walls that deviate from being straight are incorporated to improve collection efficiency. In many cases, the process that produces the protrusions will result in surfaces with bumps, ridges, or other imperfections on the side walls which deviate from that of a straight profile. In some cases, having a straight profile is desirable for increasing the density of reactive regions on a substrate. For example, a curved wall, such as a parabola may have a larger base diameter than that of a straight-sided cone. By using the structure with the smaller base diameter, higher packing densities can, in some cases, be achieved.

Exemplary conical structures of the invention having the profile shown in FIG. 7 have a top diameter A of between about 0.1 micron and 100 microns, for example between 1 micron and 20 microns, or between 2 microns and 10 microns. In some cases, the diameter of the top of the truncated cone A is between about 1 micron and about 5 microns. In some cases, the diameter is between 2 microns and 4 microns. Exemplary conical structures of the invention have a side wall angle theta ($\theta$) of between about 2° and 45°, between about 5° and 35°, between about 10° and 30°, or between about 14° to about 26°. The conical structures are produced to redirect light emitted by the reactive regions, for example, at the center of the top of the conical structure. Exemplary structures will at least re-direct light emitted from the reactive region into the conical structure that has an angle of about 22.5° from the normal. In exemplary embodiments of the invention, the height of the conical structure B is between about 0.2 micron and about 100 microns, between about 1 micron and about 10 microns, or about 2 microns to about 8 microns, or about 3 microns to about 6 microns. In some cases, it is desirable to control the ratio of the height of the truncated cone to the diameter of the base (B/C). In exemplary embodiments, the ratio B:C is between about 1:3 and about 3:1, is between about 1:2 and about 2:1, between about 1.5:1 to about 1:1.5, or between about 1.2:1 to about 1:1.2. It will be understood to those in the art that the choice of A, θ, and B will determine the width of the base, C. As described above, in order to increase the density of the optical structures of the invention, it can be desirable to control the parameters such that the width of the base C is small enough to allow the increased density. The diameter of the base C can be between about 0.2 micron and about 100 microns, between about 1 micron and about 10 microns, or about 2 microns to about 8 microns, or about 3 microns to about 6 microns.

An exemplary conical structure of the invention has a top diameter A of between about 1 micron to about 5 microns, a height B of between about 2 microns to about 8 microns, and a sidewall angle between about 10° to about 30°. The exemplary conical structures of the invention will have a reaction region disposed on the top portion of the cone, generally approximately at the center of the top portion. The reaction region can be for example, a zero-mode waveguide comprising an aperture disposed through a reflective cladding layer on the top surface of the conical structure. Such aperture can have a diameter of about 30 nm to about 300 nm.

Figure 8:
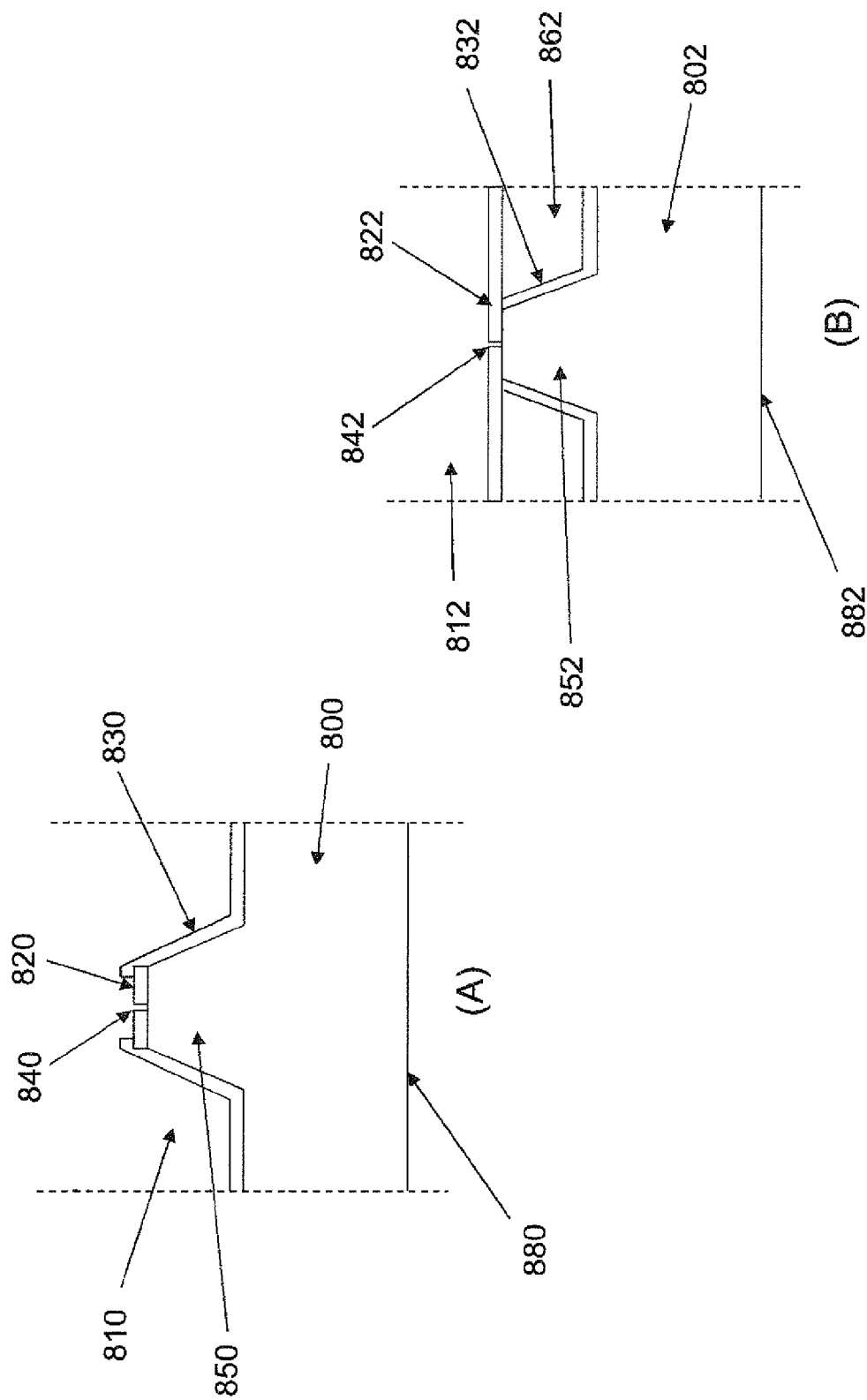
FIG. 8A-B schematically illustrates micromirror structures which can be produced, for example, using methods such as lithography and etching.

FIGS. 8(A) and 8(B) show two exemplary structures for shaped mirrors of the invention. These structures can be produced, for example, by methods developed for microfabrication including semiconductor processing and for creating MEMS devices such as those incorporating photolithography and etching. FIG. 8(A) shows a transparent substrate 800 having a top surface onto which an array of protrusions 850 having reflective coatings 830 on their sidewalls is disposed. The protrusions 850 are shaped micromirrors that will redirect illumination light into reaction region 840, and/or redirecting emitted light from the reaction into detection optics disposed below the bottom surface 880 of the transparent substrate 800. The reaction regions 840 are, for example zero-mode waveguides comprised of nanoscale apertures extending through a cladding layer 820 disposed on top of the micromirror structure. In some cases, the reaction regions 840 will extend into the transparent substrate. A reflective layer 830 is disposed on the outside walls of the micromirror to enhance the reflectivity of the walls. In some cases, the cladding 820 and the reflective layer 830 will be the same material, e.g. aluminum. The region 810 above the transparent surface can contain a liquid medium comprising sample and/or reactants which can diffuse into or out of the reaction region. In some cases, all of the reaction regions in the array will be in contact with the same solution in the region 810. In some cases, barriers are included between reaction regions which will lower or prevent diffusion between reaction regions.

FIG. 8(B) shows an alternative structure for the shaped mirrors of the invention. FIG. 8(B) illustrates the situation where, while the transparent substrate 802 comprises protrusions 852, the overall substrate is substantially planar due to the planarization layer 862. A reaction region 842 is disposed on the top of the protrusion 852, for example as an aperture through a cladding layer 822. A reflective layer 832 may be disposed on the protrusion 852 to improve reflectivity. In some cases, no reflective layer 832 is used, for example where the planarization layer 862 comprises a reflective material. The planarization layer can comprise a hard material, such as an inorganic material, for example a spin-on glass or silicon nitride. The planarization layer can comprise a metallic material such as aluminum. The planarization layer can be a soft material, such as a polymeric material, e.g. an organic polymer such as polyimide or a siloxane based polymer. Sample and reagents can be introduced to the reactive region 842, for example, via a liquid medium in the region above the substrate 812.

The transparent substrate can comprise inorganic materials, organic materials, or composite materials with both organic and inorganic materials. The transparent material is typically a rigid material which can keep the reactive regions in fixed positions during observation. Silica based materials, such fused silica are preferred materials, for example, where semiconductor or MEMS processing methods are used to produce the micromirror arrays. The transparent substrate may also comprise inorganic oxide materials and glasses. The transparent substrate material may be a heterogeneous material, such as a material having multiple layers. In some cases, for example, the transparent substrate may comprise a dielectric stack. Transparent polymeric materials can also be used. It is typically desired that the transparent material exhibit low levels of autofluorecence. Suitable transparent polymers comprise, for example, methacrylate polymers such as PMMA, polycarbonates, cyclic olefin polymers, styrenic polymers, fluorine-containing polymers, polyesters, polyetherketones, polyethersulfones, polyimides or mixtures thereof.

The reflective layer on the outside of the protrusion in the transparent layer can comprise a metallic material such as aluminum, copper, gold, silver, chrome, or mixtures thereof. The reflective layer can also comprise a reflective organic polymer, such as a composite material comprising reflective particles dispersed in a polymeric material.

The cladding layer is an opaque or reflective material. The cladding layer can be a metal such as aluminum, copper, gold, silver, chromium, titanium or mixtures thereof. In some embodiments, the reflective layer and the cladding layer comprise the same material.

The micromirrors of the invention can improve the efficiency of collection of the light from reactive regions on the substrate over the collection efficiencies which would be obtained without the mirror structures. The collection efficiency of an optical system is typically influenced by the numeric aperture of the collection system. The micromirrors of the invention can improve the amount of light collected by a detection system having a given numeric aperture, e.g. a numeric aperture of 0.5, by greater than about 10%, 20%, 30%, 40%, 50%, 75%, 90%, 2 times, 3 times, 5 times, 10 times or more than the amount of light collected without the micromirrors. The numerical aperture of the detection system can be, for example, from 0.1 to 0.9. In some cases the numerical aperture is between about 0.2 and 0.5.

The micromirror structures can also increase the level of illumination of the reaction regions from an illumination source. For example, the level of illumination can be increased by greater than 20%, 30%, 40%, 50%, 75%, 90%, 2 times, 3 times, 5 times, 10 times or more than the level of illumination without the micromirrors.

In one aspect of the invention, the mirror structures are produced such that the illumination light undergoes constructive interference such that light intensity is increased in the reaction region. Light can undergo interference, which is the addition or superposition of two or more light waves that result in a new wave pattern. Interference can occur, for instance, for waves which are correlated or coherent with each other, for example because they come from the same source or because they have the same or nearly the same frequency. For example, for the mirror structures of the invention, incoming light can be redirected from the side walls of the structure such that the light redirected from different portions of the side walls interacts within the mirror volume to either constructively or destructively interfere. Since the redirected light derives from the same source, each redirected portion of light will tend to have substantially the same frequency. Whether the light in a give region will undergo constructive or destructive interference will depend on whether the light is in phase (constructive) or out of phase (destructive). By controlling the geometry of the micromirror structure and the properties of the illumination light, the regions of constructive or destructive interference can be controlled.

Electromagnetic modeling tools, such as finite different time domain (FDTD) or finite element methods (FEM) can be used to determine the areas of constructive interference by inputting the mirror structure and illumination light parameters. We have determined that for a cone structure where the top diameter is similar in diameter to the beam diameter, the field in a localized region, such as the reaction region can be increased on the order of 10 times the intensity without the constructive interference. In some cases, the localized area of high intensity can have dimensions of about 0.25 to about 1 wavelength in size. Having a beam diameter on the same dimensions of the of the micromirror can be advantageous for enhancing the illumination. In some cases, the mirror structure has a top surface, for example, is a truncated cone having a planar top surface, and the top surface has a diameter. In such cases, the ratio of the diameter of the top surface to the beam diameter of the incoming light for these systems is from about 1:5 to about 5:1, from about 1:3 to about 1:3, from about 1:2 to about 2:1 or about 1:1.5 to about 1.5:1.

Figure 9:
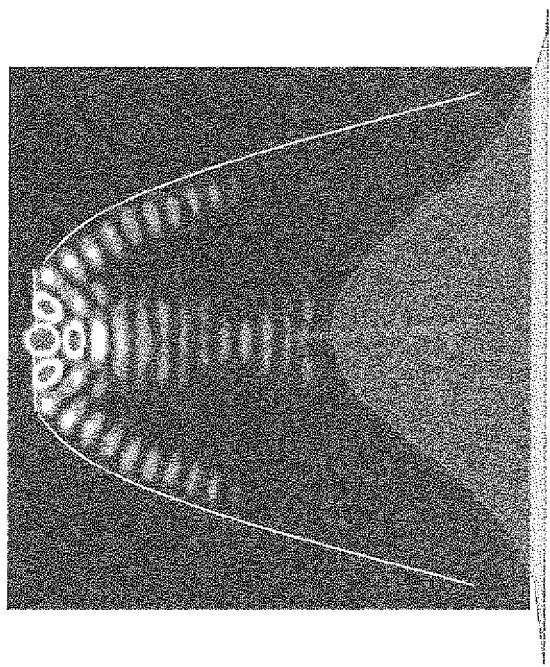
FIG. 9 schematically illustrates how the micromirror structure can enhance illumination light intensity by constructive interference.

FIG. 9 shows an illustration of a micromirror structure being illuminated with collimated light. The different shades in the figure within the micromirror structure represent different light intensities. The figure shows several regions of high intensity near the top of the micromirror, with one region of high intensity occurring at the reaction region located in the center of the top of the mirror structure. By constructing the micromirror structure such that constructive interference occurs at the reaction region, the intensity of light in the reaction region can be increased over what it would have been in the absence of the micromirror. Constructive interference can be used to increase the intensity of light at the reaction regions greater than about 30%, 40%, 50%, 75%, 2 times, 3 times, 5 times, 10 times, 15 times, 20 times, 30 times or more than 30 times the intensity than the intensity would be for the same illumination light without the micromirror structure.

Fabrication of Micromirror Arrays

The micromirror arrays of the invention can be produced by a variety of methods. One aspect of the production of the arrays is the production of an array of structures such as protrusions on a transparent substrate. The array of structures can be produced by molding, stamping, embossing, machining, etching, or other suitable methods.

One preferred approach to producing the micromirror arrays of the present invention involves the use of microfabrication methods such as semiconductor or MEMS processing methods, which have been highly developed for the production, for example, of integrated circuits. Similar processes have been used to create MEMS (micro electromechanical systems) for a variety of applications including inkjet printers, accelerometers, pressure transducers, and displays (such as the digital micromirror displays (DMDs)). Microfabrication methods can be applied to a large substrate such as a wafer, which can later be diced into many devices, allowing for the production of many devices at one time. An aspect of the invention is the use of these processes for producing a micromirror array in a transparent substrate, such as a glass, e.g. fused silica. The methods of the invention apply resist processes, such as photoresists to define structural elements on the transparent substrate or other layers. Etching processes are used to produce three-dimensional structures including the reactive region and the micromirror structure. Deposition processes are used to add layers onto the substrate. Other semiconductor processes such as aching, polishing, release, and liftoff are also employed to create the micromirror structures of the invention as described in more detail below.

The transparent substrate can be any suitable rigid transparent material. The transparent material can comprise, for example, an inorganic oxide material such as silica. A preferred material is fused silica.

One aspect of the invention is a process for producing substrates comprising arrays of reactive regions associated with incorporated micromirror structures by a method comprising the steps of: a) providing a transparent substrate having a top surface; b) patterning and etching the transparent substrate to form an array of protrusions having tops and sides; c) depositing a cladding material such that the tops of the protrusions comprise a cladding; d) forming an array of apertures through the cladding such that the top of each protrusion comprises an aperture; and e) depositing a reflective deposition material such that the sides of the each protrusions comprise a reflective layer; whereby the array of protrusions comprise an array of micromirrors, and the aperture at the top of each protrusion comprises a zero-mode waveguide. The process involves the production of both reactive regions and micromirror structures. One set of processes described herein in greater detail involves first producing the reaction regions, for example, as an array of apertures, and subsequently producing the micromirror structures. Another set of processes involves first producing micromirror structures on the transparent substrate and subsequently producing the reactive regions.

In order to produce the arrays of the invention it can be useful to combine different processes for the different features having different dimensional requirements. For example, the processes of the current invention may use a 193 nm lithography process for producing the reactive regions and I-line lithography for producing the micromirror structures. This is not a typical production process as it can require sending the substrate from one fabrication facility to another fabrication facility in the middle of the process.

FIG. 10 through FIG. 18 illustrate exemplary processes of the invention for production of arrays of reaction regions, each associated with a micromirror optical element within a transparent substrate. These exemplary processes do not provide an exhaustive list of the processes which constitute the present invention. The processes each involve different sets of steps. In some cases, the sets of steps from one process can be combined with sets of steps from another process to produce the substrates of the invention. For example, the steps for production of the micromirror structure in one process may be combined with steps for production of the aperture. In addition, the descriptions provided may not call out all the steps that would be incorporated. For example, in many cases, ashing, cleaning, resist removal, rinsing, and drying steps which are not described herein will in many cases be incorporated into the processes of the invention.

While the steps in the described processes show certain layers directly on top of other layers, where suitable, the processes of the invention include the inclusion of intervening layers between the layers described, but not explicitly called out herein. For example, for many resist processes, a protective layer or an antireflective coating layer such as a BARC is included, for example, between the resist layer and the layer below the resist layer. It is to be understood that such layers can be incorporated within the described processes. Unless specifically described, the order of the steps of the processes described herein can be altered where suitable.

In some cases the methods provide for etching steps which etch several layers, for example through both a metal cladding layer and the transparent substrate, or through all three of a protective layer, a metal cladding layer, and the transparent substrate. While the methods generally shows etching the layers simultaneously, in some eases separate lithography and etching steps are carried out for each layer. For example, where etching is done through a metal layer and the transparent substrate, in some eases, it is desired to first deposit a resist and pattern a first resist to etch the metal layer, and deposit and pattern a second resist to etch the transparent substrate. In some cases, multiple etching steps can be performed in a manner that provides, for example, staged conical structures. For example, a first lithography and etching process can etch the metal layer and extend straight down normal to the surface into the transparent substrate to form a cylindrical structure; and a second lithography and etching process which results in sidewalls at an angle with respect to the normal to the surface will produce a lower conical structure. In this manner, by using multiple etching steps, mirror structures such as that shown in FIG. 6C can be produced.

Figure 10:
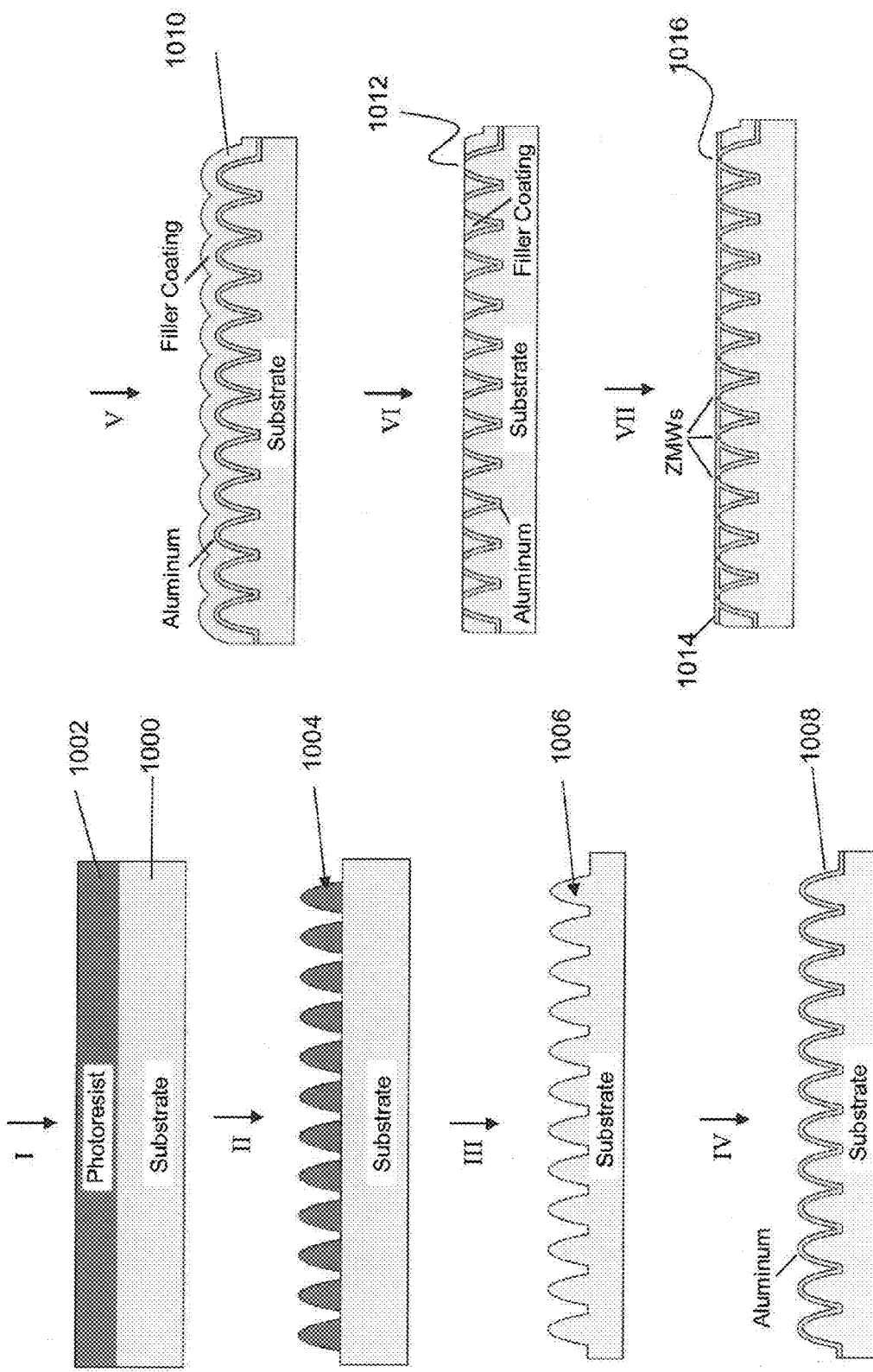
FIGS. 10 through 18 schematically illustrate a fabrication processes for producing substrates with integrated focusing mirrors having associated reaction regions.

One semiconductor fabrication processes process is illustrated in FIG. 10, which illustrates the fabrication of such micromirror optical elements and a zero mode waveguide array where the micromirror elements are produced first, and the ZMW's are produced in subsequent steps. As shown in step I, a transparent substrate layer 1000 is first coated with a resist layer 1002. The resist is then exposed and developed in step II, to provide the desired pattern 1004 of the mirror array. This is transferred to the underlying substrate in step III using, for example, a dry etch transfer process to yield a negative relief 1006 of the mirror array. In the process illustrated herein, an array of mirrors having parabolic structures is produced. In some cases, it may be desirable to provide a smoothing step following the transfer step, in order to alleviate potential optical aberrations from a rougher etched surface. Such smoothing steps may include, e.g., gentle etch steps to provide smoothing of the surface, e.g., lower pressure plasma etches, and/or deposition of smooth layer materials over the transferred surface. Examples of such smooth layers include, e.g., index matched materials, such as $SiO_x$ or $SiO_2$ layers, that may be deposited over the surface using conventional conformal deposition processes, such as low pressure chemical vapor deposition (LPCVD) processes, plasma enhanced CVD processes (PECVD) and the like.

Following the transfer step III, a layer of reflective material 1008, is then deposited over the patterned substrate in step IV. In particularly preferred aspects, the reflective material is a metal coating, such as aluminum or chromium, which is deposited over the patterned surface through metallization processes, e.g., evaporation or sputtering, to define the reflective surfaces of the mirror array. In some cases, deposition or metallization is accomplished using a conformal deposition process, e.g. evaporation.

Following the metallization step, in step V, a fill layer or planarization layer 1010 is deposited over the reflective layer 1008. A variety of fill materials may be employed for this step, including additional metal layers (or continuous metal layers), inorganic materials, such as silicon, silicon dioxide, polymeric materials, semiconductor materials, or the like. In particularly preferred aspects, a silica based layer is deposited as the fill layer, and preferably the layer comprises silicon dioxide or other glass-like material. Production of a glass fill layer may be accomplished through a number of conventional processes, including the use of spin-on glass materials, such as silsesquioxanes, or through the vapor deposition and subsequent oxidation of silicon fill layers over the substrate.

The upper surface is then removed in step VI to expose an opening 1012, in the top portion of the parabolic mirrors, e.g., through surface grinding, polishing or etching, or a combination of these. A metal cladding layer 1014 is then deposited upon the upper surface with apertures such as ZMW cores 1016 disposed through it and in optical communication with the openings in each of the parabolic mirror structures in step VII, to define the ZMW array with integrated parabolic mirrors.

Figure 11:
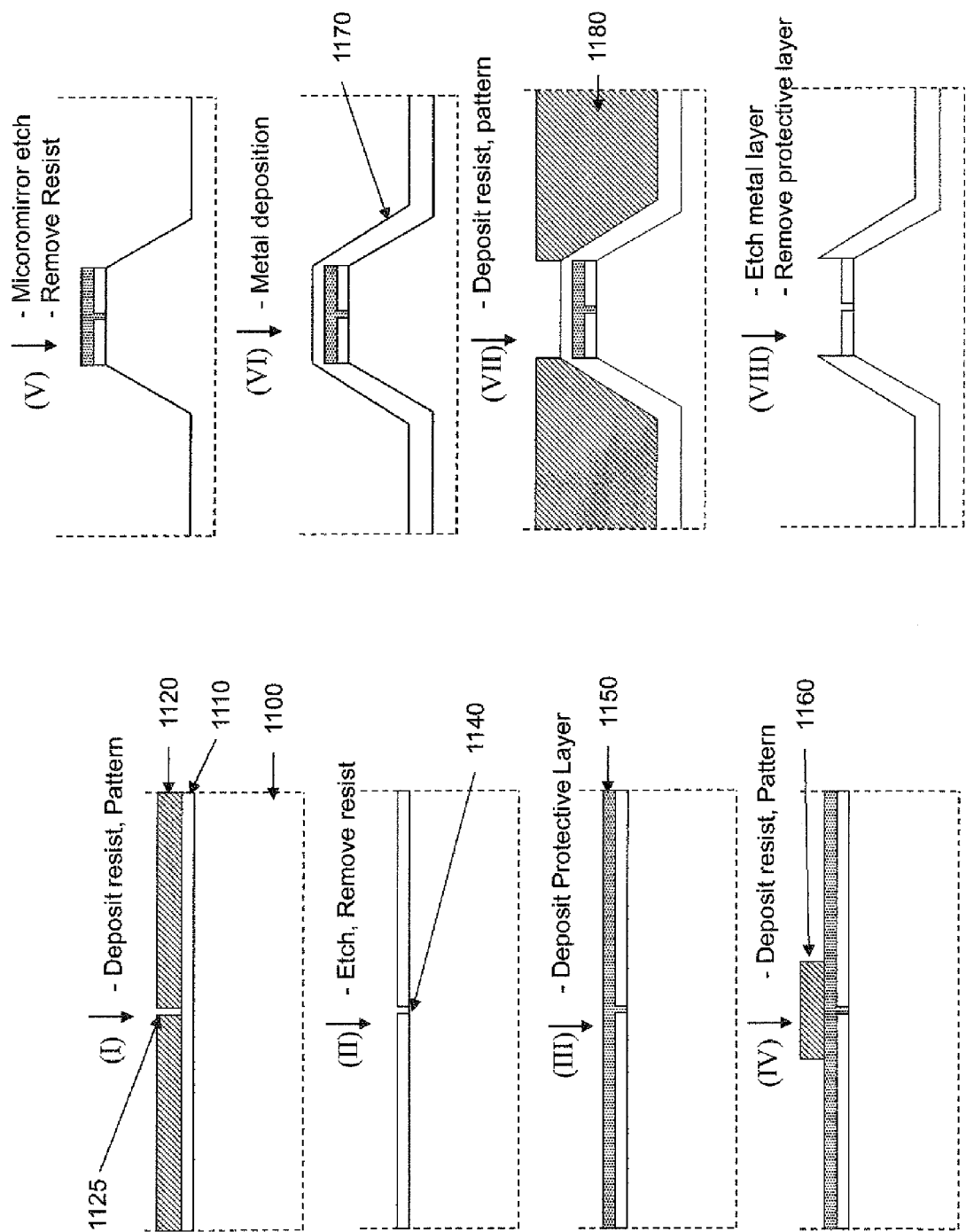

FIG. 11 shows another exemplary process for producing integrated reaction regions and micromirrors of the invention with a transparent substrate. In step (I) a resist 1120, e.g. a photoresist, is deposited onto a transparent substrate 1100 having disposed on its top surface a cladding layer 1110. The resist is patterned and developed to produce an array of features 1125. In step (II), the cladding layer 1110 is etched to produce an array of reaction regions 1140 such as apertures through the cladding. The array of reaction regions 1140 can also be produced by other methods such as those described herein, such as using sacrificial pillars, or by e-beam etching of the cladding layer. In step (III) a protective layer 1150 is deposited onto the substrate. In step (IV) a resist that defines the features of the mirror structure 1160 is deposited, and patterned. In step (V) single or multiple etch steps, are used to create the micromirror structures, shown here as conical. The resist is then removed to expose the protective layer. In step (VI) the reflective layer is deposited, for example by sputtering or evaporating a metal 1170. In step (VII) a resist that defines the tops of the mirror structures 1180 is deposited and patterned. In step (VIII) the portion of the metal that is not covered with resist is etched, to expose the protective layer below it. The protective layer is then removed to open up the apertures. The resulting array has a reaction regions made up of apertures through the cladding layer, each disposed on the top of a mirror structure.

Figure 12:
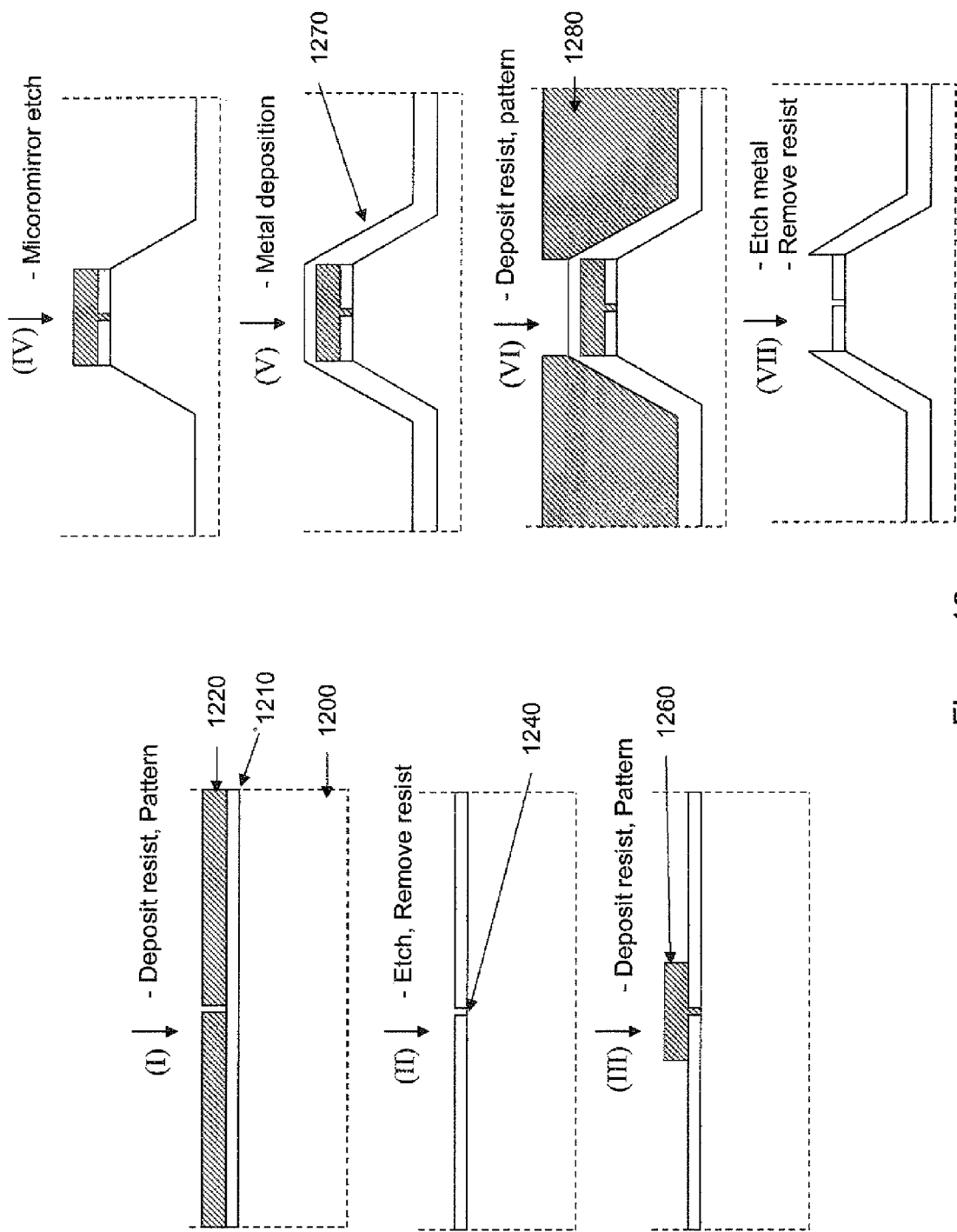

An alternative exemplary process of the invention is shown in FIG. 12. Steps (I) and (II) produce an array of apertures 1240 in cladding layer 1210 on top of transparent substrate 1200 using resist 1220. The array of reaction regions 1240 can also be produced by other methods such as those described herein, such as using sacrificial pillars, or by e-beam etching of the cladding layer. A resist which defines the micromirror structures 1260 is deposited and patterned in step (III). In step (IV) resist geometry and etching conditions are controlled to produce a feature having tapered side walls for the micromirror structure, shown here as a conical structure having substantially straight side walls. In step (V) the reflective layer is deposited, e.g. as a metal layer 1270. A resist 1280 is deposited and patterned in step (VI) to expose regions above the resist regions on top of the micromirror structures. In step (VII) the exposed metal is etched, then the resist is removed to expose the apertures, thus producing an array of reaction regions, each with associated micromirrors.

Figure 13:
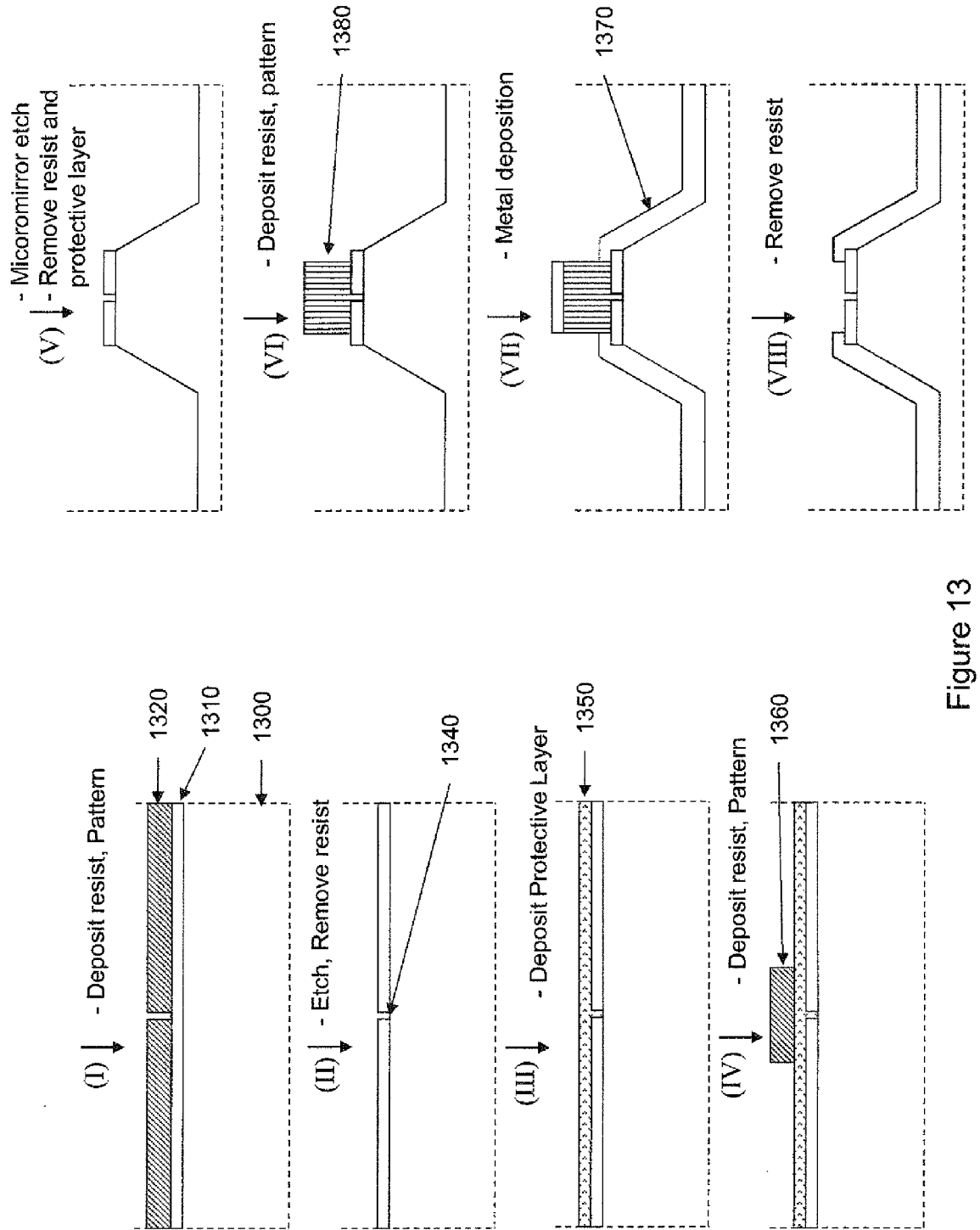

FIG. 13 shows another exemplary process of the invention. First, steps (I) and (II) produce an array of apertures 1340 in cladding layer 1310 on top of transparent substrate 1300 using resist 1320. The array of reaction regions 1340 can also be produced by other methods such as those described herein, such as using sacrificial pillars, or by e-beam etching of the cladding layer. Then, in step (III) a protective layer 1350 is deposited. In step (IV) a resist which defines the micromirror structures 1360 is deposited and patterned. In step (V) an etching process is used to produce the micromirror structures having tapered sidewalls, and the resist and protective layer is removed. Resist pillars 1380 are created on the tops of the micromirror structures by resist deposition, patterning, and removal in step (VI), and in step (VII) metal 1370 is deposited to form a reflective layer on the micromirror. In step (VII) the resist is removed, removing resist pillars and the metal which had deposited on top of them, thus producing an array of reaction regions, each with associated micromirrors.

Figure 14:
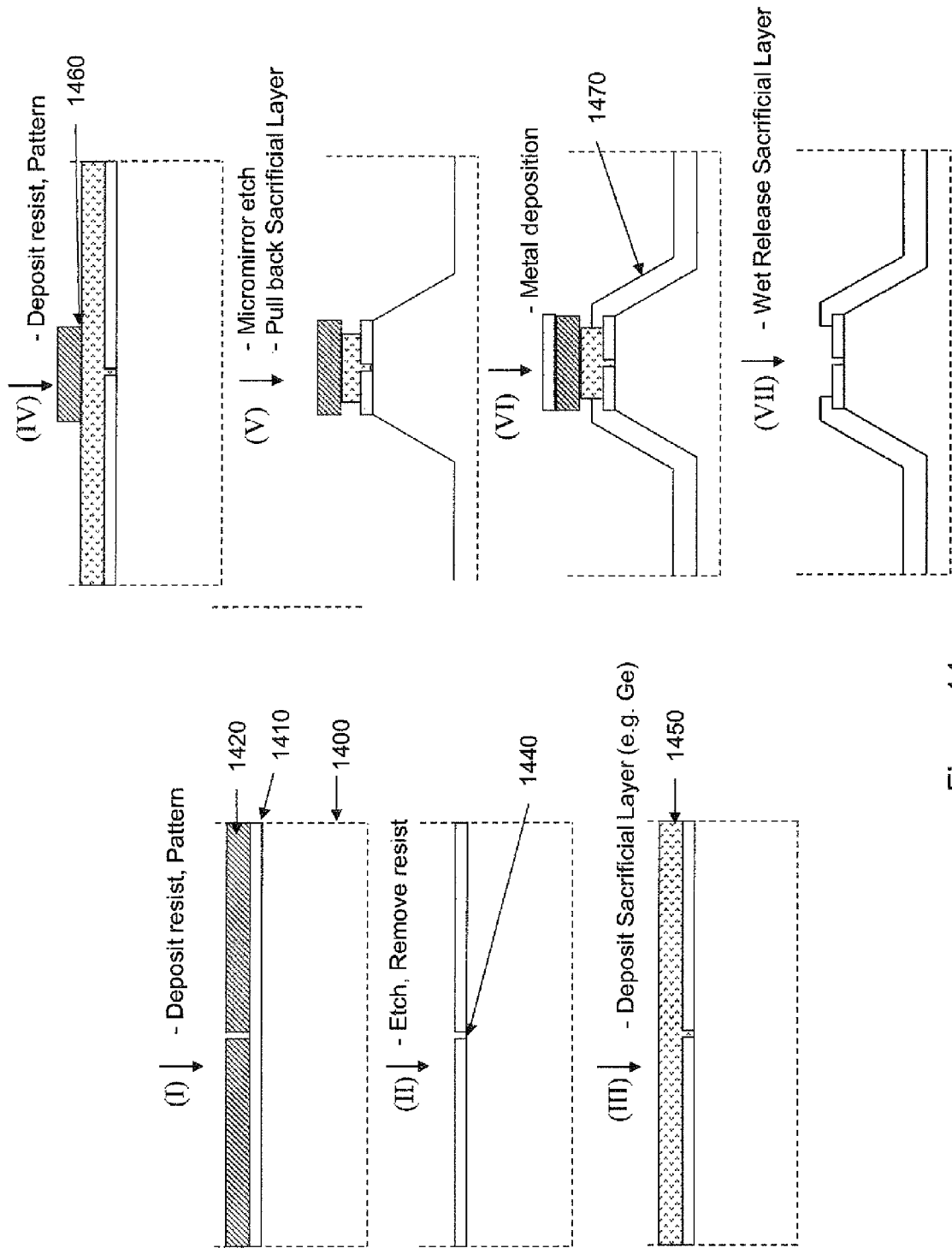

In FIG. 14, which shows another exemplary process, steps (I) and (II) produce an array of apertures 1440 in cladding layer 1410 on top of transparent substrate 1400 using resist 1420. Then, in step (III) a sacrificial layer 1450 is deposited. A preferred sacrificial layer comprises germanium or silicon. In step (IV) a resist which defines the micromirror structures 1460 is deposited and patterned. In step (V) an etching process is used to produce the micromirror structures having tapered sidewalls, and a pull-back process is used to pull back the edges of the sacrificial layer over the tops of the micromirrors. In step (VI) metal 1470 is deposited as the reflective layer for the micromirrors. Sputtering can be a useful process for this metal deposition step as it can produce effective sidewall coverage without covering the sidewall of the sacrificial layer. In step (VII) the sacrificial layer is released, also removing the resist and metal layers on top of the sacrificial layer. The use of a wet release process for releasing the sacrificial layer can be advantageous by allowing the release material to diffuse through access holes, in some case creating bubbles which help to remove the resist and metal layers on top of the sacrificial layer effectively. In some cases, sonication is used along with the wet release process. The method produces an array of reaction regions, each with associated micromirrors on a transparent substrate.

Figure 15:
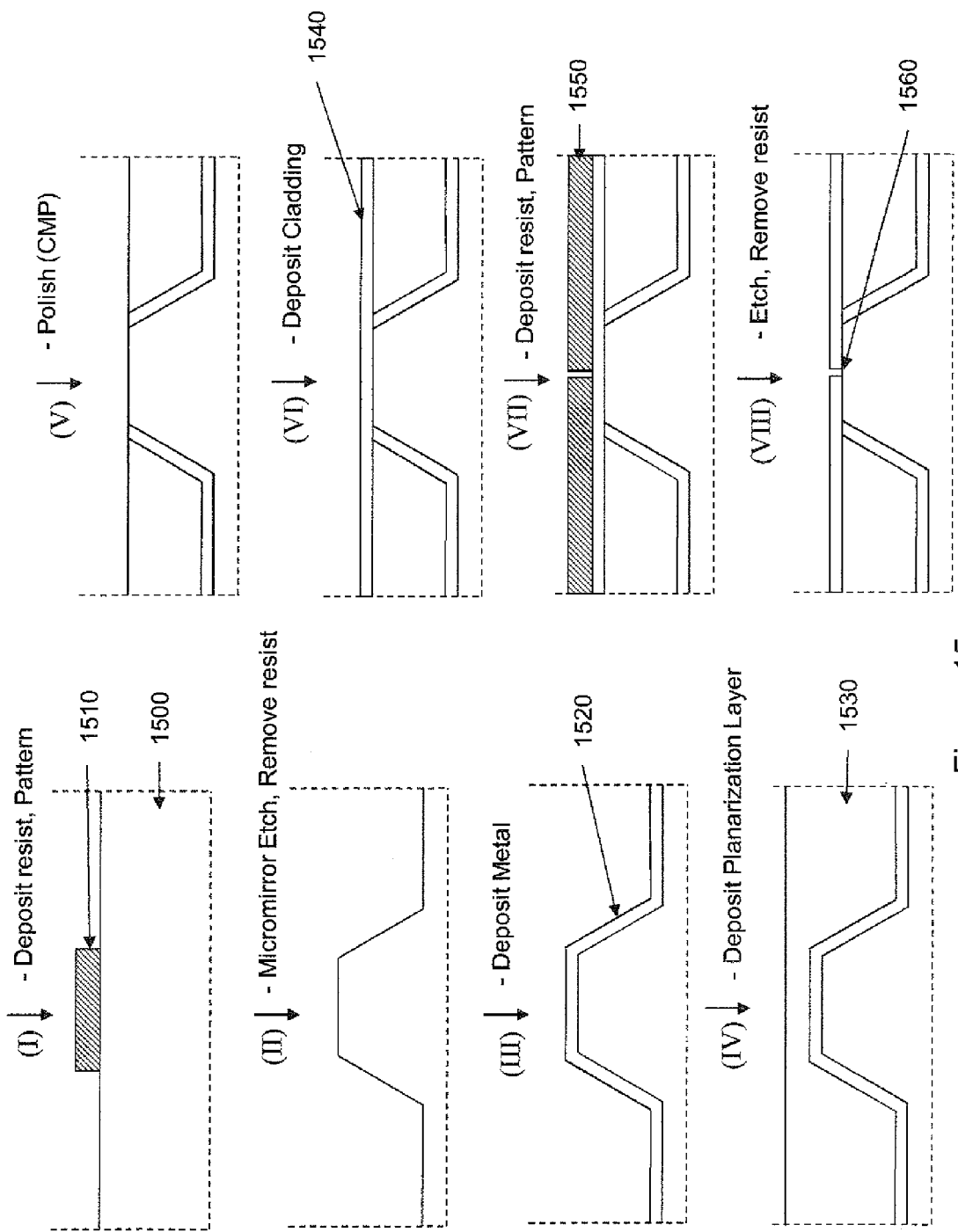

FIG. 15 shows an alternative process of the invention. In step (I) a resist which defines the micromirrors 1510 is deposited and patterned on the transparent substrate 1500. The micromirror structures are then produced in the transparent substrate 1500 using, for example, a reactive ion etching process. Onto the micromirror structures is deposited a metal reflective layer 1520 in step (III). A planarization layer 1530, such as a spin on glass or PECVD oxide is deposited in step (IV). The thickness of the planarization layer can be, for example, 8 microns to 10 microns. The planarization layer can be a hard material such as a spin-on glass, or may be a soft planarization layer. The soft planarization layer could be for instance a spin-on UV curable organic polymer such as Summers J91 or SK9. Where the planarization layer comprises a hard material, the planarization is generally polished, for example with chemical mechanical polishing (CMP) as illustrated in step (V). Where the planarization layer comprises a soft material, such as a UV cure polymer, then after UV cure, oxygen etch can used to etch away the top region of the spin-on polymer to reach the tops of the micromirrors, analogous to polishing. The polishing or oxygen etch step exposes the tops of the micromirror structures. In step (VI) a metal cladding layer 1540 is deposited onto the surface. In step (VII) a resist for defining the apertures 1550 is deposited and patterned. In step VIII, the cladding layer is etched to form the reaction regions 1560, and the resist is removed to produce an array of reaction regions, each with associated micromirrors on a transparent substrate.

Figure 16:
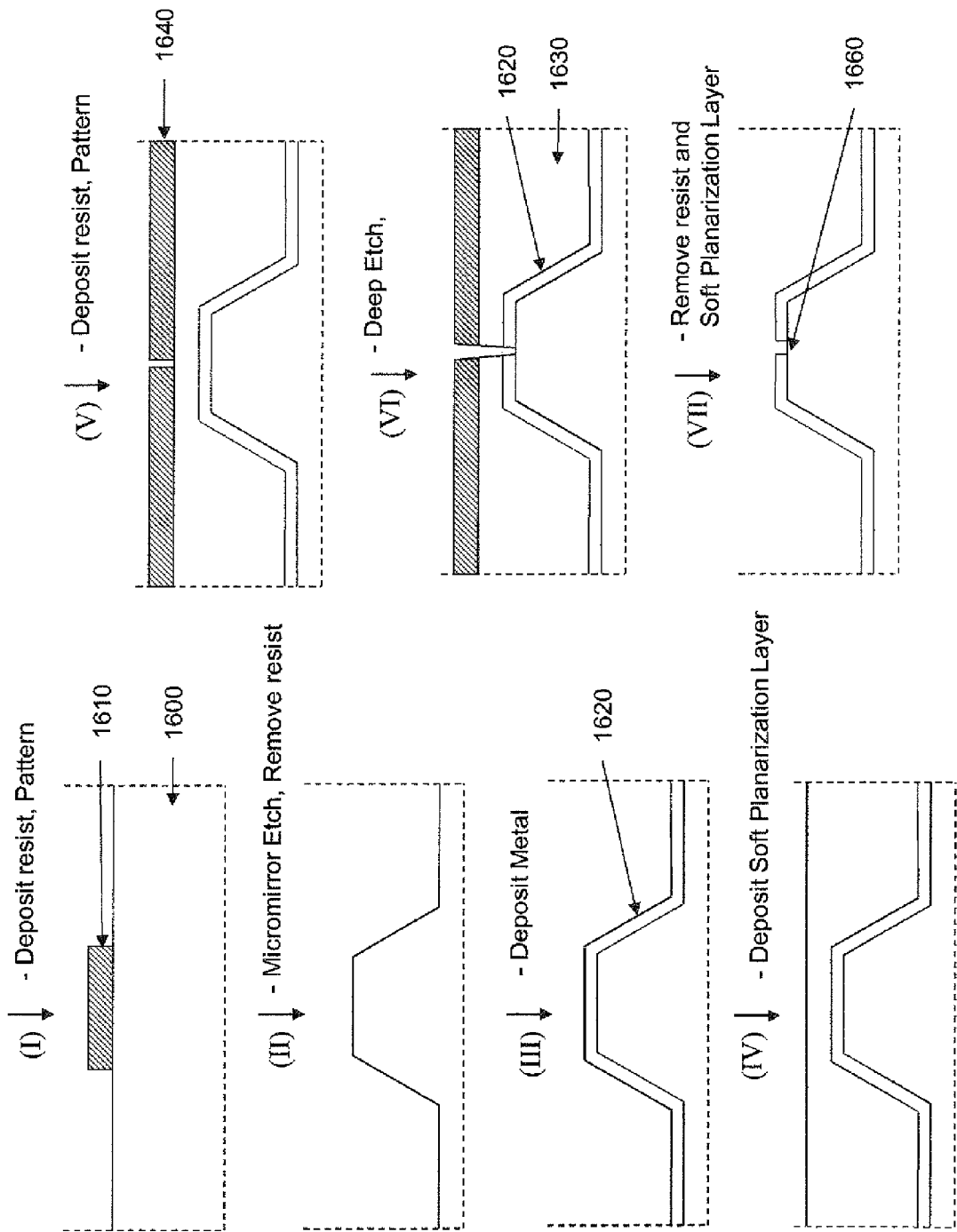

FIG. 16 shows yet another alternative process of the invention. In step (I) a resist which defines the micromirrors 1610 is deposited and patterned on the transparent substrate 1600. The micromirror structures are then produced in the transparent substrate 1600 using, for example, a reactive ion etching process. Onto the micromirror structures is deposited a metal reflective layer 1620 in step (III). A soft planarization layer 1630, such as a polymeric layer, is deposited in step (IV). The soft planarization layer could be for instance a spin-on UV curable organic polymer such as Summers J91 or SK9. In step (V) the resist for defining the reaction regions 1640 is deposited and patterned. In step (VI) a deep etch is performed which etches through the soft planarization layer 1630 and metal layer 1620 to form reaction regions 1660. In step (VII) the resist and soft planarization layers are removed, thus producing an array of reaction regions 1660, each with associated micromirrors on a transparent substrate.

Figure 17:
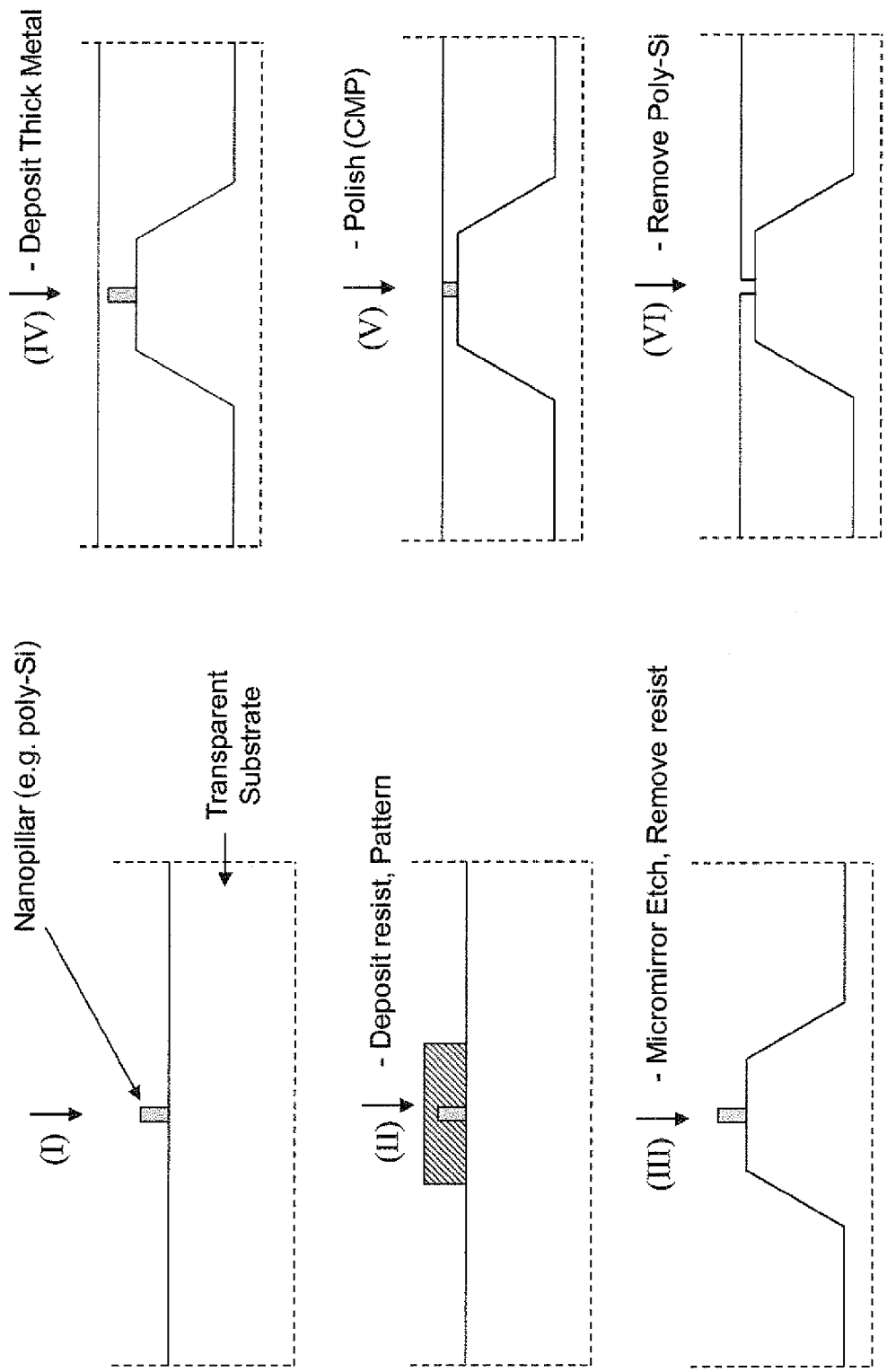
Figure 18:
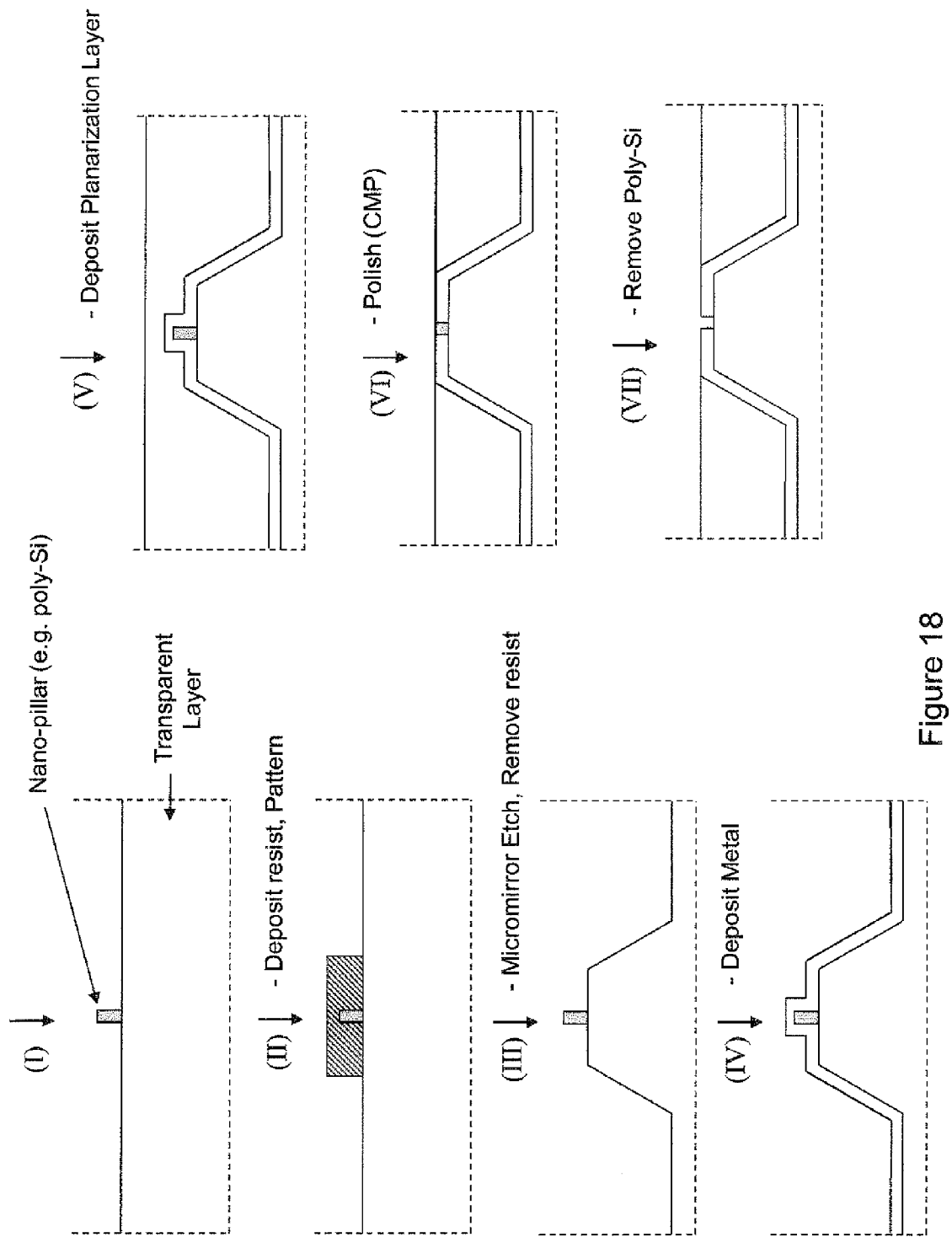

FIG. 17 and FIG. 18 shows alternative processes of the invention that utilize small pillars (nanopillars) which are formed from a layer that is deposited onto a transparent substrate such as fused silica. The nanopillars are formed onto the surface, and are later removed to produce the reactive regions of the invention. The nanopillars may be formed from a layer of any suitable material. Preferred materials for formation of the nanopillars are poly crystalline silicon (poly-Si) or poly crystalline germanium (poly-Ge). Poly-Si can be deposited onto the transparent substrate for example by low pressure chemical vapor deposition (LPCVD), plasma-enhanced chemical vapor deposition (PECVD), or solid-phase crystallization (SPC) of amorphous silicon. The use of nanopillars such as poly-Si nanopillars to produce reactive regions can be incorporated into the other methods described herein, such as those described above. While some methods are described for nanopillars made from poly-Si, it is to be understood that these methods can employ nanopillars from other suitable materials.

For the method shown in FIG. 17, in step (I) an array of polysilicon nanopillars is created on top of a transparent substrate, for example by depositing a polysilicon layer onto the transparent substrate, depositing resist and patterning the resist to define the nanopillars, and etching away the unwanted polysilicon regions to produce the nanopillars. In step (II), a resist for forming the micromirror structures is deposited and patterned. In step (III) etching of the transparent substrate is performed to produce the micromirror structures having tapered sidewalls. In step (IV), a thick metal is deposited so as to bury the nanopillars and to fill in the regions between the micromirror structures. In step (V), the metal layer is planarized, for example by CMP, such that the tops of the nanopillars are exposed. The exposed nanopillars are then removed in step (VI) to produce an array of reactive regions. In this embodiment, the metal acts both as the cladding layer and as the reflective surface on the walls of the micromirror structures. In some cases, the thick metal layer can be useful for thermal management, as the metal layer can be produced to have a relatively high thermal transfer coefficient.

FIG. 18 shows an alternative method using nanopillars to produce the array of reaction regions. In step (I), an array of polysilicon nanopillars is created on top of a transparent substrate, for example by depositing a polysilicon layer onto the transparent substrate, depositing resist and patterning the resist to define the nanopillars, and etching away the unwanted polysilicon regions to produce the nanopillars. In step (II), a resist for forming the micromirror structures is deposited and patterned. In step (III) etching of the transparent substrate, for example reactive ion etching, is performed to produce the micromirror structures. In step (IV), metal layer is deposited so as to form a metal cladding layer on top of the micromirror structure, and a reflective layer on the sides of the micromirror structures. In step (V), a planarization layer, such as a spin-on glass is deposited to fill in the regions between the micromirror structures. In step (VI), a planarization or polishing step is performed to planarize the planarization layer and the metal layer on top of the micromirror structures, and to expose the nanopillar structures. In step (VII), the nanopillar structures are removed to produce the array of apertures or reactive regions, each associated with a micromirror structure.

Figure 19:
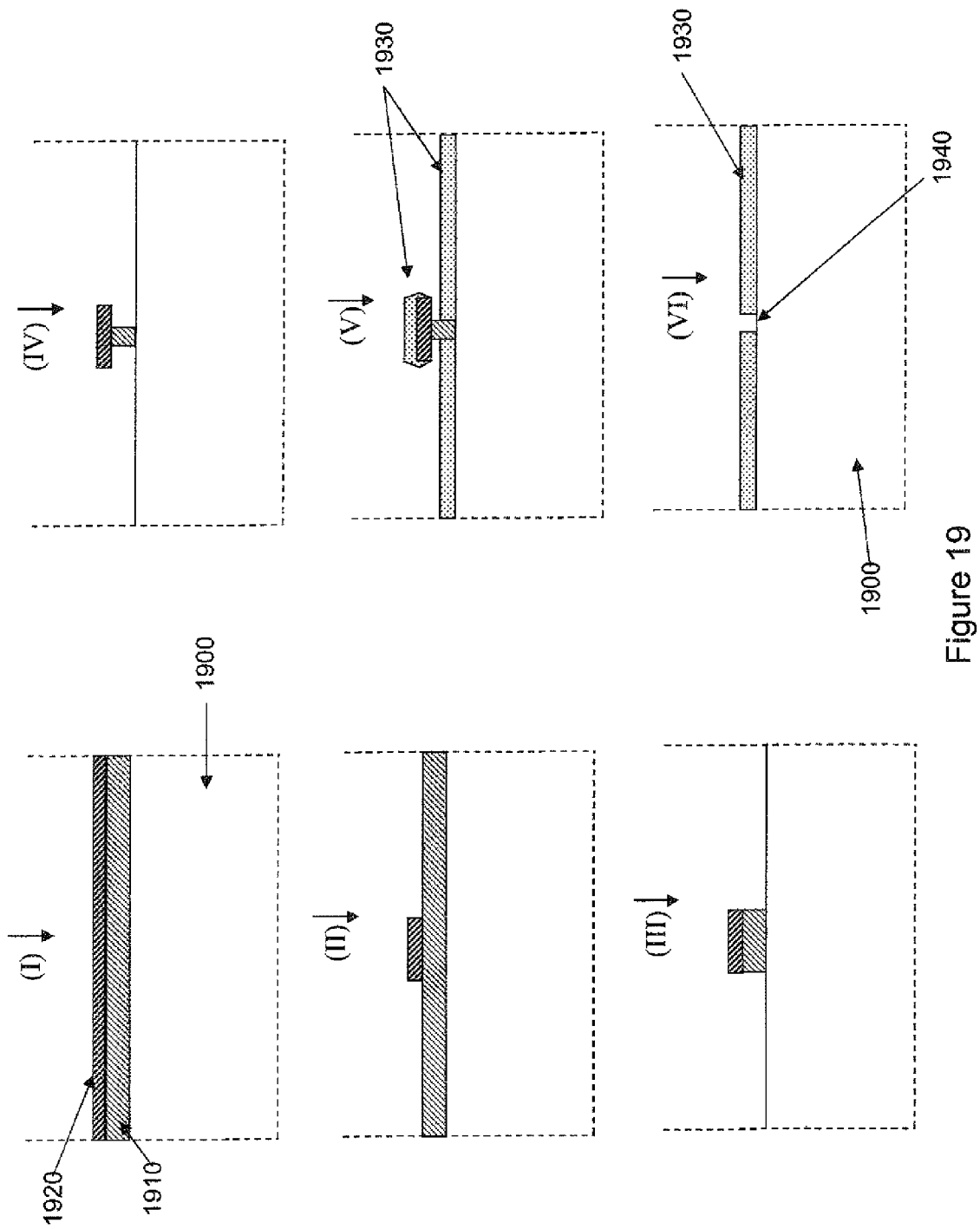
FIG. 19 schematically illustrates a method for producing a reaction region by creating a sacrificial pillar using an undercut process.

FIG. 19 shows a method of forming a reaction region such as a nanoscale aperture of the invention using a sacrificial layer. The method shown in FIG. 19 can be incorporated into or combined with any suitable method described herein to form the arrays of reaction regions associated with micromirrors of the invention including any of those described above with respect to FIGS. 10-18. In step (I), a sacrificial material 1910 is coated onto the transparent substrate 1900, and a hard-mask layer 1920 is coated onto the sacrificial material 1910. The sacrificial material can be, for example, poly-Si or poly-Ge. The hard-coat material can be for example an oxide or nitride such as silicon oxide or silicon nitride. The hard-coat material should have acceptable selectivity to the sacrificial material during the subsequent etch steps. In step (II) lithography is used to etch the hard-mask. In step (III) and step (IV), the sacrificial layer is etched. The etch is performed using a controlled over-etch as shown in step (IV) producing a specific undercut and forming a sacrificial pillar. The undercut can be carried out such that the diameter or other surface dimension of the hard-coat mask ($W_1$) is 1.1 to 3 times the diameter of the sacrificial layer (Wp). In some cases $W_1/Wp$ is between about 1.5 to about 2.5. In some cases $W_1/Wp$ is between about 1.6 to about 2.2. The undercut dimensions can be, for example, between about 10 nm and about 300 nm, between about 50 nm and about 200 nm, or between about 70 nm and about 150 nm. Metal cladding 1930 is then deposited onto the surface. The cladding deposition is carried out in such a manner, e.g. by sputtering, such that the metal is deposited onto the transparent region under the areas where the hard-mask extends over the sacrificial layer. In step (VI), the sacrificial pillars are removed, for example with an agent that preferentially dissolves the sacrificial material to expose reaction regions 1940. Where the sacrificial material is germanium and the metal cladding is aluminum, an aqueous oxidizing agent can be used which will dissolve the germanium without substantially removing the aluminum.

Figure 20:
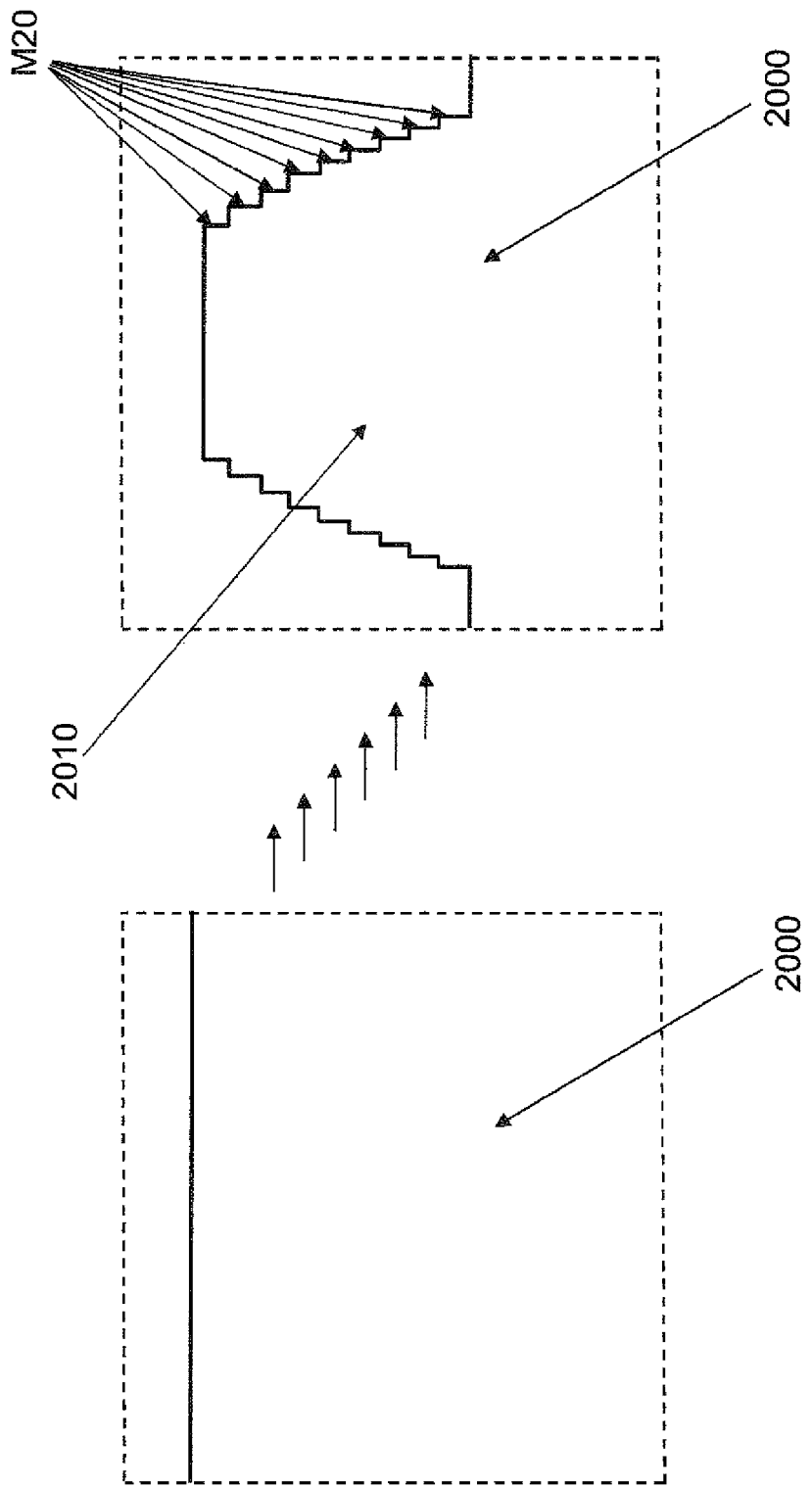
FIG. 20 schematically illustrates a method for forming shaped micromirror structures on a transparent substrate using multiple lithography and etching steps.

The etching of the transparent substrate to form the micromirror structures can be carried out in a single step or in multiple steps. In some cases, the mirror structure can be formed using a series of photolithography and etching steps. While using multiple etching steps adds more steps to the process, in some cases, the series of steps can be used to provide greater control of the micromirror structure. In some cases, 2, 3, 4, 5, 6, 7, 8, 9, 10, 11, 12, 13, 14, 15, 20, 30, or more steps can be used. FIG. 20 shows an exemplary process using multiple lithography and etch steps. For the process depicted in FIG. 20, the substrate 2000 is coated with photoresist, patterned, and etched nine (9) times. The first layer is etched, for example, to produce a cylindrical structure with the diameter of the lowest layer. Each subsequent photoresist layer is then patterned to have circles with slightly smaller diameters than for the preceding layer. The result of the multi-step process is an array of structures 2010 that have structures with profiles as defined by the layers of resist. In some cases, the approach will lead to a structure with a series of terraces 2020 defined by the layers 2010. If desired, the walls of the structures can be smoothed, for example by wet or dry etching to partially or completely smooth out the terrace structures. The structures can be reflectively coated, and the associated reactive regions can be produced as described herein, before or after the formation of the micromirror structures by multiple etch steps. The structure 2010 depicted in FIG. 20 is shown as having relatively straight side walls (with terraces), but the multiple etch step method can be used to produce structures having any arbitrary shape including curved walls, staged conical structures, parabolic structures and the like. The multiple etch steps can incorporate any combination of isotropic, anisotropic, or gray-scale etching steps. While the described process results in a cylindrically symmetrical structure, it will be appreciated that the multistep method can also be used to produce structures having other symmetries that are not cylindrically symmetric.

The methods of the invention in some cases use resists for defining and producing structures with lithography. These resists can be, for example, photoresists or e-beam resists. The photoresists can be developed using UV, deep UV, G-line, H-line, I-line or other suitable wavelength or set of wavelengths. The type of resist that is used, and therefore the type of instrumentation that is employed for processing will depend on the dimensions of the features that are created. In many processes described herein, higher resolution resists and equipment will be used for the production of the aperture which corresponds to the reaction volume, where the size of the aperture may be on the order of 10 nm to 500 nm, and a lower resolution resist and associated instrumentation is used for the creation of the micromirrors, which may have features on the dimensions of 1 micron to 20 microns. Many resists are known in the art, and many are available commercially from companies such as Rohm and Haas and Shipley. The resists used in the processes of the invention can be negative or positive photoresists. Where a process is described herein using a negative photoresist, it is to be understood that a suitable positive photoresist may also be employed where practical, and visa versa. Where appropriate, chemical amplification can also be employed in order to increase the sensitivity of the resist. The removal of the resist, the cleaning, rinsing, ashing, and drying of the substrate can be performed as appropriate and as taught in the art.

In some cases, the tools used for photolithography of the reaction region (e.g. ZMW) use photolithography exposure tool capable of creating structures having feature sizes of about of 10 nm to about 100 nm. Such systems include, for example, an AMSL XT1250 exposure tool.

Etching processes are used in some aspects of the invention in order to produce the three dimensional features in the transparent substrate or in other layers, to fashion, for example, optical elements such as micromirrors or lenses, or reaction volumes such as nanoscale apertures. The etching process that is used will depend on the type of material used, the dimensions of the features, and the resist system. In some cases wet etching or wet chemical etching is employed. Electrochemical etching can also be employed. In some embodiments plasma etching or reactive ion etching (RIE) is used as an etching process. Deep reactive ion etching (DRIE) may also be employed, for example, where structures having high aspect ratio are desired. Dry vapor phase etching, for example with xenon difluoride, can also be used. Bulk micromachining or surface micromachining can be used as appropriate to create the structures of the invention. The etching used in the processes of the inventions can be gray-scale etching. The conditions of the resist formation and etching are controlled to produce side walls having the desired geometries to act as micromirrors, such as having the desired side-wall angle.

Some processes of the invention involve the deposition of reflective layers, or cladding layers. The deposition of these reflective layers can be accomplished by wet processes including spinning on layers from solution, or by gas-phase processes. Suitable processes include electroplating, sputter deposition, physical vapor deposition, evaporation, molecular beam epitaxy, atomic layer deposition, and chemical vapor deposition. Metals can be used as the reflective layer and the cladding layer. Suitable metals include gold, nickel, aluminum, chromium, titanium, platinum, and silver. The reflective and/or cladding layers can comprise aluminum, which can be deposited by sputtering, for example using a commercially available sputter tool available from CVC, Novellus, or MRC.

Where layers are deposited during the processes of the invention, in some cases, the layers are treated before moving on to the next step in the process. For example, the deposited layer may be annealed, planarized, cleaned, passivated, or lightly etched in order to improve its properties.

In some processes of the invention, protective layers or sacrificial layers are deposited. The protective layers can be polymeric layers, or can be inorganic layers. Suitable protective or sacrificial layers include germanium (Ge) and amorphous silicon (a-Si). Protective layers can be used to produce features as described herein. The type of material for the protective or sacrificial layer can be chosen for its selective reactivity, for example to wet chemical etchants. For example, in some cases, the ability to selectively etch germanium with heated hydrogen peroxide in the presence of silicon dioxide and aluminum results in its being utilized to produce the optical micromirror structures combined with nanoscale apertures.

In some processes, a pull-back process is employed. A pull-back process generally involved etching in from the edges of a feature within a layer in order to reduce the dimensions of the feature. Pull-back can be performed using a wet chemical reagent that selectively reacts with a layer which has exposed edges. In some cases a germanium layer is pulled back using hydrogen peroxide.

Some processes employ a polishing step to remove a surface region from the substrate. Suitable processes include chemical-mechanical polishing or chemical-mechanical planarization (CMP).

Some processes of the invention incorporate a planarization layer. The process for depositing the planarization layer will depend on the type of material that is used. The planarization layer can be a hard material, such as an inorganic material, for example silicon nitride; it can be a metallic material such as aluminum; or it can be a soft material, such as a polymeric material, e.g. an organic or silicon based polymer. The planarization layer can be a glass, such as a silicon dioxide material. In some cases, the planarization layer comprises a spin-on glass such as a silicate, phosphosilicate or siloxane material. Suitable spin-on glass materials are available, for example, from Honeyewell Corporation. The planarization layer can comprise, for example, a glass doped with other agents to control its melting properties, such a boro-phosphoro-silicate glass (BPSG). Suitable polymeric planarization materials include, for example, polyimides.

The arrays of the invention can be incorporated into analysis systems for analyzing the multiple reactions occurring in the reaction regions of the array. The arrays described herein typically have reaction regions that are accessible to fluid from the top, and which are accessible for optical analysis from the bottom. The arrays are thus generally incorporated into a vessel into which a reaction mixture of interest is introduced. In some cases, the individual reaction regions are all in contact with one volume of fluid, which may have, for example, multiple nucleic acid template molecules which can be analyzed, and which may have the nucleotides, cofactors, and other additives for carrying out the reaction to be analyzed.

The vessel that comprises the array can be placed within an instrument which has the appropriate optical components, computer controls, and data analysis systems. The vessel comprising the array will be held within the instrument such that the reaction conditions, such as the vessel temperature and vessel atmospheric conditions can are controlled. The vessel atmospheric conditions can comprise the makeup of the gas above the sample, for example the humidity, and the level of other gaseous species such as oxygen.

Integrated Lens Arrays

As with integrated parabolic mirrors, lens arrays may be fabricated using a variety of conventional technologies, including for example semiconductor fabrication processes, micromolding of polymeric materials, and the like. For example, as with components of the fabrication process for the integrated mirrors, described above, etching processes such as reactive ion etching may be employed to produce such lens arrays. Alternatively, as noted above, variable ion implantation processes may be employed to vary refractive index of substrate components to define lenses with an existing substrate. As will also be appreciated, additional optical elements that provide for improved collection of light from the reaction regions may be fabricated into the substrate as well. For example, the foregoing ion-implantation processes may be used to define diffraction gratings for each different reaction region directly in the substrate.

Figure 21:
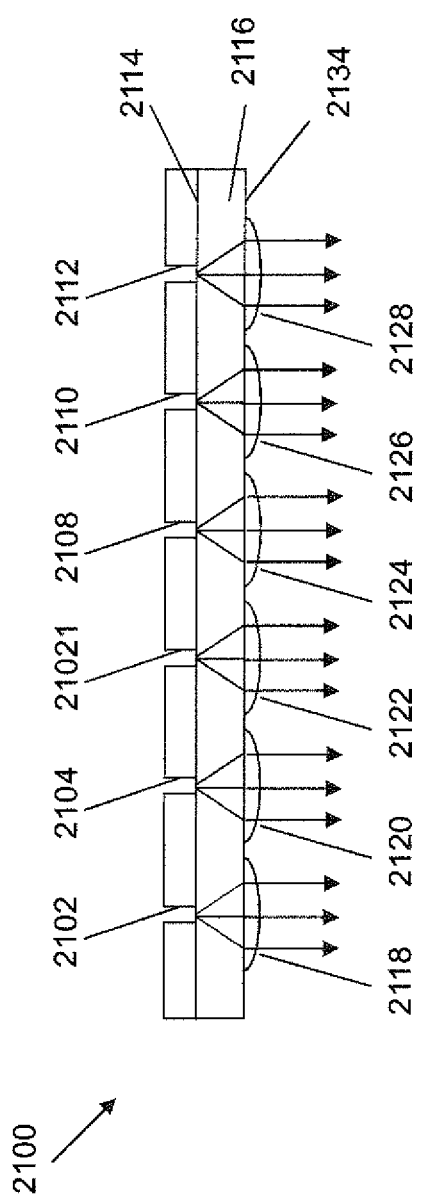
FIG. 21 schematically illustrates a substrate having an array of reaction regions and an array of lenses where the lenses redirect emitted light from the reaction regions.

In alternative aspects, conical or parabolic mirrors are replaced with (or in some cases, augmented with) lens arrays that at least partially collimate or focus the fluorescent signals to and/or from the substrate. Such a lens array is illustrated in FIG. 21. As shown, the overall device 2100 again includes an array of zero mode waveguides, e.g., ZMWs 2102-2112, disposed upon a first surface 2114 of a transparent substrate 2116, and in which the reactions of interest are carried out. An array of micro or nano-lenses, e.g., lenses 2118-2128, is disposed upon the opposing (or back) surface 2134 of the transparent substrate 2116. As shown, these lenses are of a size, and disposed at a pitch that matches that of the ZMW array so that each ZMW has its own associated lens. As with the mirror array of FIG. 5B, the light emitted from the ZMW is redirected, for example partially collimated by its associated lens, and that light is collected and analyzed in monitoring the reaction of interest. While such lenses are not as effective as the parabolic mirror structures at eliminating cross-talk within the substrate, they provide additional benefits of cost and ease of manufacturing, and may, in some cases, be used in place of or in addition to such integrated mirrors.

As illustrated, the lens array may be integrated into the underlying transparent substrate. Alternatively, the lens array may be separately fabricated and joined to the underlying substrate to provide the same or similar results. Although illustrated as a single layer of lenses disposed at the back surface of the array, it will be appreciated that the lens array may be comprised of multiple lens layers that each address different regions on the substrate, or combined to provide a desired optical functionality at a given region on the substrate. Additionally, although illustrated as lenses protruding from the back surface of the transparent substrate, in some cases, the lenses may be integrated within the transparent substrate. For example, lenses may be fabricated into the underlying substrate at the appropriate locations by providing variations in the index of refraction of the substrate in such locations. Discrete lenses can be embedded in the substrate using micromachining techniques to provide binary index of refraction, as in conventional lens fabrication. Additionally, by creating a gradient of refractive index at selected portions of the substrate, these portions of the substrate can function as lenses. Alteration of the refractive index of the substrate, e.g., a glass substrate, can be accomplished a number of ways, including, for example, ion implantation methods. In addition to lenses or lens arrays, diffractive gratings or other optical functionalities could likewise be fabricated into the underlying substrate.

Because the signals from the substrate are at least partially collimated by the focusing optics, the need for narrow field of view, high numerical aperture objectives is reduced, and larger field of view, lower NA objectives may be employed, which generally imparts cost and availability advantages to the overall system, as less stringently manufactured objectives may be used. In addition, the exotic materials used to manufacture higher power objectives can give rise to increased photoluminescence of the objective itself, when exposed to excitation radiation.

In addition, because lower power objectives are employed, greater spacing can be provided between the objective and the substrate than is generally provided when employing high numerical aperture objectives. This additional spacing permits the insertion of additional optical components, e.g., appropriate dichroic(s), between the substrate and the collection objective. In at least one exemplary embodiment, provision of a dichroic between the substrate and the objective allows the separation of the illumination light from the collection objective (and other collection optics components. By further separating the excitation path from the detection path, and particularly by providing a collection objective that does not see excitation light, one can completely eliminate autofluorescence or photoluminescence in the collection path that results from passage of excitation illumination through that objective. An illustration of this optical set-up is shown in FIG. 22A. As shown, the overall system 2200 includes a substrate 2202 upon which a number of reaction regions 2204 are disposed. Also included, either integrated into the substrate (as shown), or as a discrete component, are focusing optics (e.g., integrated micromirrors or lenses as described above), for example, for collimating optical signals from the reaction regions and/or focusing illumination onto the reaction regions. The system also includes an excitation light source 2206, or multiple excitation light sources, for providing excitation light to the substrate 2202. Excitation light is directed at the substrate via dichroic 2208 that is positioned between the collection objective 2210 and the substrate 2202. By separating the excitation light from the collection objective 2210, one avoids problems associated with the autofluorescence of the collection objective lens 2210, which can be a significant contributor to such noise.

Prior to being reflected by dichroic 2208 to substrate 2202, the excitation illumination will also typically be subjected to additional manipulations, such as beam splitting, beam shaping, filtering, and the like. For example, the excitation light may pass through multiplex optics to provide large numbers of individual beamlets, e.g., DOE 2212, as well as focusing optics, e.g., objective 2214, for focusing the beamlets on the focal plane of the substrate.

Emitted signals, by virtue of their different spectral characteristics from the excitation light, are passed through dichroic 2208, and collected by collection objective 2210. As noted previously, where the signals from the substrate are already partly collimated by the focusing optic elements, the collection objective can be of much lower power, e.g., going from a 60× (n.a. 0.9) or greater objective having a FOV of 3 mm or less for a system without focusing optics, to a 4× (n.a. 0.28) or less objective having a FOV of 45 mm or more, while still providing sufficient sensitivity for single molecule analyses. As with the system shown in FIG. 2, the collected signals may then be subjected to spectral separation, e.g., by passing through prism 2216, and further focusing, e.g., through lens 2218, or other manipulations prior to detection at detector 2220.

Figure 22B:
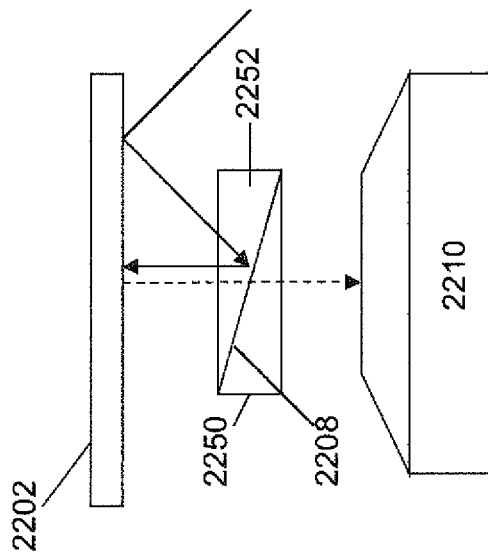
FIG. 22 schematically illustrates an illumination and detection system that employs larger field of view (FOV) objective lens, allowing for intervening optical components.
Figure 22A:
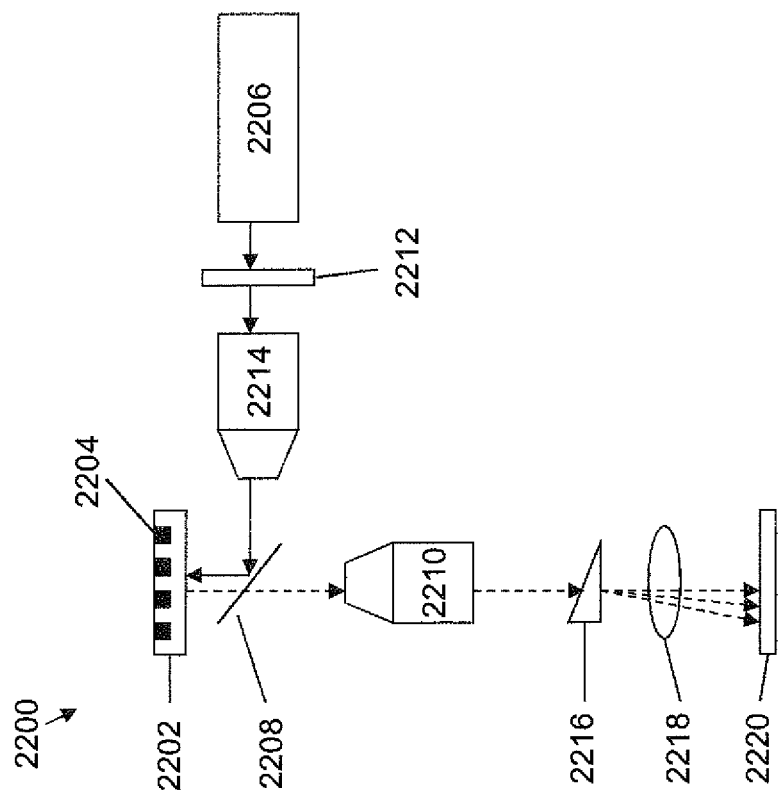

An additional or alternative illustration of the dichroic and illumination path at the substrate is shown in FIG. 22B. As shown, the dichroic layer 2208, is sandwiched at the interface between two prisms 2250 and 2252. Excitation radiation from an illumination source, e.g., laser 2206, is directed at the dichroic 2208. As shown, the excitation radiation is first reflected off of the back surface of the substrate 2202, as shown by the solid arrow. The excitation light is then reflected by the dichroic 2208 toward the substrate and the reaction regions disposed upon it, e.g., reaction regions 2204 in FIG. 22A. Fluorescent signals emanating from the reaction regions then pass through dichroic 2208 into objective lens 2210, and into the remainder of the optical train and detection system, e.g., as shown in FIG. 22A. By providing the overall dichroic element in an orientation that is normal to the optical path, e.g., as shown in FIG. 22B, as opposed to it being tilted relative to such orientation, e.g., as shown in FIG. 22A, one reduces the amount of optical aberrations introduced into the objective space, which can in turn, reduce the image quality at the detection plane or confocal plane, as may be the case.

B. Time Multiplexed

In one aspect, increased multiplex may be achieved through the temporal multiplexing of a given system, e.g., exposing different regions at different times, in addition to or in place of the other enhanced multiplexing schemes described herein. Such systems can include switching between different sets of regions at a relatively slow speed, which is analogous to a scanning approach, e.g., illuminating and/or detecting from different regions at different times, where the different timing is less critical for the different regions. Alternatively, and with reference to aspects of the present invention, the temporal multiplexing of analysis is carried out at a sufficient frequency that for a given analysis, the illumination and/or detection is carried out substantially simultaneously among the different regions, e.g., such that detection among the different regions appears simultaneous from the aspect of camera frame capture rates, as set forth previously.

Figure 23:
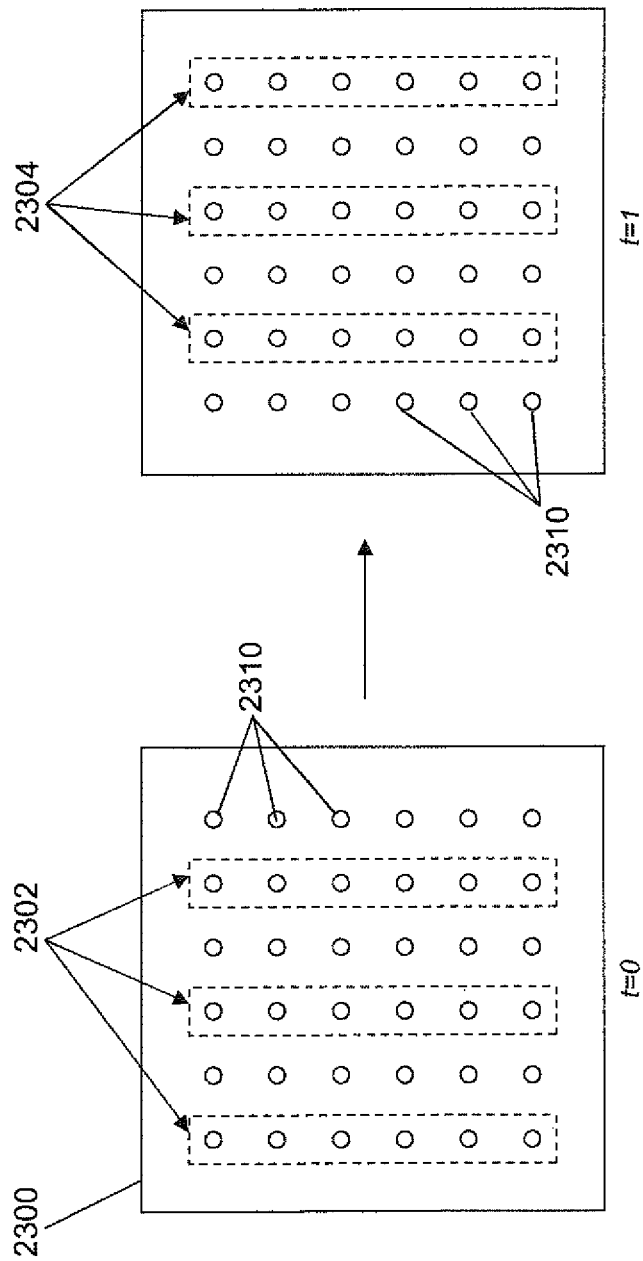
FIG. 23 schematically illustrates the process of time multiplexed illumination of discrete regions on a substrate.

This aspect of the present invention is schematically illustrated in FIG. 23. As shown, a first illumination pattern is provided upon a substrate 2300 that illuminates a first subset 2302 of reaction regions 2310 at a first time point, e.g., time t=0. The targeted illumination pattern is then switched to illuminate a different subset 2304 of regions 2310 at time t=1. For purposes of the -invention, t=0 and t=1 are sufficiently proximal in time, e.g., the switching is of a sufficient frequency, that the two illumination patterns are substantially simultaneous as that phrase is described elsewhere herein. Although shown as a two subset pattern switched between t=0 and t=1, it will be appreciated that a variety of different illumination patterns can be illuminated and switched within the desired timeframe to provide substantially simultaneous illumination of different regions, in accordance with the invention. For example, blocks, columns, sections, or random or arbitrary selections or subsets of regions may be separately illuminated in substantially simultaneous fashion.

Figure 24:
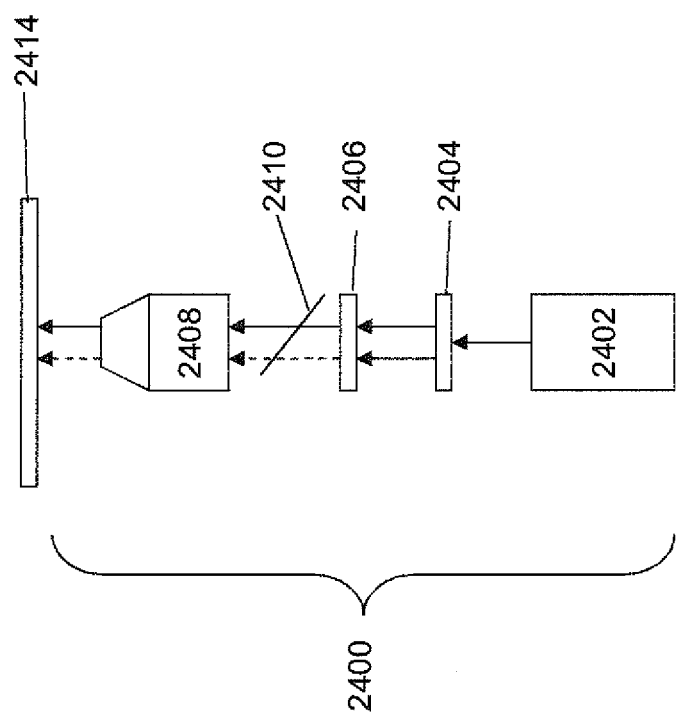
FIG. 24 schematically illustrates a system for carrying out time multiplexed illumination and detection of reactions in discrete regions of a substrate.

In at least one implementation, the time multiplexed systems of the invention employ an optical switching component that can selectively and rapidly switch among two or more different light paths that will illuminate different regions on the substrate. For example, in a first aspect, the illumination path of an analytical system includes a switchable directional mirror within the optical path to switch the direction of the excitation illumination to different locations on the substrate. In more complex systems, a programmable mirror array, such as a digital light processor (DLP), that is capable of rapidly directing targeted illumination at different portions of a substrate may be employed. Other dynamic switching components, e.g., that can selectively switch off the optical path for subsets or even individual beamlets include, e.g., MEMS shutter arrays, spatial light modulators such as LCD SLMs. An example of such an illumination path is illustrated in FIG. 24. As shown, the illumination path 2400, includes a source of excitation radiation, such as laser 2402. The laser is directed through appropriate multiplex optics, such as one or more diffractive optical elements, gratings, or the like, e.g., DOE 2404, to generate a targeted illumination pattern of the desired multiplex. The targeted illumination pattern is directed at a mirror 2406, which selectively directs portions of the illumination pattern through the remainder of the optical train, such as dichroic 2410 and objective 2408, to be incident upon a portion of the regions on the substrate 2414. Rapid switching of the mirror results in high frequency illumination of different regions on the substrate 2414 at different times, but preferably within the frame capture period of the detection system. In particularly preferred aspects, the switching system operates at a frequency that exceeds the acquisition rate of the detector in the system, e.g., the frame capture rate of the camera. In particular, by switching at least 1× in a single frame capture event, and preferably, at least 2×, and in some cases more often, e.g., at least 3×, 4×, 5× or more, in the time it takes a camera to acquire a single frame, the switching process should be largely undetectable and unobservable for the detection system. By way of example, for a high speed camera that has a frame rate of, e.g., from 100 to 1000 Hz, the switching frequency of the detection system should be at least 100 Hz, 200 Hz, 1000 Hz, 2000 Hz or even greater. As will be appreciated, in some cases, dynamic modulation of individual beamlets may be used to adjust the relative intensity of individual beamlets or subsets of beamlets, to adjust for variations across the substrate resulting from other aberrations in the optical system, e.g., vignetting, etc.

As will be appreciated, although described as intermittently transmitting different portions of the multiplexed beams from multiplex optics 2404 to substrate 2414, in some cases, the switching component may simply redirect the multiplexed beams to different portions of the substrate 2414, in order to further enhance the multiplex. For example, in some cases, the multiplex optics 2404 may generate an illumination pattern that illuminates a first subset of regions, e.g., subset 2302 in FIG. 23. The switching function then directs the same pattern of targeted illumination to an additional subset of regions, e.g., regions 2304 in FIG. 23. Accordingly, the multiplex optics may be selectively designed to provide the same, such as illuminating every other column or row of reaction regions. The switching optics, such as mirror 2406 are then configured to redirect the beams by one half period to illuminate the intervening columns or rows of reaction regions.

C. Search Active

Figure 25:
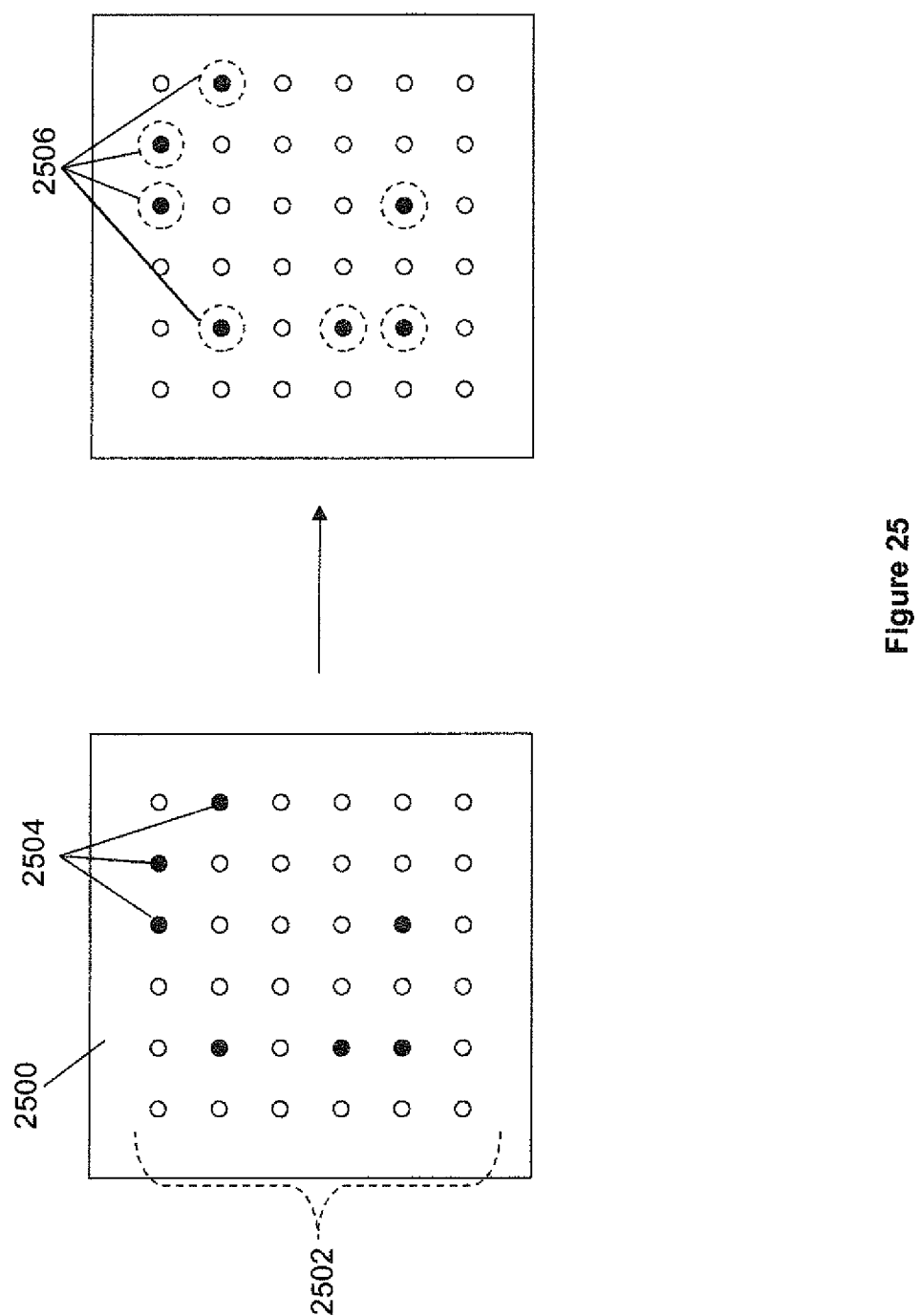
FIG. 25 schematically illustrates the process of "search active" multiplexing of analyses.

While many aspects of the present invention are directed at increasing the overall number of reaction regions that are subjected to illumination and/or detection for analysis of the reactions, in some cases, an effective multiplex is achieved through the initial interrogation of the high number of reaction regions followed by subsequent illumination and/or detection from only a subset of such regions that are active, e.g., showing indications of the reaction of interest. Thus, in still another aspect, the increased multiplex is applied only to active regions on a substrate. In effect, this process interrogates large numbers of reaction regions but only maintains an analysis of a small subset. Thus, while effectively initially interrogating a high multiplex, the ultimate analysis is performed on a substantially smaller subset of the reaction regions that may not even require an ultra-high multiplex factor. The resulting analysis provides an effective increase in multiplex, i.e., a higher level of throughput of analysis of relevant regions, while not maintaining high multiplex analysis over the entire analysis period. As a result, lower energy inputs may be required than a straightforward high multiplex approach, with the concurrent gains in signal to noise ratios, and the like. An overview of the aforementioned process is schematically illustrated in FIG. 25. As shown, a substrate 2500 having a large number of potential reaction regions 2502 is first broadly interrogated to identify active reaction regions (indicated as filled circles 2504). Such broad illumination may take the form of a unified flood illumination of the entire substrate or substantial portions thereof, or it may take the form of scanned analysis of the different regions to identify those demonstrating activity. Alternatively, targeted illumination approaches may be similarly employed to identify active regions 2504. Once identified, the optical system is then configured to illuminate only those regions demonstrating activity, resulting in illumination of and thus, monitoring of signals from only those regions (shown as dashed circles 2506).

Such selective illumination may employ a variety of different optical systems or components. For example, as with the time multiplexed illumination processes above, programmable mirror arrays may be rapidly configured to illuminate only selected precise regions on a given substrate. Likewise, LCD masks, e.g., as used in conventional flat panel LCD displays, having addressable pixels may be employed to selectively illuminate the desired regions on a substrate. Such components may be positioned as described with respect to mirror 2406 in FIG. 24, in order to selectively block beamlets destined for inactive regions of the substrate. In particular, by providing an LCD based mask, one can selectively address individual pixels to open or close them to the transmission of excitation illumination, e.g., beamlets, thus controlling the number and pattern of beamlets that are ultimately incident upon the substrate.

In addition to providing controllable masked illumination to different regions on a substrate, the foregoing approaches may also be applied in regulating the intensity of illumination at the various regions over a substrate. In particular, by modulating the light passage through different mask elements, one can modulate the intensity of light received at the substrate. The foregoing modulation is particularly useful in addressing non-uniformities in targeted illumination resulting from other optical components, e.g., non-uniformities resulting from variations in the multiplex optics, e.g., a DOE, or the like. In particular, a gray-scale mask may be fabricated, or in the case of programmable spatial light modulator, programmed to adjust for any predetermined non-uniformities in the targeted illumination among the various illuminated regions. In particular, one may obtain a sampling of the illumination profile for a given optical path, including multiplex optics, and based upon the pattern, configure the spatial light modulator or mask, appropriately to correct for deviations, e.g., reduce intensity of brighter illumination spots.

D. Enhanced Multiplex Illumination

In other aspects, the present invention provides for enhanced multiplex illumination using multiple illumination sources in combination with one or multiple diffractive elements, to illuminate large numbers of discrete reaction areas. In such cases, two, three, four, five, ten or more laser beams may be directed through one or more diffractive optical elements to generate large numbers of illumination spots on a substrate.

In illuminating large numbers of discrete regions on a substrate, e.g., using a diffractive optical element to provide discrete beams, ensuring adequate power is delivered to large numbers of illuminated areas typically requires increases in the power applied to the system. For ultra high multiplex systems, individual illumination sources for doing this are not commercially viable, due to cost and availability. For example, in certain exemplary applications, single illumination source beams are divided into beamlets that provide ~5 $\mu W/\mu m^2$. Achieving the same illumination power for 80,000 discrete spots would suggest a single illumination beam of ~500 mW.

In addition to laser issues, diffractive optical elements typically generate beam patterns that that have reasonable beam uniformity over relatively small fields of view. However, where one desires to expand the field of view, the non-uniformity of the illumination pattern can become excessive for certain applications. Thus, in expanding multiplex illumination, e.g., an order of magnitude or greater, one would expect substantial variation in illumination intensity across the illumination spots.

Accordingly, in one aspect, the present invention provides multiple illumination sources and/or source beams that are directed through the diffractive element or diffractive elements in order to provide ultra high multiplex illumination with readily available, lower power illumination sources, and greater uniformity across the field of illumination.

Figure 26:
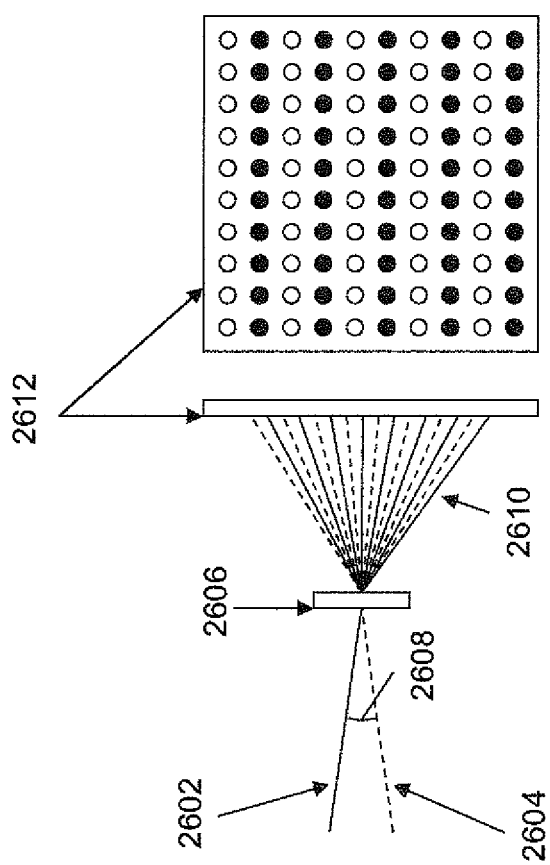
FIG. 26 schematically illustrates a multiplex illumination optical train.

In a first aspect, multiple illumination beams are directed through a single diffractive element at different angles in order to provide an output illumination pattern reflective of the multiple beams and angular variation in the originating beams. This is schematically illustrated in FIG. 26. As shown, multiple illumination beams, e.g., shown as solid line 2602 and dashed line 2604, are directed at a diffractive optical element 2606 at different angles, e.g., shown as angle 2608. The resulting pattern of illumination "beamlets" 2610 emanating from the DOE from each originating beam is directed upon the substrate 2612 in its own pattern (e.g., schematically illustrated as filled and unfilled spots on the substrate 2612), where each pattern is offset by a function of the angle difference between the two originating beams.

In addition to the use of multiple illumination source beams, the present invention also envisions the use of multiple diffractive elements, where each diffractive element receives a subset of originating illumination beams to yield an associated pattern. In particular, because higher multiplex patterns emanating from a single diffractive element may provide excessive variation over an entire larger field of view, one may employ multiple diffractive elements each of which provide an illumination pattern over a subset of regions of a particular substrate, such that the illumination variability is confined to that which exists in a relatively small field of view, and thus does not exceed the ranges for a desired application.

Figure 27:
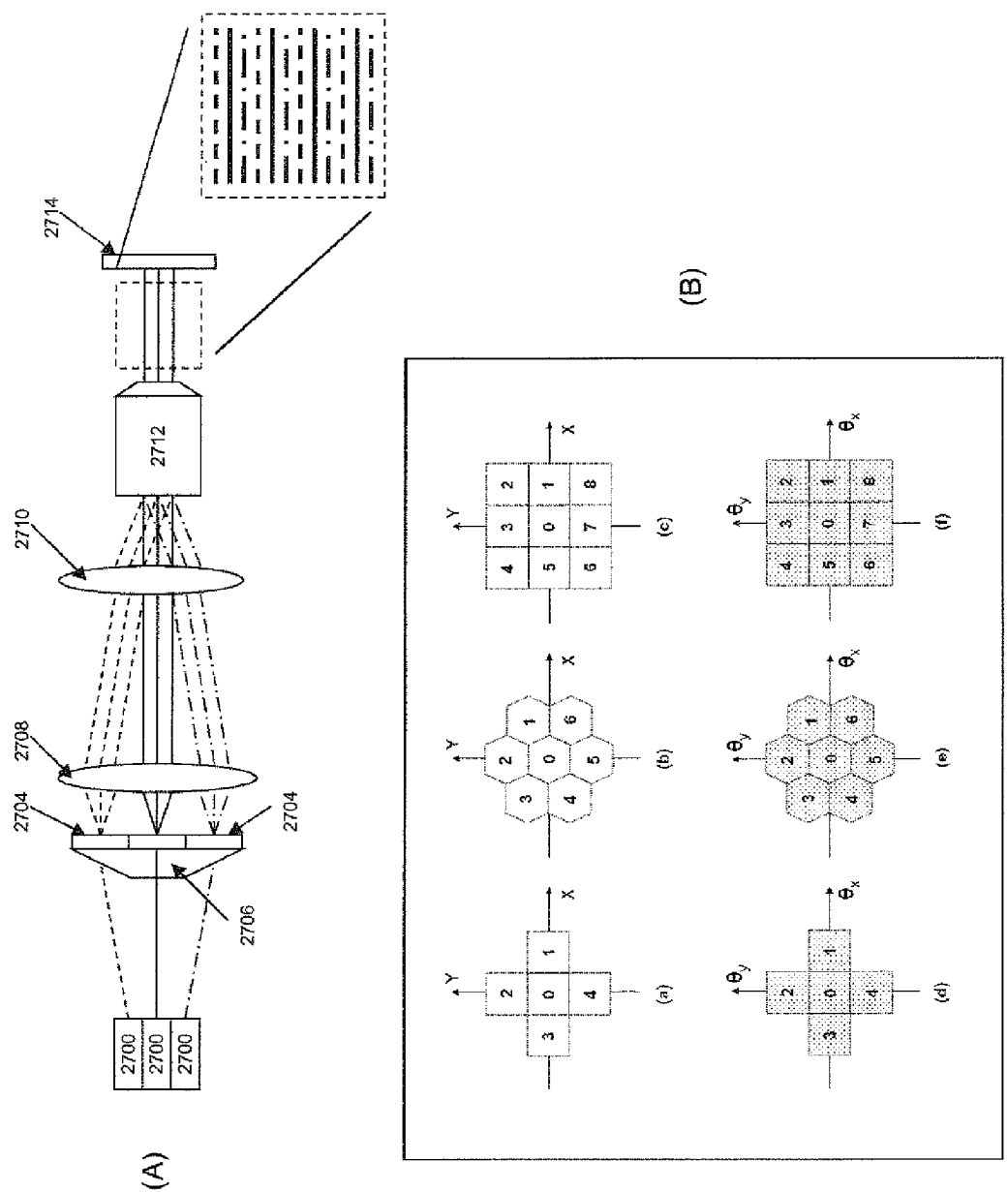
FIG. 27A-B schematically illustrates an additional multiplex illumination path for the systems of the invention.

One example of such a system is illustrated in FIG. 27A. In particular, as shown, a multiplexed diffractive optical element 2706, which may comprise a single integrated component or multiple connected diffractive optical elements 2704, is provided. Multiple originating illumination beams (shown as solid, short dashed and long dashed lines emanating from multiple illumination sources, e.g., lasers 2700) are directed at the multiplexed DOE 2706, where each beam is directed at the DOE at a slightly offset angle from the other beams. As shown, a faceted prism, waveguide array, fiber optic bundle, or other optical component may be included to redirect each beam to its appropriate DOE component. Further, each DOE component in the array may be angularly biased to provide optimal direction of the emanating beamlets through the remainder of the optical train.

The resulting beam pattern from each DOE element 2704 within the integrated DOE 2706 is then transmitted through the optical train (shown as lenses 2708, 2710, and objective 2712), which focuses the beams onto a substrate 2714. As shown, the different beams are focused to provide their illumination patterns to different subsets of the substrate. For example, as shown in schematic expanded view of the beams, the interleaving of illumination patterns from each component 2704 may be used to provide multiple offset, but interleaved illumination patterns on the substrate 2714, e.g., patterns as shown in FIG. 26. Alternatively, different beamlet patterns may be directed to wholly different regions on the substrate, e.g., quadrants, or the like, to illuminate separate substrate regions.

FIG. 27B illustrates a number of DOE component configurations for achieving high multiplex, including 5 DOE array components (a) and (d), 7 DOE array components (b) and (e), and 9 DOE array components (c) and (f). Other configurations are also available, depending upon the level of multiplex and the desired illumination pattern. In preferred aspects, each DOE component in an array will be configured to carry a different biased angular spread, in addition to splitting each incoming beam to the large number of beamlets in the illumination pattern uniformly in the angular space. For example, for the 9 facet DOE components illustrated in FIG. 27B, each individual DOE component or facet in the array may provide 100 by 100 beamlets from a single incoming beam. These may be uniformly spaced by, e.g., 0.1 mrad in both the $\theta x$ and $\theta y$ angular space. The biased angular spread for the first DOE (#1) would be, e.g., 5 mrad in the $\theta x$ direction, the second DOE (#2) would be biased 5 mrad in both the $\theta x$ and $\theta y$ angular space, the third. DOE (#3) would be biased 5 mrad in the $\theta y$ angular space, and so on.

As will be appreciated, and as alluded to above, each DOE may be used to convert one or more illumination beams into patterns of beamlets that are directed to the substrate.

E. Multiplex Detection

Similar to the multiplex approaches applied to the illumination side of the analytical systems described herein, and in addition to or as an alternative to such approaches, the present invention also provides for enhanced multiplex on the collection side of the system, e.g., the optical path for the collection and detection of signals emanating from reaction regions on a substrate. In particular, at least one limitation on the potential for ultra high multiplex systems, is the ability to detect signals emanating from larger and larger numbers of discrete regions, e.g., on a substrate. As will be appreciated, the expected practical limitation on detection of signals from different regions on a substrate at any given time, will be limited by the number of pixels or detector elements in a given detection system.

In particular, a given detector pixel will only be capable of detecting the signal incident upon it, and absent other considerations, will not distinguish between signal from one source and signal from another or combined sources. As will be understood, however, the practical limitation of one signal per pixel is, itself, not entirely practical, as detecting signals on multiple pixels provides myriad different information, such as spectral information, array location, and the like (See, e.g., Published U.S. Patent Application No. 2007-0206187, Published International Patent Application No. WO 2007/095119, and U.S. patent application Ser. No. 12/134,186, filed Jun. $5^{th}$, 2008, the full disclosures of each of which is incorporated herein by reference in its entirety for all purposes). Similarly, separation of the signal components on the array helps to prevent signal cross contamination. As a result of these and other considerations, in multiplex approaches, it would be advantageous to optimize the efficient use of detector array area.

In a first example signals emanating from an array of reaction regions on a substrate may be directed to different regions on a detector array or even entirely different detector arrays, in order to optimally detect signals from high multiplex substrates. In a related example, different signal components from individual signal sources may be directed to different detectors.

Alternatively or additionally, just as with the temporal switching of illumination, signals emanating from different regions of a substrate may be temporally separated, but otherwise directed to the same, overlapping, adjacent or discrete portions of a substrate at different times. Again, by applying such switching at a frequency that exceeds and preferably substantially exceeds the slowest signal duration, such temporal separation will provide seamless detection of the desired signal events. Further, by synchronizing the signal analysis processes with the switching, one can readily assign a signal event with a given location on the substrate, even when such signals are incident upon the same location of a detector array. As will be appreciated, the same or similar components may be employed for the optical switching of signal direction as were discussed for switching of the targeted illumination pattern, above. In addition, it will be appreciated that LCD masks, e.g., as discussed previously, may likewise be employed in the collection pathway to selectively open and close the collection path to signals from discrete reaction regions or subsets of reaction regions.

By "work-sharing" the detection area of the detector among different signal sources, albeit at distinct points in time, one can multiply the number of signal sources that can be detected using a single detector or set of detectors over a process where temporal multiplexing is not used.

In a related aspect and as alluded to above, an individual substrate comprising a large number of discrete reaction regions may be divided up into multiple different sub-fields of view (sub-FOV), each of which may be directed to a different detector in order to accommodate high multiplex substrates. In order to efficiently and simultaneously monitor these sub-FOVs, it would be preferably to maintain a single optical train that accomplishes this monitoring process. Accordingly, in one aspect, the present invention provides an optical system that illuminates a number of reaction regions on a substrate, but directs signals from each of a plurality of subsets of reaction regions to different detectors.

Figure 28:
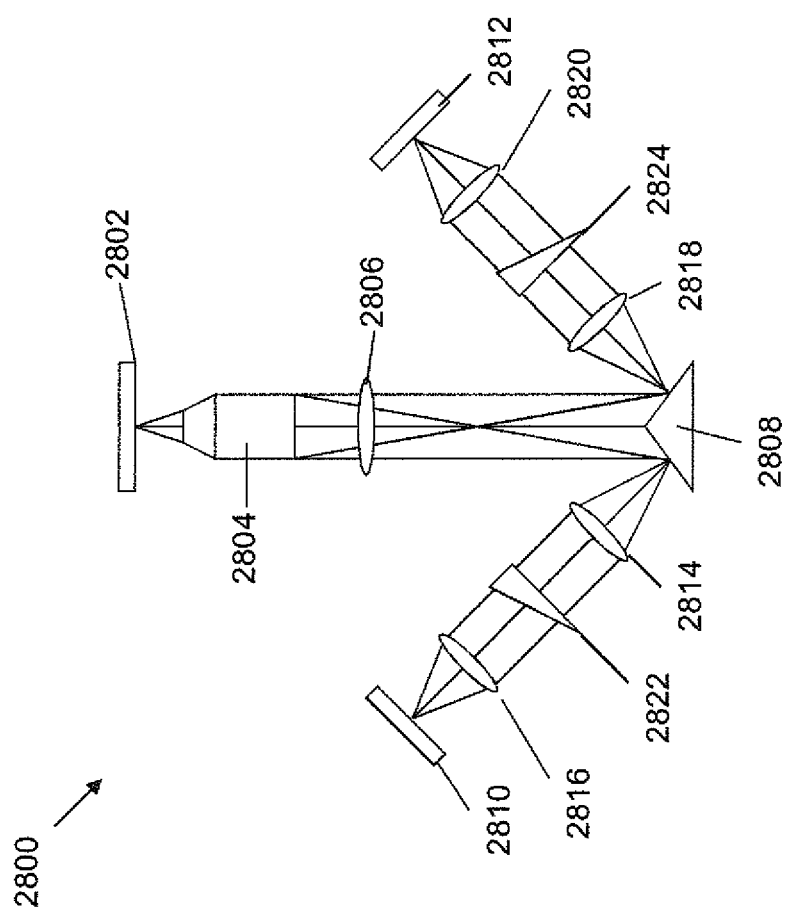
FIG. 28 schematically illustrates a system that employs multiple detection arrays for use in highly multiplexed analytical systems of the invention.

An example of an optical system for collecting fluorescent signals from different regions of a substrate and transmitting them to different detectors is schematically illustrated in FIG. 28. As shown, the system 2800 includes a substrate 2802 that has a number of discrete reaction regions or regions of interest disposed upon it or within it. The substrate 2802, and particularly, the regions for analysis, are disposed at the front focal plane of objective lens 2804. As shown, objective 2804 and tube lens 2806, image the regions of interest onto an intermediate image plane located at the back focal plane of the tube lens 2806, and near reflective mask 2808. The reflective mask 2808 splits the image and reflects a subset toward detector 2810 and a portion toward detector 2812. The apex of the reflective mask is typically provided in the focal plane so that no loss of fidelity results. Each of these detection paths are additionally shown to include spectral separation optics, e.g., focusing lenses 2814 and 2816, and 2818 and 2820, respectively, as well as dispersive optical elements for color separation, such as prisms 2822 and 2824, respectively. Although illustrated as dividing the image into two separately detected images, it will be appreciated that the reflective mask or other image dividing optics can be configured to divide the image into a larger number of image components, e.g., 2, 3, 4, 8, 16, or more discrete image components, each of which can be directed to a separate detector.

As alluded to previously, division of images can be accomplished a number of ways. For example, in a simple aspect, reflective mask 2808 may comprise, e.g., a pin-wheel mirror having separate biased segments, where each facet reflects a portion of the image in a different detection path. Alternatively, microprism or micromirror arrays are used, e.g., as reflective mask 2808, to direct images of each of the sub-FOVs to different detection paths, which have arrays of faceted surfaces that function to direct incident light in a desired direction. As will be appreciated, such arrays can be configured to split images into a number of discrete constituent images, in accordance with the invention.

In a related system, different signal components from the various signal sources on the substrate may be differentially directed to different detectors. In particular, in a single detector system, e.g., as shown in FIG. 22, multiple signal components would be spatially separated, e.g., by dispersive optical element 2216, and images upon the detector 2220. For ultra high multiplex array substrates, where the various signal sources are tightly packed on the array, the ability to spatially separate the images of the various signal components becomes much more difficult, as there is insufficient detector area to accommodate the separated components, and they begin to map to substantially overlapping portions of the detector array. By directing different signal components to different detectors, one can image more closely packed signal sources on the substrate. This is schematically illustrated in FIG. 29A. In particular, as shown in schematic image 2902, four signal components, e.g., spectrally distinct and separated fluorescent signal images 2904-2910), are imaged upon a portion of a detector array. By differentially directing subsets of the signal components, e.g., signals 2904/2906 and 2908/2910, to different detectors, one can effectively image nearly twice the number of signal sources, e.g., ZMWs, without concern for signal overlap. The number of imagable signal sources scales with the number of detectors, e.g., 2 detectors provides the ability to image up to 2× the signal sources. In preferred cases, however, additional spacing requirements for differentiating between adjacent signal sources may necessitate greater spacing between signal components from different sources. As such, the number of imagable signal sources may not exactly track with the number of detectors.

Figure 29B:
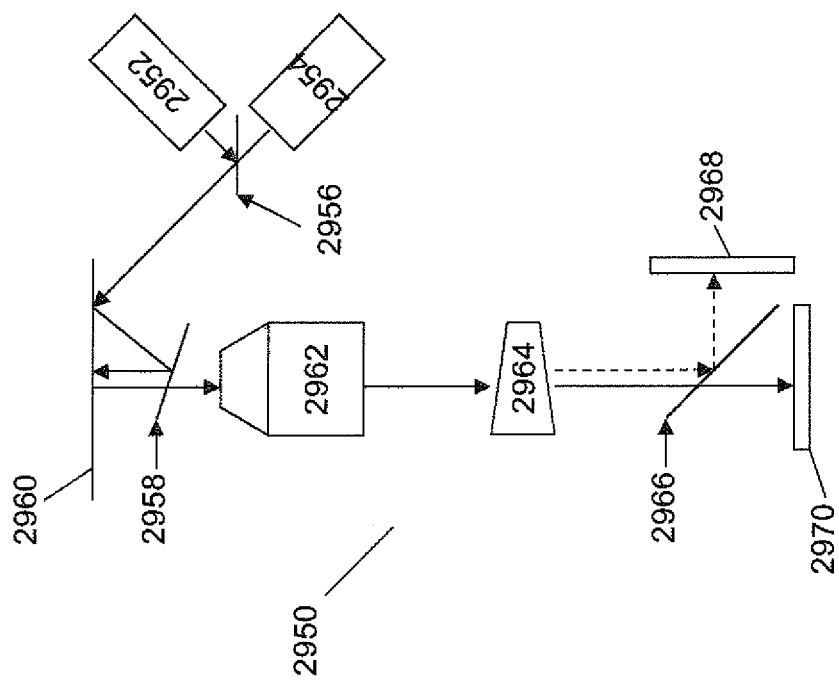
FIG. 29A-B schematically illustrates an alternate system employing multiple detection arrays where each array receives a subset of signal components from each signal source.
Figure 29A:
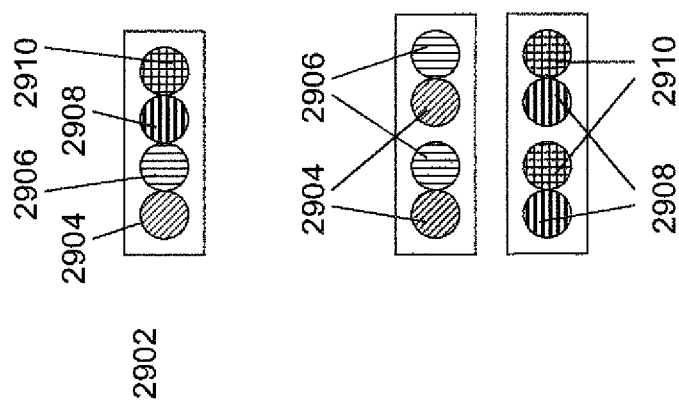

A schematic illustration of the optical system for accomplishing the above described detection multiplex is provided in FIG. 29B. In the system shown, the system's excitation optics are set up similar to the system shown in FIG. 22, e.g., with a dichroic filter between the objective lens and the substrate. In particular, as shown, the overall system 2950, includes one or more excitation light source(s), such as lasers 2952 and 2954. As with all such systems, the number of excitation sources can vary according to the needs of the particular application, e.g., the excitation wavelengths of the various fluorophores employed in the system, and the wavelength of the lasers used. In the exemplary system shown, two excitation light sources (illumination light sources) are combined into the same optical path by directing them at dichroic 2956, which transmits light from laser 2954 and reflects the beam from laser 2952, such that the two beams become co-linear. Again, in the system shown, the excitation beams are directed at an additional dichroic 2958, which serves to reflect the excitation light toward the substrate 2960, while transmitting fluorescent signals of a different wavelength to the collection objective lens 2962. As shown, the signal is first reflected off the surface of another component, e.g., a separate mirror in the optical train, or the back surface of the substrate, e.g., as described with respect to FIG. 22, above. The spectrally distinct signal components from the substrate 2960, e.g., emissions from different fluorescently labeled reagents, are then passed through the dichroic 2958 and objective lens 2962. The signal components are then separated into spectrally distinct signal components by passing them through a dispersive optical element, such as wedge prism 2964 (as illustrated by the solid and dashed arrows emanating from prism 2964). The signal components are then directed at dichroic 2966, which is reflective to one subset of the signal components and transmissive to another set of signal components. Each of the different subsets of signal components are then imaged upon either detector 2968 or 2970. As noted above, although shown as having two detectors, it will be appreciated that additional detectors may be employed to image further subsets of the signal components, e.g., one could have four signal components each directed to a different detector through the use of additional dichroics.

F. Glass-filled Object Space

One aspect of the invention provides an improved optical system having a glass-filled optic space. As described herein, the optics systems used for analysis of the arrays of reaction regions having, for example, fluorescent reagents for analyzing chemical reactions generally have illumination optics which impinge on the reaction regions, and collection optics to detect light emitted by the reaction occurring in the reaction regions. In some cases a dichroic element can be used to control the optical paths of the illumination and collection systems by acting as a mirror, for example for light at the illumination wavelength, but transmitting light at the emission wavelength In some cases, the use of a free-standing dichroic can lead to optical aberration and to losses. In the present invention, a shaped optic block having an embedded dichroic element is incorporated into the optical space between the illumination optics and the sample and between the collection optics and the sample. The optics block will typically have a refractive index that is greater than that of air. By having a higher refractive index, a greater proportion of the emitted light is collected by detection optics of a given entrance pupil diameter. In addition, by having the dichroic embedded within the optic block, the off-normal angle and cone angle of rays incident on the block are reduced, leading in some cases to better dichroic spectral performance and increasing system sensitivity.

Figure 30:
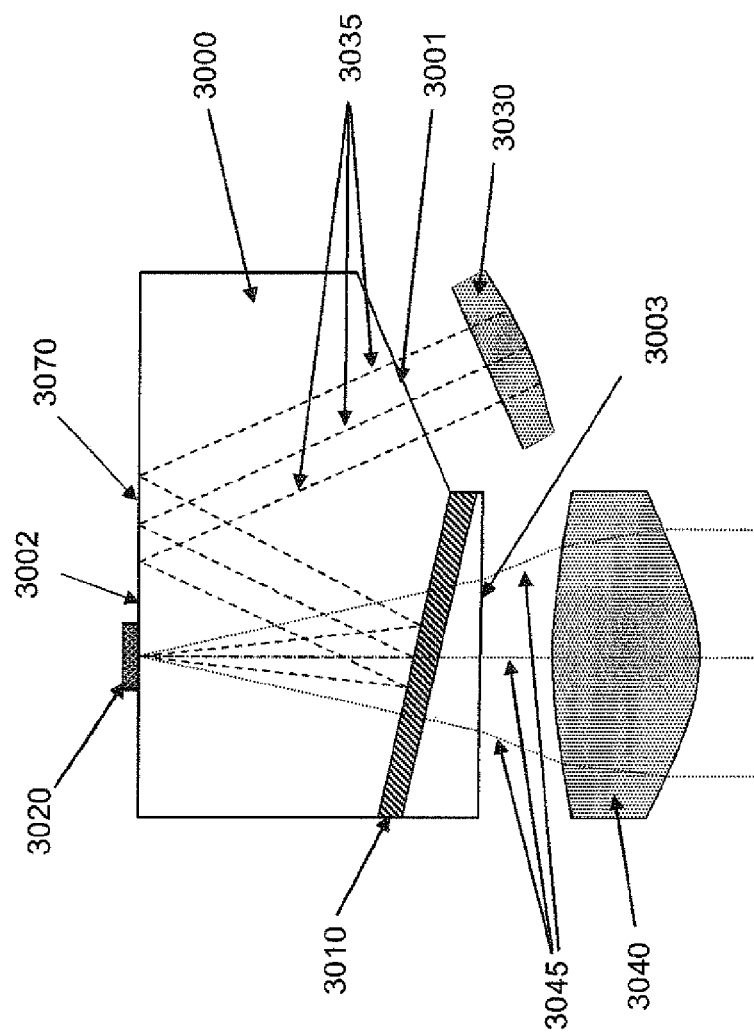
FIG. 30 schematically illustrates a shaped optics block of the invention.

An exemplary embodiment of a system comprising a shaped optics block is shown in FIG. 30. Illumination (excitation) optics 3030 direct illumination light 3035 through face 3001 into the optical block 3000. In the embodiment shown, the illumination light reflects off of face 3002, which is coated in region 3070 with a reflective material to enhance internal reflection. The illumination light is then reflected off of embedded dichroic element 3010, through face 3002 into substrate 3020 which may comprise multiple reaction regions having reactions that can be measured by the detection of fluorescent events. Emitted light 3045, e.g. fluorescent emission from the reaction regions, enters the block through face 3002, and is transmitted through the dichroic element 3010. In the embodiment shown, the substrate 3020 is optically coupled to the optical block 3000 to minimize reflective losses and aberrations. The emitted light then exits the shaped optical block through face 3003 and into collection optics 3040. While FIG. 30 shows reflection of the illumination light and transmission of the emitted light, in some embodiments, the embedded dichroic will transmit the illumination light and reflect the emitted light.

The faces of the shaped optics block through which the illumination light and collection light are transmitted can be planar, and can be disposed at an angle that maximizes optical performance. For example, the faces can be produced to be normal to the principal rays of the relevant optical train. In this manner, the shaped block can act, for the purposes of aberration correction, as a thick, untilted flat plate. In some embodiments, one or more faces of the shaped optics block can be curved to redirect the light which passes through the face, providing a lensing function. The faces can be curved in a concave or a convex manner as desired to redirect either the illumination light of the emitted light.

It is generally anticipated that the optics block will comprise the majority of the path optical path-length of the system. That is, the optical path distance through the optics block will be at least 50%, at least 60%, at least 70%, at least 80%, at least 90%, at least 95%, at least 98%, at least 99%, or more of the total optical path distance between the illumination optics and the substrate, or between the collection optics and the substrate. In some cases, the illumination optics, the substrate, the collection optics or any combination of the above are optically coupled to the shaped optics block with a material having a higher index of refraction than air. For example the elements can be optically coupled using a fluid, oil, or polymer that provides an index of refraction that is closely matched to that of the shaped optical block or another component.

The dichroic element is embedded in the shaped optics block, indicating that the dichroic element is in optical contact with the block, and that there is generally little or no air space between the dichroic element and the optical block. In some cases, the dichroic can be molded or formed into the shaped optics block. In other cases, the dichroic element can be coupled to the portions of the optical block, for example with fluid, oil, or polymeric materials.

The shaped optics block is made from a material that is transparent at the wavelength of interest. The block can be made, for example from glassy oxide materials. The block can comprise, for example, silicon dioxide or calcium fluoride. Additives can be incorporated to adjust the refractive index and other properties of the block. It can be desirable in some cases for the block to have a refractive index of between about 1.1 and about 5.0 at the wavelength of interest. The refractive index can be, for example, or between about 1.3 and about 2.5, or between about 1.4 and 2.0. While in some cases it is desirable that the refractive index be high, in some cases, materials having higher refractive indices will tend to have higher levels of autofluorescence. Thus we have found that materials with refractive indices within these ranges can be particularly useful. It is generally desired that the block have low levels of autofluorescence at the wavelength range used in the analysis. Typically the analysis system will use visible light, for example, in the range of about 400 nm to about 700 nm. Infrared and ultraviolet light can also be used. The wavelength of the illumination light will generally be different than the wavelength of the emitted light.

III. EXAMPLES

Example 1

Parabolic Mirror Substrates

Substrates were fabricated having zero mode waveguides disposed through a metal layer that was deposited over a parabolic feature defined in a glass substrate. The devices were fabricated according to the process set out in FIG. 10 and the accompanying description, except that subsequent planarization of the substrate was not carried out (steps V-VII). The aperture through the metal layer which defines the core of the zero mode waveguide was fabricated using a focused ion beam (FIB etch process) to define a core of approximately 120 nm in diameter. The resulting structure is shown in FIG. 31A, under scanning electron microscopy (SEM), imaged from the metal layer side of the structure. The core of the zero mode waveguide is visible as the opening in the center top of the structure.

Figure 31B:
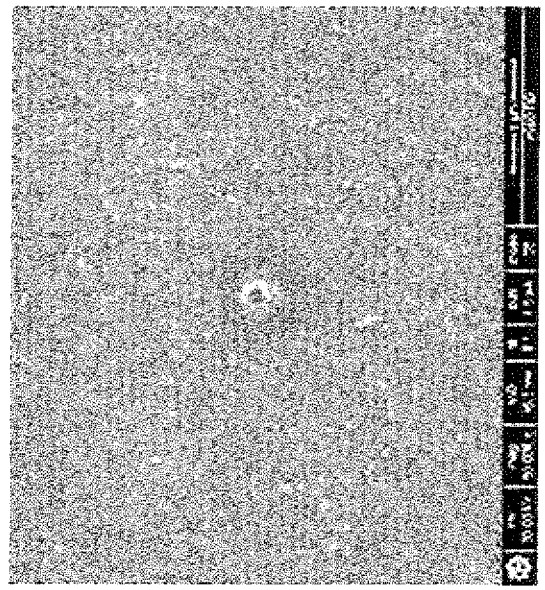
FIG. 31 shows SEM images of a parabolic microreflector structure (FIG. 31A) and a planar zero mode waveguide (FIG. 31B).
Figure 31A:
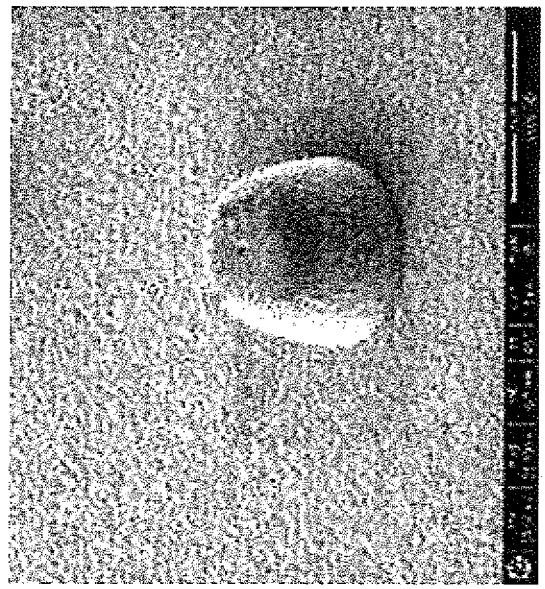

A comparison substrate was also provided having a zero mode waveguide of approximately the same cross sectional dimensions disposed in a planar metal layer over a planar glass substrate, e.g., not having any parabolic or other reflective structure, shown in FIG. 31B. The operation of the reflective structure in conveying light to or from a zero mode waveguide core was tested. A fluorescent dye was deposited over the open side of the two different waveguide structures and both were illuminated with the same excitation illumination, and emitted fluorescence was detected. Based upon an average fluorescence intensity from a set of zero mode waveguides in each of the two comparison substrates, it was found that the waveguide disposed over the reflective structure provided a fluorescent signal 6 times greater than a conventional ZMW, indicating an enhanced collection efficiency for an overall system.

Example 2

Theoretical Modeling of Conical Mirror Substrates

Figure 32:
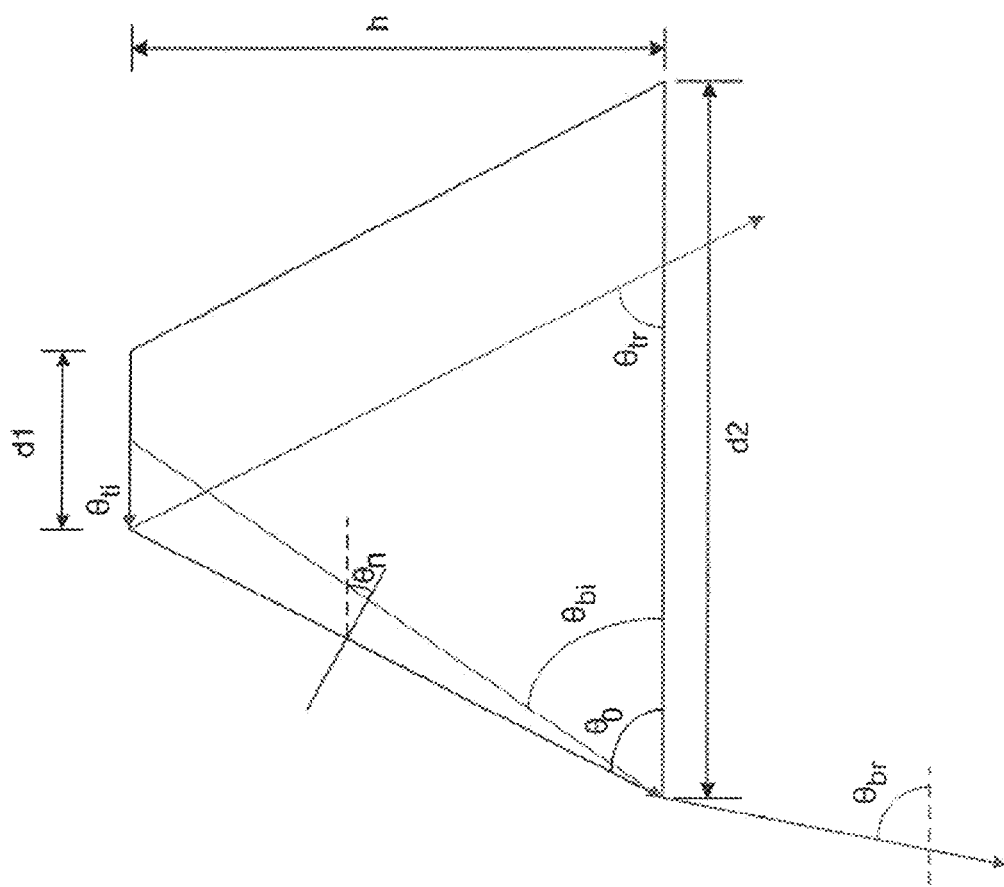
FIG. 32 illustrates the dimensional components used in modeling a conical microreflector.
Figure 33:
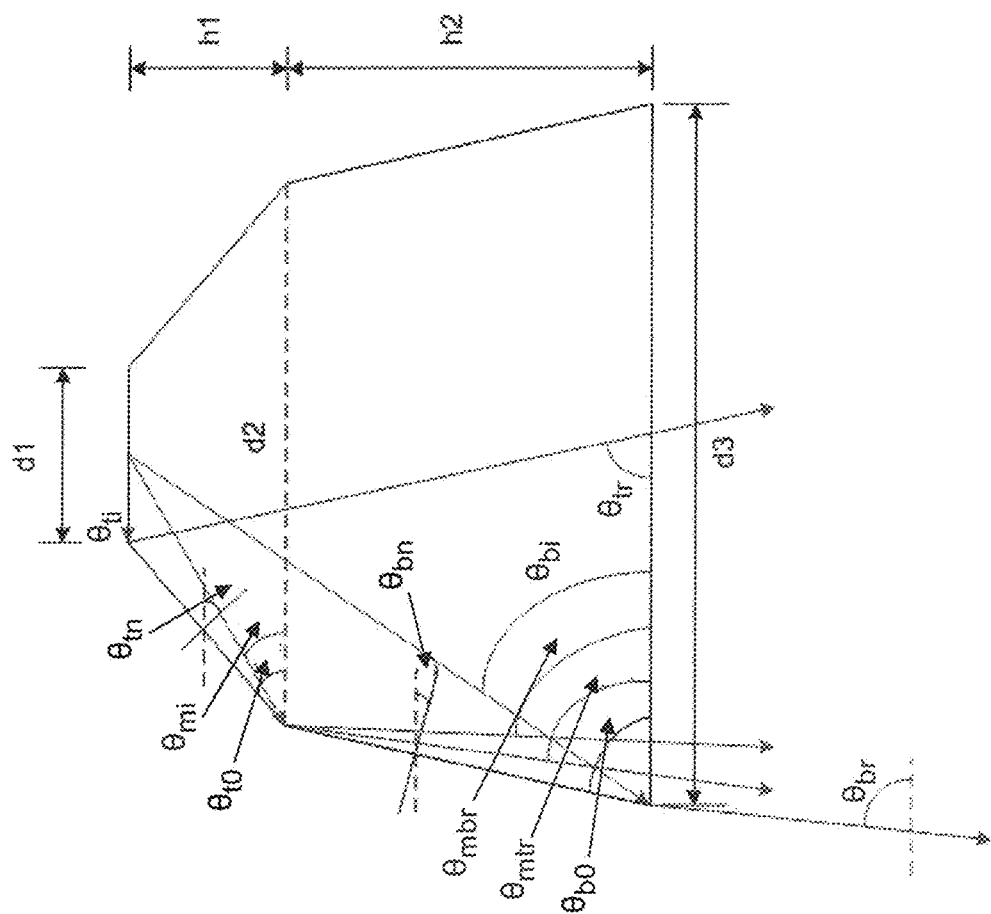
FIG. 33 illustrates the dimensional components used in modeling a staged conical microreflector.

Structures were modeled using the various components illustrated in FIGS. 32 and 33, respectively. For example, with respect to the straight conical structure illustrated in FIG. 32, dimensions were set as follows: d1=1.25 µm; d2=5 µm and h=4.69 µm. The model assumed that an objective lens used to collect emitted light from the substrate/reflector component has a numerical aperture of 0.5 with a highest collection angle of +/−20 degrees with respect to the optical axis, thereby providing a collection angle with respect to the bottom surface of the substrate of from 70 to 110 degrees. Based upon the conical model shown in FIG. 32, the ray angle that is reflected out of the cone is from 43.58 ($\theta_{tr}$) to 105.52 ($\theta_{br}$) degrees.

For the two staged conical reflector shown in FIG. 33, the dimensions were set to: d1=1.25 µm; d2=3 µm; d3=5 µm; h1=1 µm; and h2=3.69 µm. In this case, the ray angle that is reflected and comes out of the reflector ranges from 82.37 ($\theta_{tr}$) to 116.06 ($\theta_{br}$) degrees.

For both of the foregoing structural schemes, the photon collection efficiency for the objective is estimated to be approximately 70%, as compared to collection efficiencies of approximately 42% for a substrate that includes no reflector component, e.g., a zero mode waveguide disposed upon a transparent substrate layer, e.g., as shown in FIG. 31B, using a collection objective with a numerical aperture of 0.95. This analysis predicts improvements in optical performance from the incorporation of micromirrors, but this analysis, being essentially a ray-tracing analysis does not include diffraction or wave effects, and thus does not provide a complete picture of the expected performance. Analyses performed with vector-based tools have also been performed which confirm optical improvement from the micromirror structures of the invention.

Example 3

Production of Array of Nanoscale Reaction Regions on Micromirror Structures Using Sacrificial Pillars Polygermanium was deposited onto fused silica as a 500 nm layer by LPCVD at 350° C. Pillars were etched into a polygermanium using a 248 nm stepper, Lam etcher, width tuning from 300 nm to 120-150 nm. Mirrors were etched using a 248 nm stepper and Centura-MXP etcher. The array was then annealed at 600° C. to reduce autofluorescence and outgass the organic contaminants, followed by evaporation of aluminum and de-capping (removal of the polygermanium) in wet solution (30% $H_2O_2$ at 50° C.) without attacking aluminum on mirror facets.

Figure 34:
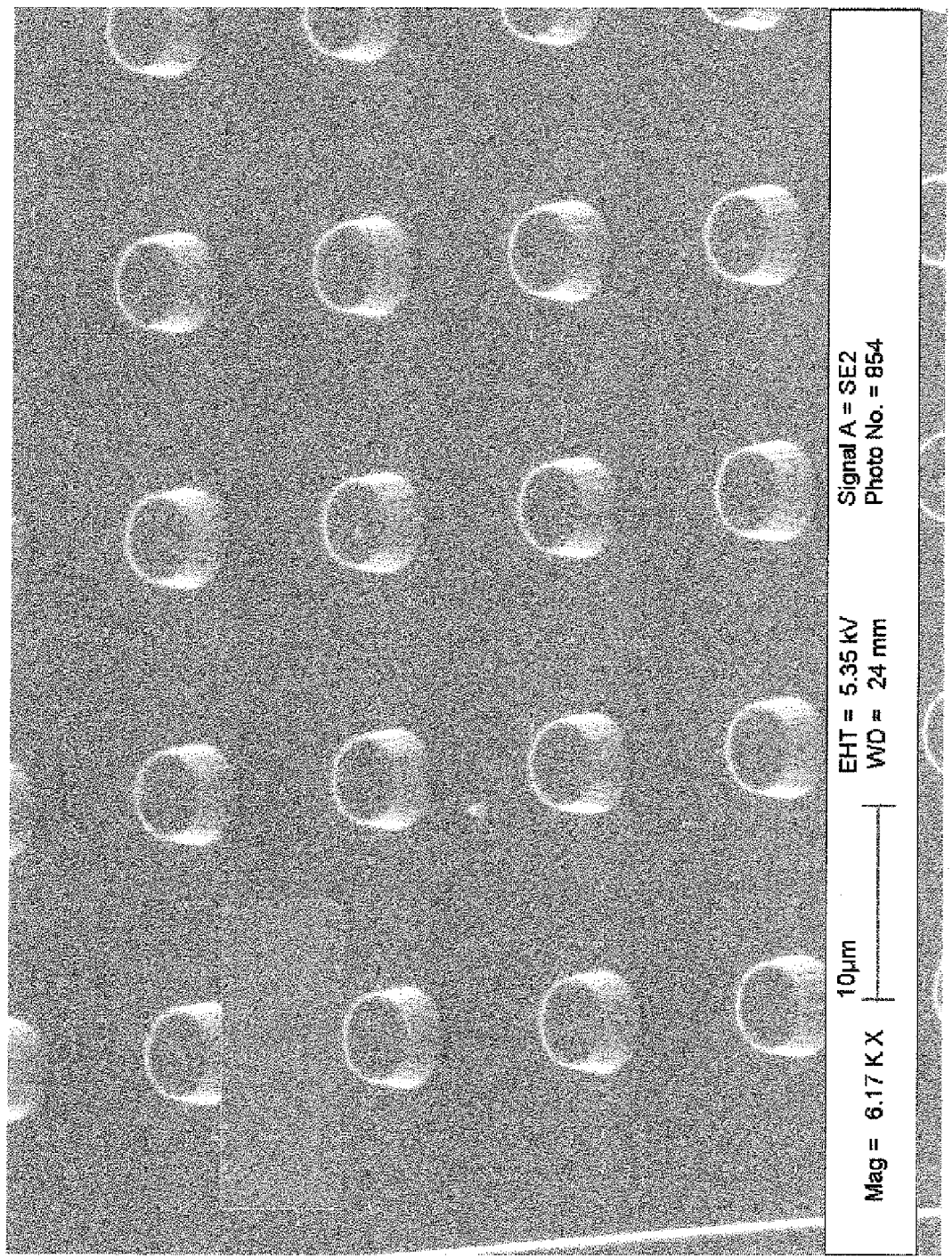
FIG. 34 shows an SEM image of an array of reaction regions on top of micromirrors formed in a fused silica substrate.
Figure 35:
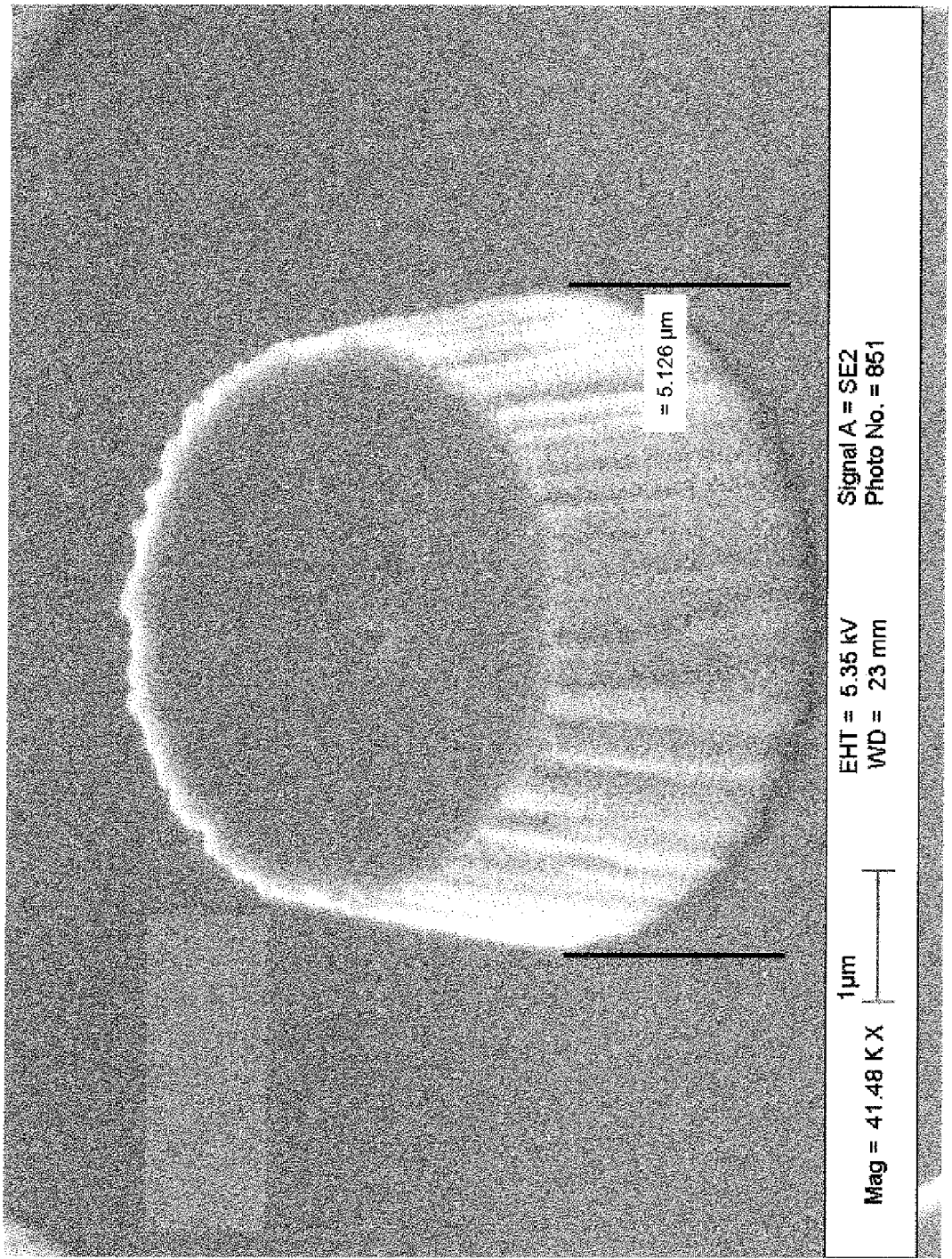
FIG. 35 shows an SEM image of a micromirror structure having a reaction region on its top.
Figure 36:
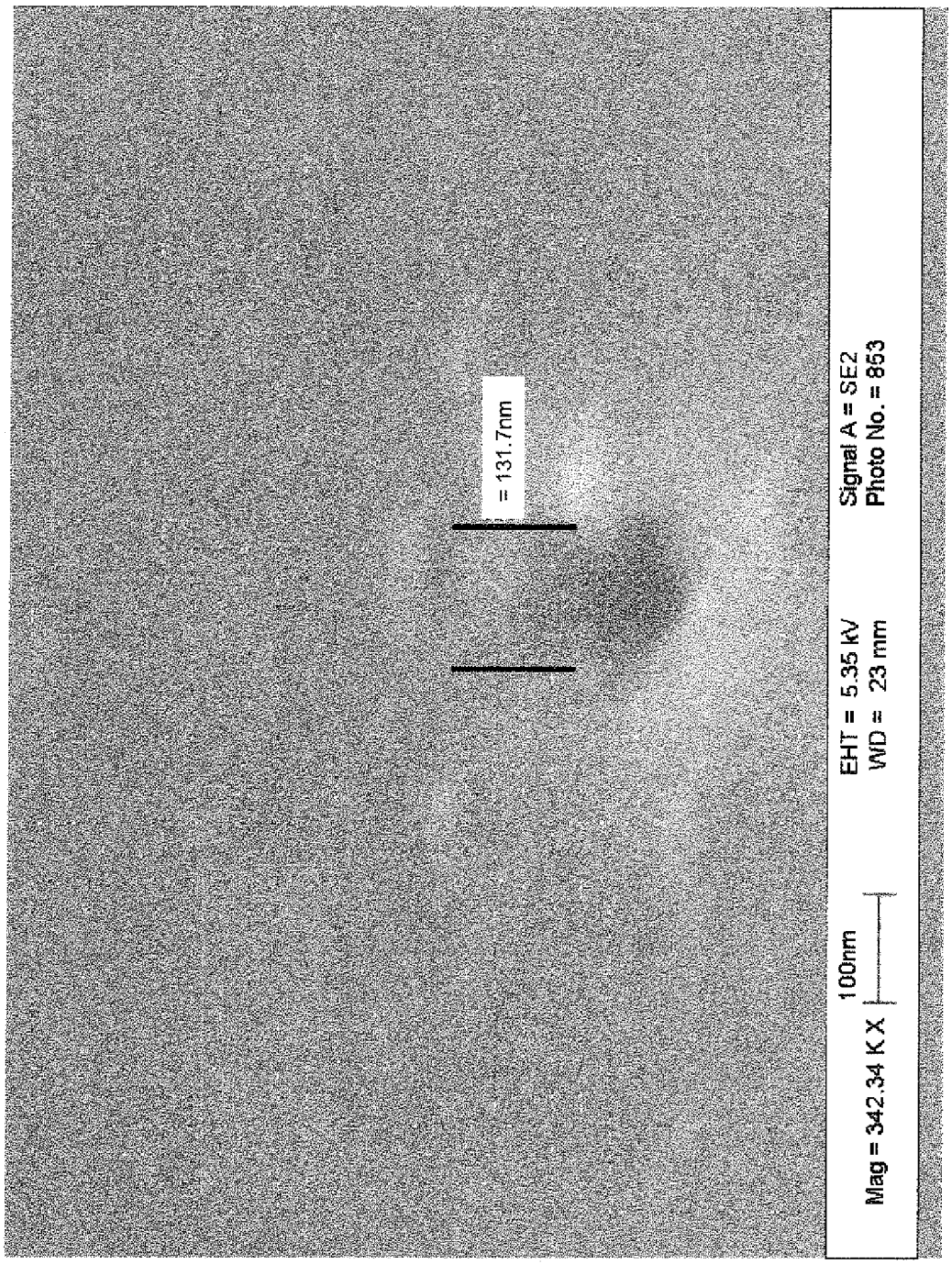
FIG. 36 shows an SEM image of a reaction region on the top of a micromirror structure.

FIG. 34 shows an SEM micrograph showing a portion of the array of reaction regions with associated micromirrors. FIG. 35 shows a single micromirror structure having a reaction region on its top. FIG. 36 shows a nanoscale reaction region on the top of a micromirror structure.

Example 4

Production of Nanoscale Reaction Regions Using a Sacrificial Germanium Layer and a Hard-Coat Mask A fused silica substrate is coated with a polycrystalline germanium layer followed by a hard-mask layer such as silicon dioxide or silicon nitride. Photolithography is used to define an array of circles having a diameter of about 380 nm, and the hard-mask is etched to produce discs of hard-mask having about these dimensions. The germanium layer is then etched using a controlled over-etch with 30% aqueous hydrogen peroxide to produce germanium pillars having diameters of about 200 nm under the hard-mask discs. The etch rate can be controlled by adjusting the conditions and the materials. For example, using undoped poly-Ge the etch rate for 30% aqueous hydrogen peroxide at 50° C. is about 460 nm/min, and using doped poly-Ge the etch rate for 30% aqueous hydrogen peroxide at room temperature is about 200 nm/min. Aluminum is sputtered onto the surface with a thickness of about 100 nm. The polycrystalline germanium pillars are removed using aqueous hydrogen peroxide heated to above about 50° C. SEM micrographs verify that holes ranging from 200 nm to 250 nm in diameter in an aluminum film on fused silica were generated.

Example 5

Conical Micromirror Structures Created on a Fused Silica Substrate

Figure 37:
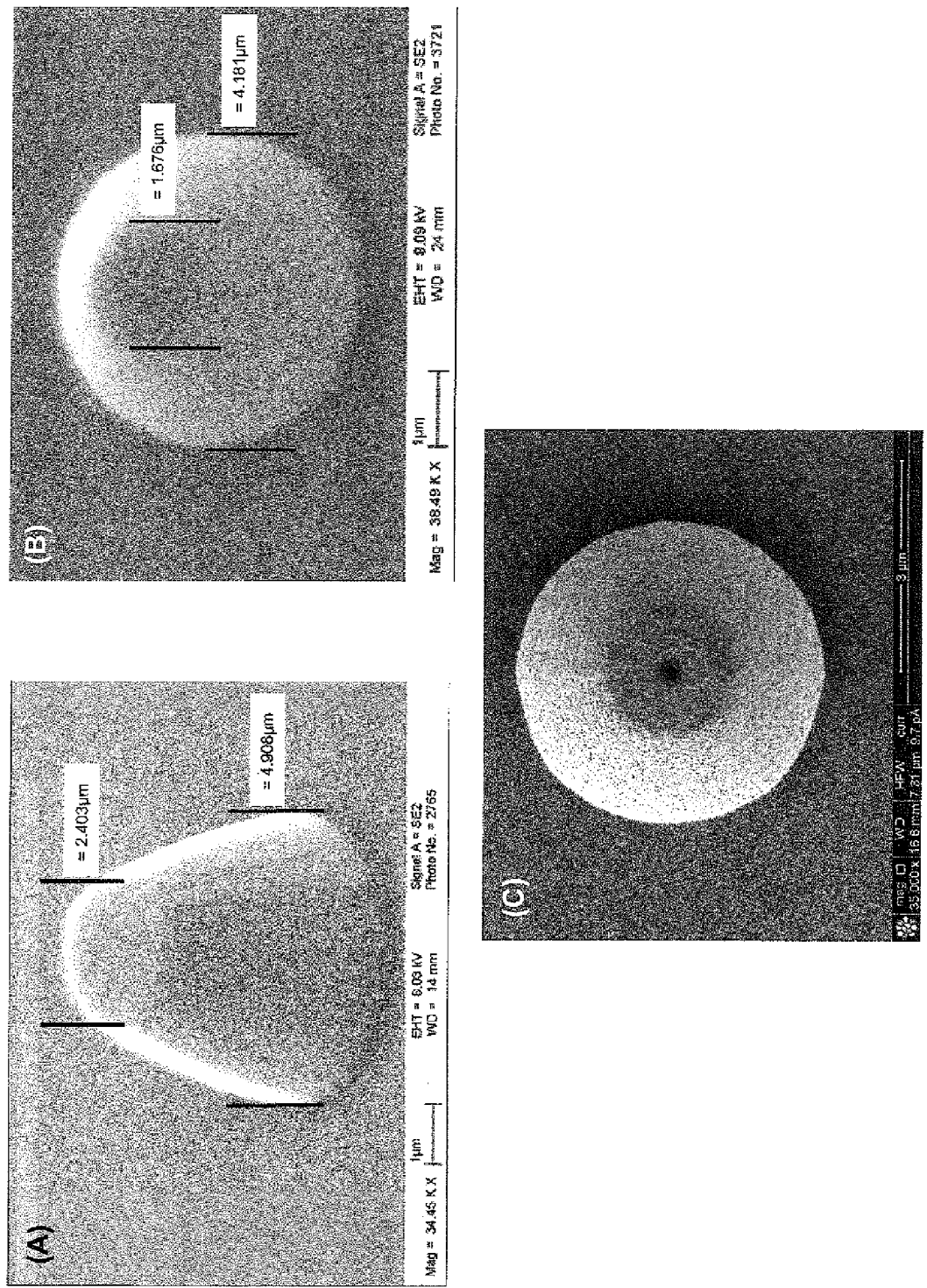
FIG. 37A-C shows SEM images of conical micromirror structures formed in a fused silica substrate.

FIG. 37 and shows scanning electron micrographs of exemplary conical micromirror structures that were formed on a fused silica substrate. The diameter of the top of the conical structure of FIG. 37(A) was measured to be about 2.40 microns, and the diameter of the base to be about 4.90 microns. The diameters of the top of the conical structure of FIG. 37(B) was measured to be about 1.68 microns, and the diameter of the base to be about 4.18 microns. Other micromirror structures made on fused silica substrates (not shown) were determined to have top diameter/bottom diameter/height of about: 1.30/3.96/3.45 microns, 1.49/4.17/3.18 microns, 1.68/4.34/3.30 microns, 2.79/5.27/3.36 microns, 2.55/5.60/3.23 microns, 2.66/5.38/3.72 microns.

FIG. 37(C) shows a conical micromirror structure coated with aluminum, having an zero mode waveguide aperture through the aluminum layer on the top of the micromirror structure.

Figure 38:
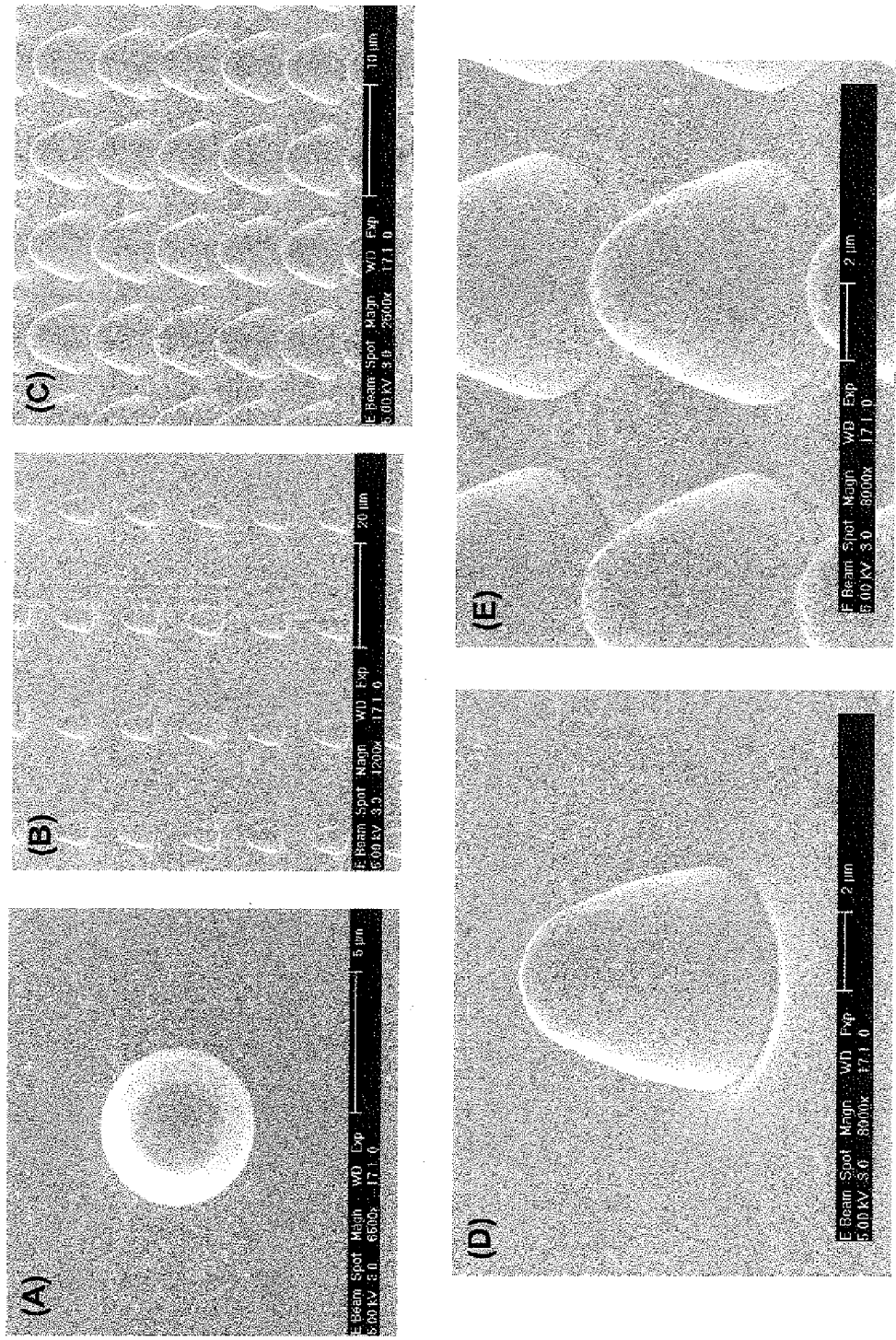
FIG. 38A-E show SEM images of conical micromirror structures formed in a fused silica substrate.
Figure 39:
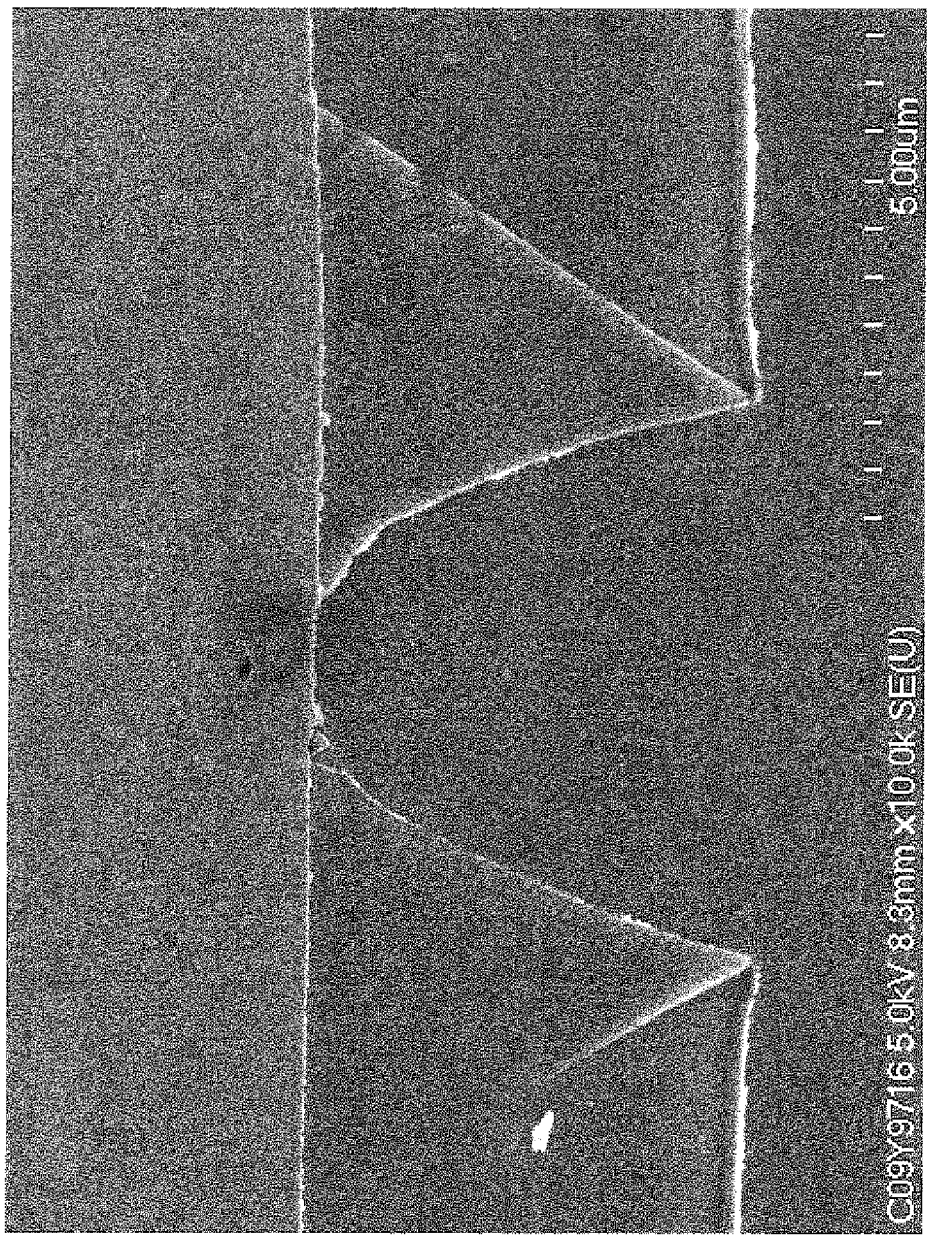
FIG. 39 shows an SEM image of a cross-section of a micromirror structure within a planarization layer and having a reaction region on its top.

FIGS. 38 (A)-(E) show SEM micrographs of conical structures produced in a fused silica substrate. The structures of FIG. 38 correspond, for example to structures after step (II) of the process depicted in FIG. 15. FIG. 39 shows an SEM micrograph of a cross section of a micromirror having an aperture on the top of it. The structure shown in FIG. 39 corresponds to a structure formed after step (VIII) of the process shown in FIG. 15. In this structure, the micromirror structure is surrounded by a planarization layer such as a spin-on-glass.

Figure 40:
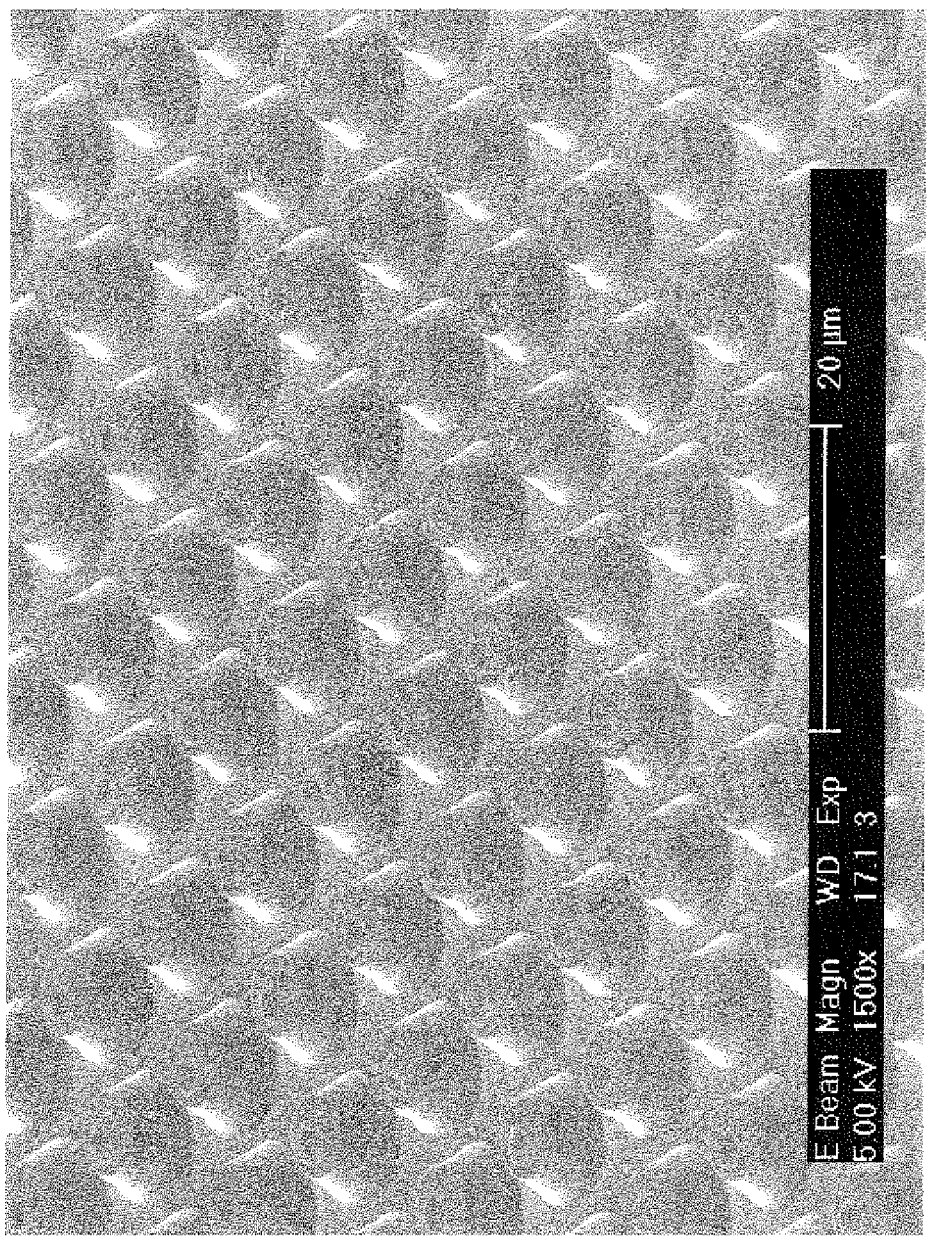
FIG. 40 shows an SEM image of micromirror structures having reaction regions on their tops.

FIG. 40 shows an array of micromirror structures, each having apertures on top of them produced on a fused silica substrate.

Example 6

Gain Measurements on Conical Micromirror Structures

Figure 41:
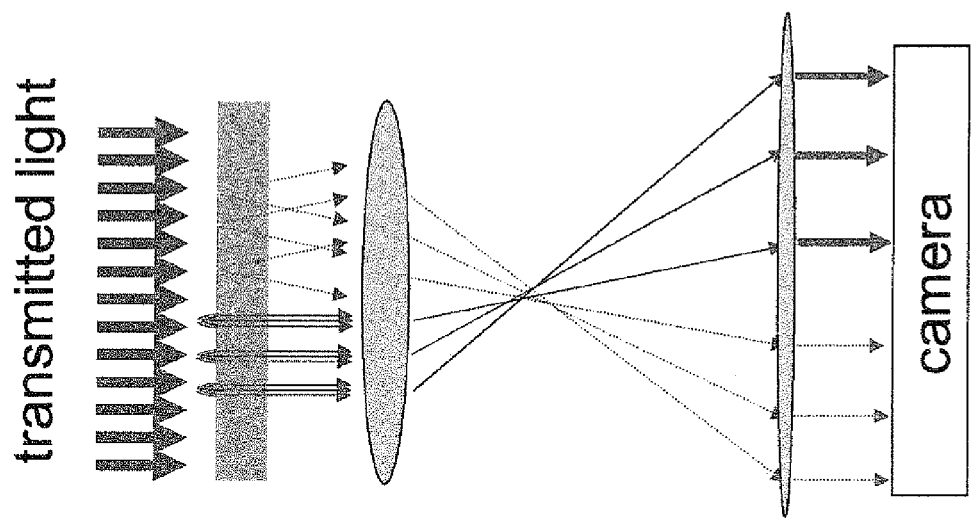
FIG. 41 shows a schematic illustration of an experimental setup for measuring the gain from micromirror structures.

Measurements were performed to determine the amount of gain that would be obtained from using micromirror structures coupled to zero mode waveguides. A substrate was prepared with FuSi having ZMW structures on the tops of micromirrors and having comparable ZMW structures on the planar portions of the substrate. FIG. 41 shows a schematic illustration of the experimental setup in which light is transmitted through the ZMW structures on the substrate. The light transmitted through the ZMW structures is collected with an optical train and detected on a CCD camera. The numerical aperture of the optical detection system was 0.5. Table 1 lists representative measurements of detected intensity from ZMW structures on the flat region of the substrate, and from ZMW structures on the tops of micromirror structures. The calculated gain from these measurements is about 5.9. It is understood that the measured gain will depend on the numeric aperture of the collection optics.

TABLE 1

Measurement of gain from micromirror structures

|  |  |
| --- | --- |
|  | 2530.99 |
| flat | 2793.91 |
|  | 2529.38 |
|  | 2858.07 |
|  | 2912.31 |
|  | 3086.77 |
| mirror | 15141.68 |
|  | 20340.43 |
|  | 19348.46 |
|  | 16883.04 |
|  | 13092.21 |
|  | 13952.95 |
| gain | 5.9 |

Example 7

DNA Sequencing in Reaction Regions on Micromirrors

Figure 42:
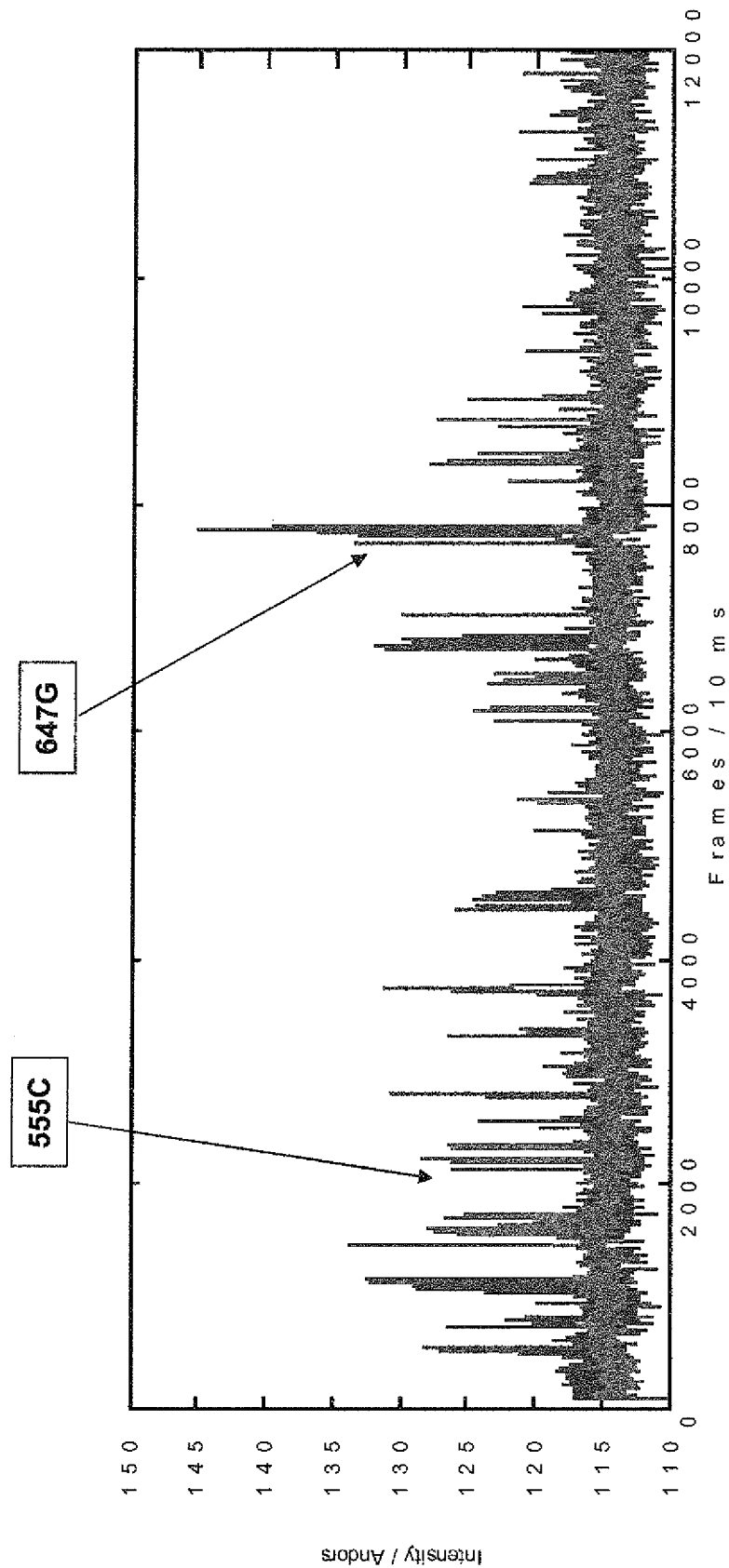
FIG. 42 shows two color DNA sequencing data obtained from zero mode waveguide reaction regions on micromirror structures.

An array of micromirror structures, each with a single zero mode waveguide aperture on its top surface was prepared from a 500 μm thick FuSi substrate. The micromirror structures were formed in the substrate using contact lithography with resist reflow and 3 micron deep reactive ion etching (RIE), followed by sputter smoothing and 400° C. annealing. A 200 nm Al layer was then sputter coated onto the surface. The Al layer was patterned and etched to produce a 120 nm diameter ZMW near the center of the top of the micromirror structures. Over etching was used such that the ZMW aperture extended about 50 nm into the FuSi substrate. A representative micromirror structure was determined to have a top diameter of about 3.4 microns and a bottom diameter of about 6.8 microns. A single molecule sequencing reaction was performed as described in Eid, et al. Science, 323, 133-138 (2009) with an optical system similar to that described in Lundquist et al., Optics Letters, 33, 1026 (2008) with a numerical aperture of 0.3. FIG. 42 shows a portion of data collected for intensity versus time for a 2-color sequencing reaction on a linear template having blocks of the bases C and G, which are identified by the dye labeled nucleotides 647G and 555C respectively as described in Eid et al. The dark peaks in FIG. 42 correspond with 647G, and the lighter peaks correspond to 555C, demonstrating nucleic acid sequencing using zero-mode waveguides with micromirror arrays. Four-color sequencing can be carried out in a similar manner, as described in Eid, et al.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

We claim:

1. An array for optical analysis comprising:
a transparent substrate having an upper surface comprising an array of at least 10,000 features comprising truncated cones having tops with diameters between about 0.5 microns and about 5 microns extending above the surface of the substrate, each feature having a top and sides, wherein the sides of the features comprise a reflective coating, wherein, on top of the transparent layer, and extending between the features, is a planarization layer, the planarization layer disposed such that the top of the planarization layer and the tops of the features are in the same plane, wherein, extending across the top of the planarization layer and tops of features is a cladding layer;
wherein the top of each of feature comprises a nanoscale aperture in the cladding layer, wherein light emitted down into the transparent layer from the nanoscale apertures is re-directed by the reflective coating on the sides of the array of features.

2. The array of claim 1 wherein the features comprise truncated cones having tops with diameters between about 1.5 microns and about 4 microns.

3. The array of claim 1 wherein the features comprise truncated cones having tops with diameters between about 2 microns and about 3 microns.

4. The array of claim 1 wherein the features comprise truncated cones having sidewall angles of between 5° and 40° from vertical.

5. The array of claim 1 wherein the features comprise truncated cones having sidewall angles of between 10° and 30° from vertical.

6. The array of claim 1 wherein the transparent substrate has a bottom surface, and the light that is directed down into the transparent substrate is directed out through the bottom surface of the substrate.

7. The array of claim 1 wherein the planarization layer comprises a spin-on-glass.

8. The may of claim 1 wherein the planarization layer comprises a polymeric material.

9. A system for measuring reactions in nanoscale apertures comprising:
   a) the array of claim 1;
   b) an illumination system that illuminates the nanoscale apertures through the bottom surface of the transparent substrate; and
   c) a detection system that detects the light emitted from the nanoscale apertures which is re-directed by the reflective coating on the sides of the array of features.

10. The system of claim 9 wherein the features comprise truncated cones having tops with diameters between about 1.5 microns and about 4 microns.

11. The system of claim 9 wherein the features comprise truncated cones having tops with diameters between about 2 microns and about 3 microns.

12. The system of claim 9 wherein the features comprise truncated cones having sidewall angles of between 5° and 40° from vertical.

13. The system of claim 9 wherein the features comprise truncated cones having sidewall angles of between 10° and 30° from vertical.

14. The system of claim 9 wherein the illumination system provides illumination beams to each of the nanoscale apertures.

\* \* \* \* \*